(12) United States Patent
Scherer et al.

(10) Patent No.: US 11,193,170 B2
(45) Date of Patent: Dec. 7, 2021

(54) METHOD OF DETERMINING DISEASE CAUSALITY OF GENOME MUTATIONS

(71) Applicant: The Hospital for Sick Children, Toronto (CA)

(72) Inventors: Stephen Scherer, Toronto (CA); Mohammed Uddin, Toronto (CA)

(73) Assignee: The Hospital for Sick Children, Toronto (CA)

( * ) Notice: Subject to any disclaimer, the term of this patent is extended or adjusted under 35 U.S.C. 154(b) by 654 days.

(21) Appl. No.: 15/092,113

(22) Filed: Apr. 6, 2016

(65) Prior Publication Data

US 2016/0326586 A1 Nov. 10, 2016

Related U.S. Application Data

(63) Continuation-in-part of application No. PCT/CA2014/000753, filed on Oct. 17, 2014.

(60) Provisional application No. 61/892,920, filed on Oct. 18, 2013.

(51) Int. Cl.
| | |
|---|---|
| *C12Q 1/6883* | (2018.01) |
| *G16B 30/00* | (2019.01) |
| *G16B 20/00* | (2019.01) |
| *G16B 20/20* | (2019.01) |
| *G16B 20/40* | (2019.01) |
| *G16B 20/10* | (2019.01) |

(52) U.S. Cl.
CPC ........... *C12Q 1/6883* (2013.01); *G16B 20/00* (2019.02); *G16B 20/10* (2019.02); *G16B 20/20* (2019.02); *G16B 20/40* (2019.02); *G16B 30/00* (2019.02); *C12Q 2600/156* (2013.01); *C12Q 2600/158* (2013.01)

(58) Field of Classification Search
None
See application file for complete search history.

(56) References Cited

U.S. PATENT DOCUMENTS

2010/0144538 A1 6/2010 Belouchi et al.

FOREIGN PATENT DOCUMENTS

WO WO-2012094681 A1 * 7/2012 ......... G01N 33/6896

OTHER PUBLICATIONS

Pinto et al. (Nature (2010) vol. 466:368-372).*
Kang et al. (Nature (2011) vol. 478:Supplemental Data; 57 pages.*
Tallantyre et al. (Journal of Neurology (2013) vol. 260:936-939).*
Won et al. (Nature Medicine (2011) vol. 17:566-572).*
W. Fu et al.—Analysis of 6,515 Exomes Reveals the Recent Origin of Most Human Protein-coding Variants—Nature 493, 216-220 (2013); published online EpubJan. 10 (10.1038/nature11690).
H.J. Kang et al.—"Spatio-temporal transcriptome of the human brain". Nature 478, 483-489 (2011); published online EpubOct. 27 (10.1038/nature 10523).
R. Andersson et al.—"An atlas of active enhancers across human cell types and tissues". Nature 507, 455-467 (2014).
M.S. Kim et al.—"A draft map of the human proteome"—Nature 509, 575-581 (2014).
E. Khurana et al.—"Interpretation of genomic variants using a unified biological network approach"—PLoS computational biology 9, e1002886 (2013), 9 pages.
N. Huang et al.—"Characterising and predicting haploinsufficiency in the human genome"—PLoS genetics 6, e1001154 (2010), 11 pages.
J. Steinberg et al.—"Haploinsufficiency predictions without study bias"—Nucleic acids research 43, e101 (2015), 9 pages.
C.S. Greene et al.—"Understanding multicellular function and disease with human tissue-specific networks"—Nature genetics 47, 569-576 (2015).
M. Uddin et al.—"Brain-expressed exons under purifying selection are enriched for de novo mutations in autism spectrum disorder"—Nature genetics 46, 742-747 (2014).

* cited by examiner

*Primary Examiner* — Lori A. Clow

(74) *Attorney, Agent, or Firm* — Susan Tandan; Gowling WLG (Canada) LLP

(57) ABSTRACT

A method of identifying a gene or genomic mutation that is linked to causality of a neuropsychiatric disorder is provided. The method comprises identifying exons which exhibit an expression level that is at least within the $75^{th}$ percentile of exon expression levels within a nucleic acid-containing sample from a mammal having a neuropsychiatric disorder; comparing the sequence of each identified exon to the sequence of a corresponding exon from a healthy control to identify rare or de novo sequence mutations within the identified exon; calculating the burden of rare or de novo mutations within the exon; and determining the correlation between expression level of the identified exon and burden of de novo or rare mutations in the exon, wherein an inverse correlation indicates that the exon gene is linked to causality of the neuropsychiatric disorder.

8 Claims, 33 Drawing Sheets

Specification includes a Sequence Listing.

A.

B.

C.

A. Prenatal

B. Early Childhood

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tgacatcgca cgtccatctg          20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
acaggtagta aatggcccag g          21

<210> SEQ ID NO 3

-continued

```
<211> LENGTH: 20
<212> TYPE: DNA
<213> ORGANISM: Artificial Sequence
<220> FEATURE:
<223> OTHER INFORMATION: primer

<400> SEQUENCE: 3
gagccttcct gatcccctat                                                 20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
actgtttcca cggcagtgt                                                  19

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cggctgctgt gctatcattc                                                 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cagccaacac ccttccagat                                                 20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggctggataa gccaggtcag                                                 20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ggaaagagtt gtagctcccg a                                               21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
```
cctgttcttc cgtggagtga                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
catgaagccc acgatggaga                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ggctggataa gccaggtcag                                          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tactcatcca ccagggctgt                                          20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cctcaacaga cactgccgta                                          20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtctcccgcc gagtaagaag                                          20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
cctcatcccc atggtgacat c                                        21

<210> SEQ ID NO 16
<211> LENGTH: 20
<212> TYPE: DNA

```
<213> ORGANISM: Artificial Sequence
<220> FEATURE:
<223> OTHER INFORMATION: primer

<400> SEQUENCE: 16
ttactgcggt tgtgcaggag                                                    20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gactttgtct tcgccccaga                                                    20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ctaccatcaa gccgtccctg                                                    20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tccgacattc tcacttgcca                                                    20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ccagggtcag cacaagtcat                                                    20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ggactgttct ctgctgggac                                                    20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gttcggaacc agtactcgcc                                                    20
```

-continued

```
<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ccgcatcctg atgtgtctga                                                   20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ttgcaggtgg atacgtgact                                                   20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ttcatcccaa ttcaggagac                                                   20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
catgatccga atgtcacaaa                                                   20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
agcaggtttc tcactggtta                                                   20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gatgctgtca ttccaagagc                                                   20

<210> SEQ ID NO 29
<211> LENGTH: 20
<212> TYPE: DNA
<213> ORGANISM: Artificial Sequence
<220> FEATURE:
```

```
<223> OTHER INFORMATION: primer

<400> SEQUENCE: 29
gccttgactt atccgaattg                                                 20

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
acctcgtcat acacgtcca                                                  19

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
attgccgaca ggatgcaga                                                  19

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
gagtacttgc gctcaggagg a                                               21
```

METHOD OF DETERMINING DISEASE CAUSALITY OF GENOME MUTATIONS

FIELD OF THE INVENTION

The present invention relates generally to methods of identifying the significance of gene mutations, and more particularly, to a method of determining the disease causality associated with a genomic mutation.

BACKGROUND OF THE INVENTION

Rare genomic variants are being revealed as preponderant genetic risk factors for neuropsychiatric conditions such as Autism Spectrum Disorder (ASD). ASD exhibits extensive clinical and genetic heterogeneity with high heritability (37-90%); for ~20% of affected individuals, an underlying genetic alteration is attributed as the cause. Chromosomal abnormalities, copy number variations (CNVs), smaller insertion/deletions (indels), single nucleotide variations (SNVs) and combinations thereof, have been described in ASD. Indeed, >100 ASD susceptibility genes of variable (and still largely undetermined) penetrance and expressivity are known, with several hundred others estimated to exist. A similar genetic architecture is also starting to emerge in other brain disorders such as schizophrenia (SZ), intellectual disability (ID) and epilepsy, and some genes are implicated across these disorders.

Proving causality of a particular DNA sequence variant(s) in a complex disorder such as ASD can be complicated by the exceptional rarity of mutations involved (often unique to individuals or families), and the rate of new mutation, which is often equal in controls. For example, the rate of de novo SNV-indels is similar (~1 per exome) between ASD-affected and -unaffected individuals (population controls or unaffected siblings). Regarding CNVs, a slightly increased burden of de novo events has been observed in ASD cases compared to family and population controls, but these deletions and duplications usually affect multiple genes complicating attempts in simple genotype-phenotype correlations. Through genotyping massive cohorts, there has been some progress identifying critical exons for clinical manifestation of ASD in the NRXN, NRXN3 and UTS2 genes. However, a more robust approach is needed to find those rare etiologic alterations amongst thousands of other variants generated in genome scanning experiments.

SUMMARY OF THE INVENTION

It has now been determined that exons of genes harboring deleterious disease-related mutations were found to be significantly enriched and to exhibit an inverse relationship with burden of rare or de novo mutation in individuals having a disease condition such as a neuropsychiatric disorder.

Accordingly, in aspects of the present invention, a method of identifying one or more genes or genome sequence mutations linked to causality of disease is provided. The method comprises the steps of:

i) identifying exons which exhibit an expression level that is greater than the $75^{th}$ percentile of exon expression levels in nucleic acid from one or more individuals having a disease;

ii) comparing the sequence of each identified exon to the sequence of a corresponding exon from a healthy control to identify rare or de novo sequence mutations within the identified exon;

iii) calculating the burden of rare or de novo mutations within the exon; and iv) determining the correlation between expression level of the identified exon and burden of de novo or rare mutations in the exon, wherein an inverse correlation indicates that the exon gene and at least one of said sequence mutations is linked to causality of the disease.

A computer system for conducting a method to determine genes linked to causality of a disease, as well as a computer program product, comprising a tangible computer-readable medium carrying computer-usable instructions which, when executed by a processing unit of a computer, cause the processing unit to identify one or more genes linked to causality of a disease using the above method, are also provided.

In another aspect, a method of diagnosing a disease in a mammal is provided comprising the steps of:

i) identifying, using a processing device, mutant exons in a nucleic acid sample of the mammal comprising rare or de novo sequence mutations as compared to the sequence of corresponding exons from one or more healthy controls;

ii) comparing, using a processing device, mutant exons to critical exons associated with the disease identified using a method as defined in claim 1 to determine if the mutant exons are critical exons; and iii) optionally, if a mutant exon is determined to be a critical exon, then tissue type and protein network of the mutant exon is determined and compared to that of the critical exon, wherein the mammal is determined to have the disease when the mutant exon has the same tissue type and protein network of the critical exon.

A computer system for conducting a method of disease diagnosis is also provided, as well as a computer program product, comprising a tangible computer-readable medium carrying computer-usable instructions which, when executed by a processing unit of a computer, cause the processing unit to diagnose disease using the above method.

These and other aspects of the invention will be described in the detailed description by reference to the following figures.

BRIEF DESCRIPTION OF THE FIGURES

FIG. 10. Classifying missense/LOF exons with de novo mutations in ASD proband and unaffected siblings: (D) box plots show the percentages of de novo mutations (for cases and unaffected siblings) that can be classified as critical exons (left) or tolerated exons (right) using all transcriptome samples. Each confidence interval represents the fraction of variability in the number of critical or tolerated exons obtained from different transcriptome samples (interquartile range (IQR) is between the first and third quartiles). (E) Applying 75th percentile cutoff on the transcriptome/mutation contingency index, we have computed the fraction of LOF that can be classified as 'critical' and 'tolerated' exons using all transcriptome samples. The confidence interval represents the fraction variability of 'critical' or 'tolerated' exons obtained from different transcriptome samples.

Figure 14:
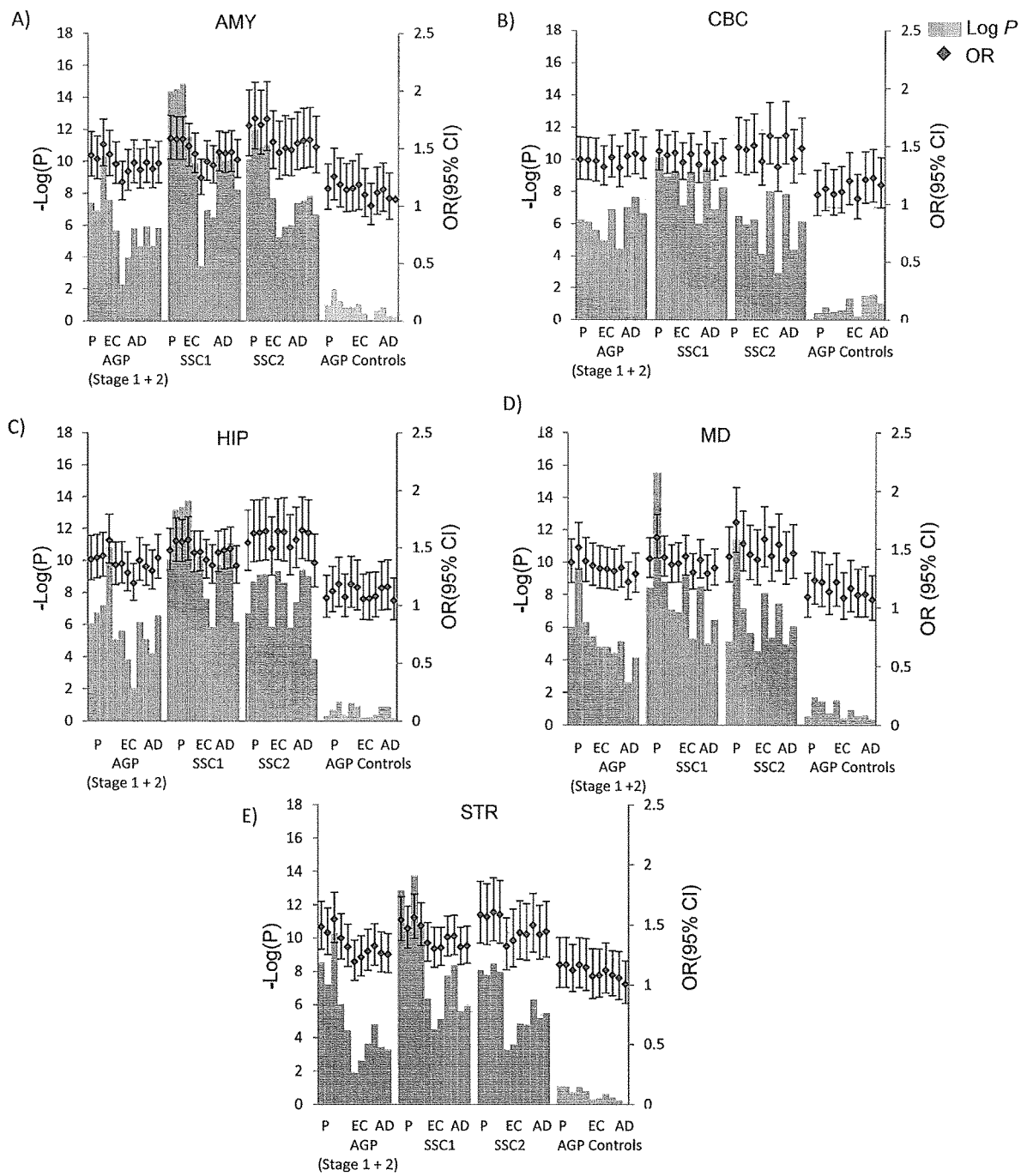

FIG. 14. Association of exon transcriptome and rare missense mutation burden using spatio-temporal expression for genes within de novo CNVs ascertained in ASD probands or controls. De novo losses/gains comprehensively ascertained in four earlier studies of ASD (AGP (stage 1 and 2), SSC1 and SSC2) were assayed in data from 16 brain regions of postmortem donors from three developmental periods (prenatal (P), early childhood (EC), and adult (AD)). The analysis plotted for 196 developing human brain samples (P-prenatal, E-early childhood, and A-adult) includes 11 neocortex (NCX) regions (FIG. 4A), (A) amygdala (AMY), (B) cerebellar cortex (CBC), (C) hippocampus (HIP), (D) mediodorsal nucleus of the thalamus (MD) and (E) striatum (STR).

Figure 15:
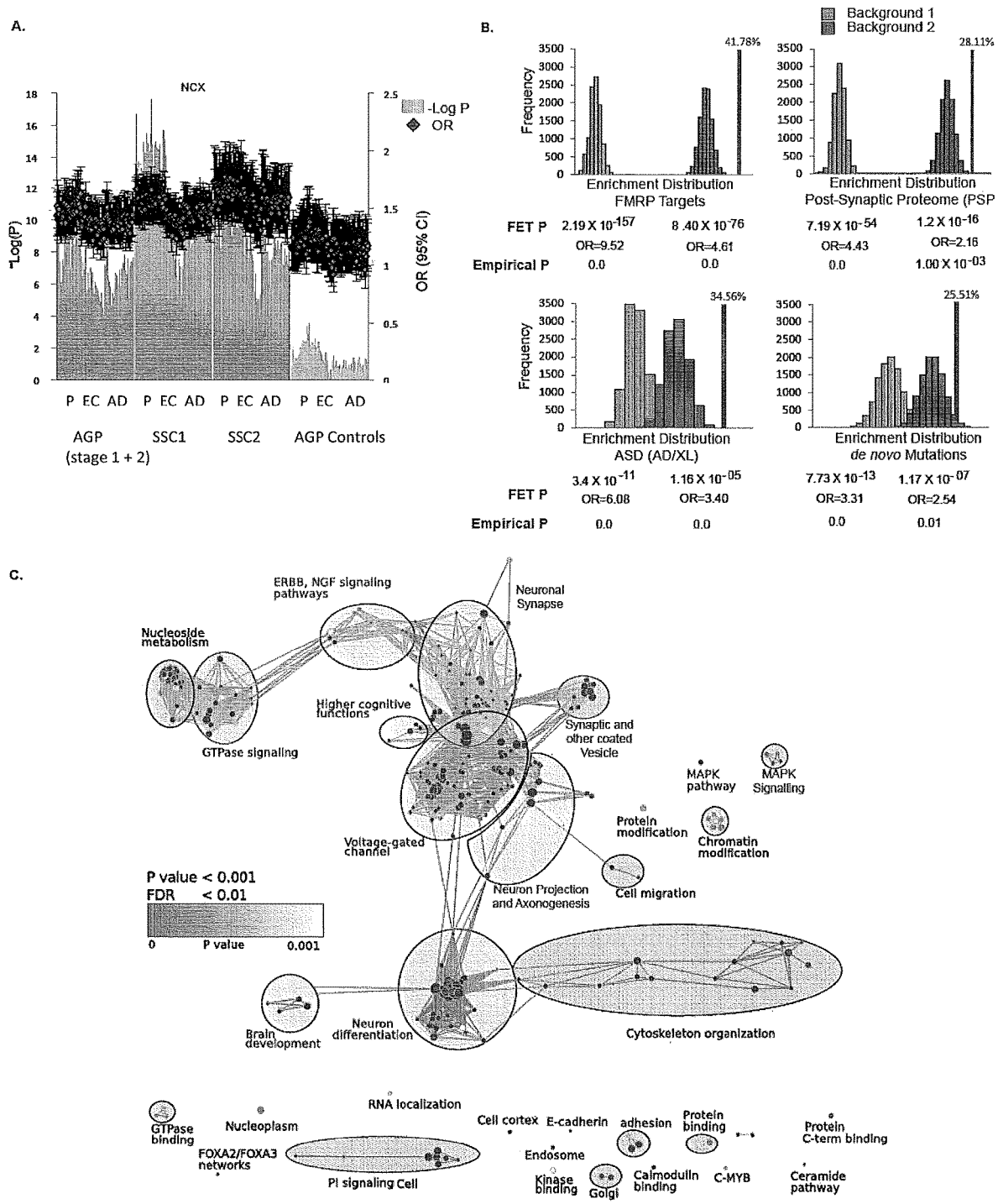

FIG. 15. Delineation and profiling of brain specific critical exons. (A) Association analysis of spatio-temporal expression for genes within de novo CNVs ascertained in four earlier studies of ASD (AGP (stage 1 and 2), SSC1 and SSC2) were assayed in data from 16 brain regions of postmortem donors from three developmental periods (prenatal (P), early childhood (EC), and adult (AD)). The plot shows spatio-temporal association results between exon expression level (11 neocortex regions) and burden of rare missense mutations for genes within de novo CNVs reported in ASD Probands and in controls (see FIG. 14 for amygdala, cerebellar cortex, hippocampus, mediodorsal nucleus of thalamus, and striatum transcriptome association results and RNA-Seq validation). (B) Brain specific 'critical exon' enrichment analysis on FMRP targets, PSP, ASD (autosomal dominant, X-linked (XL)) and genes with de novo mutations represented by the vertical line and the p-values (FET; Benjamini Hochberg corrected) relative to the two corresponding backgrounds (entire RefSeq exons set (background 1) and highly brain expressed exons (background 2)). The empirical p-value was obtained from the permutation test for each background (10,000 random draw of equal number of exons). (C) A functional map of brain specific 'critical exons' by mapping enrichment significance as a network of gene sets (nodes), where edges represent mutual overlap between gene sets. The size of the node is proportional to the number of genes in each gene set, and the node color represents the significance (p-value) of overlap. Nodes that are functionally interconnected are similarly circled (implicated in previous ASD networks) into one major group and labeled with their corresponding function.

Figure 16:
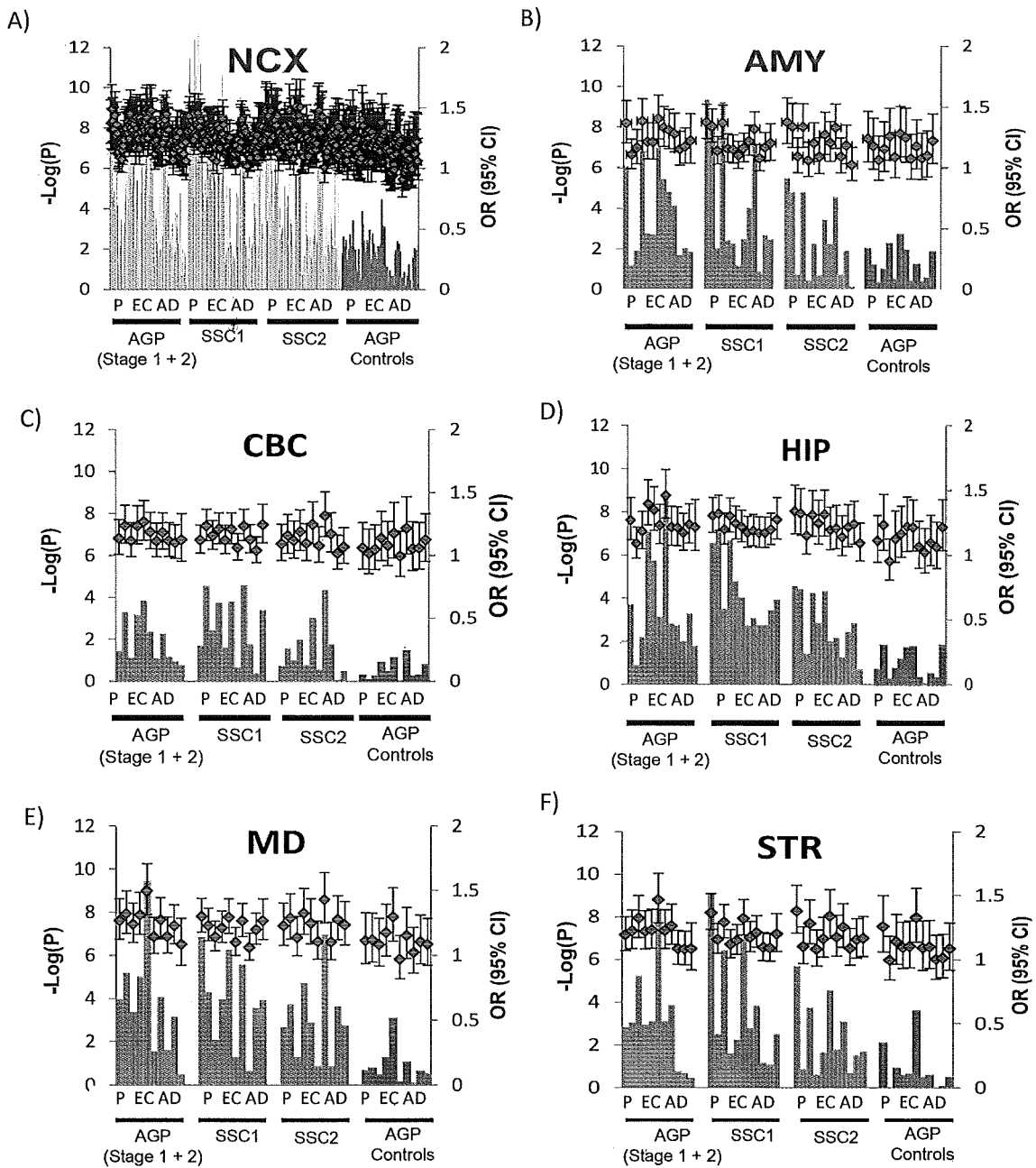

FIG. 16. The RNA-seq validation for genes within de novo CNVs ascertained in ASD probands or controls. Applying $75^{th}$ percentile cutoff (similar to microarray), the association significance (FET; left y-axis $-\log(P)$) for three developmental periods (prenatal (P), early childhood (EC), and adult (AD)) on 196 human brain samples from (A) amygdala (AMY), (B) cerebellar cortex (CBC), (C) hippocampus (HIP), (D) mediodorsal nucleus of the thalamus (MD) and (E) striatum (STR). Bars illustrate $-\log(P)$ for genes within rare CNVs ascertained in AGP stage 1 and 2 controls. Similar to microarray, from RNA-seq analysis we observed the strongest association in neocortex from prenatal samples (FET, Bonferroni corrected, $p<3.13\times10^{-11}$; OR=1.45).

Figure 17:
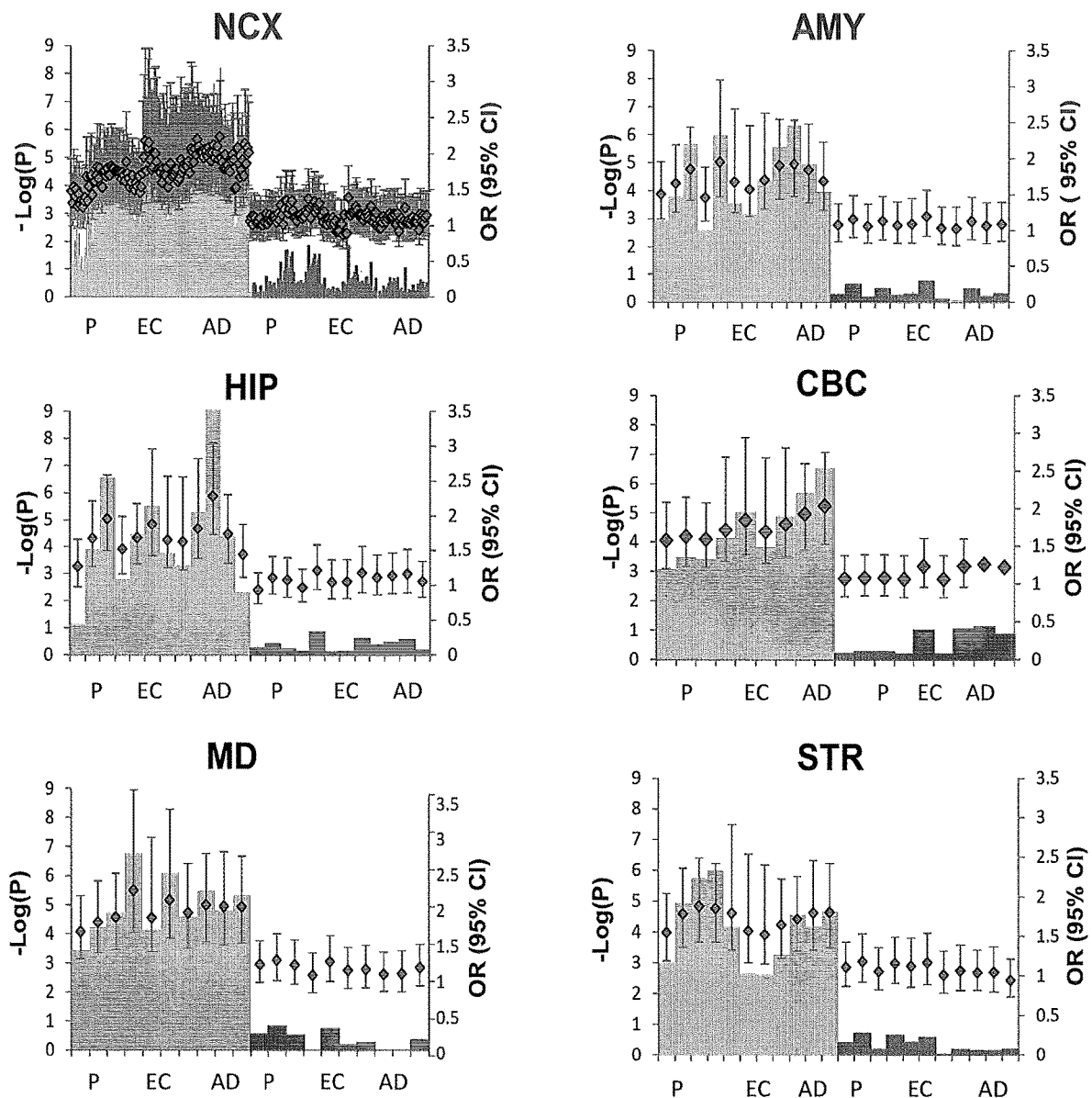

FIG. 17. de novo/rare single genic losses reported in AGP stage 1 and 2 and their association analysis. Spatio-temporal microarray analysis using human developmental brain for de novo/rare (<0.01 frequency) single gene losses (impacting coding sequence) exclusively identified in probands or controls. Significance with higher odds ratio (OR) was observed within genes ascertained for probands in prenatal neocortex samples (A) amygdala (AMY), (B) cerebellar cortex (CBC), (C) hippocampus (HIP), (D) mediodorsal nucleus of the thalamus (MD) and (E) striatum (STR).

Figure 18:
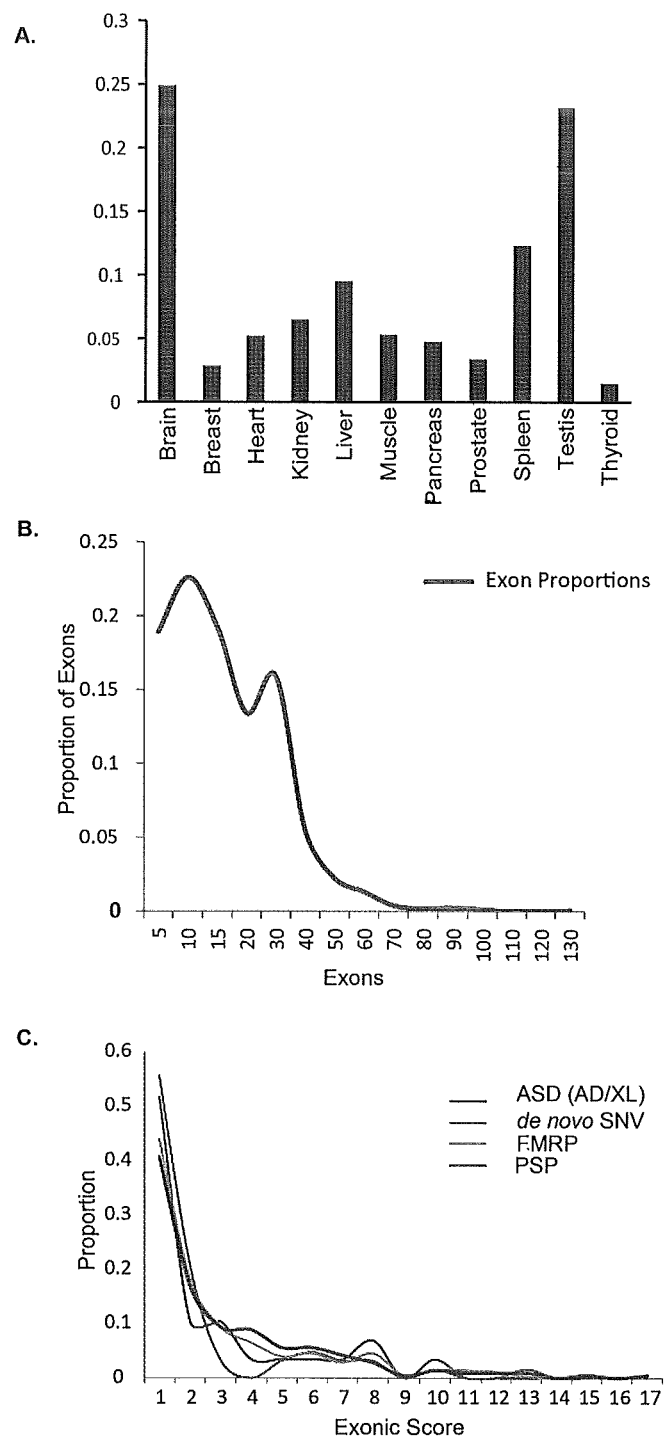

FIG. 18. Tissue-specific 'critical exons'. (A) Relative proportion of tissue-specific critical exons detected from 11 tissues. (B) Exon density distribution for genes containing 'brain-critical exons'. (C) Genes were scored based on the number of exons relative to mean number of tissue specific critical exons in the list. The plot shows exonic scores for the genes reported in –ASD (AD and X-linked), de novo SNVs, FMRP targets, and PSP.

Figure 19:
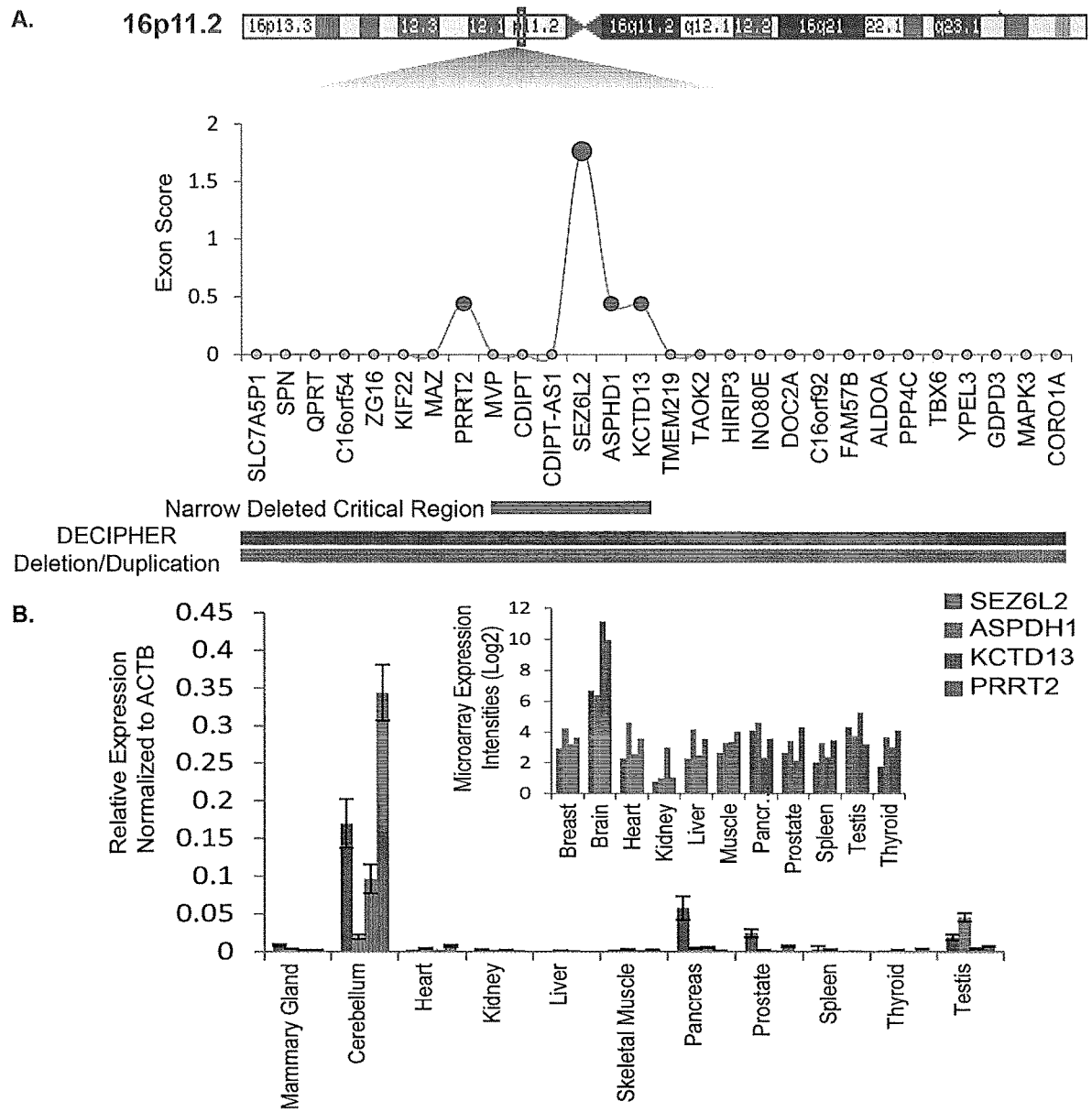

FIG. 19. Overlap of 'brain-critical exons' within the 16p11.2 deletion locus. (A) Overlapping 'brain-critical exons' for genes within the 16p11.2 locus and their corresponding exon score is plotted. The horizontal bars represent the recurrent breakpoint reported in DECIPHER database, the narrow critical region captured in a multiplex family with similar phenotypes. (B) Relative expression ($2^{(-dCt)}$) from quantitative real-time PCR (qRT-PCR) relative to ACTB (replicated with another housekeeping gene MED13) shows brain (adult cerebellum) specific higher expression of the identified 'brain-critical exons' in SEZ6L2, ASPDH1, KCTD13, and PRRT2 within 11 different tissues, consistent with microarray expression intensities.

Figure 20:
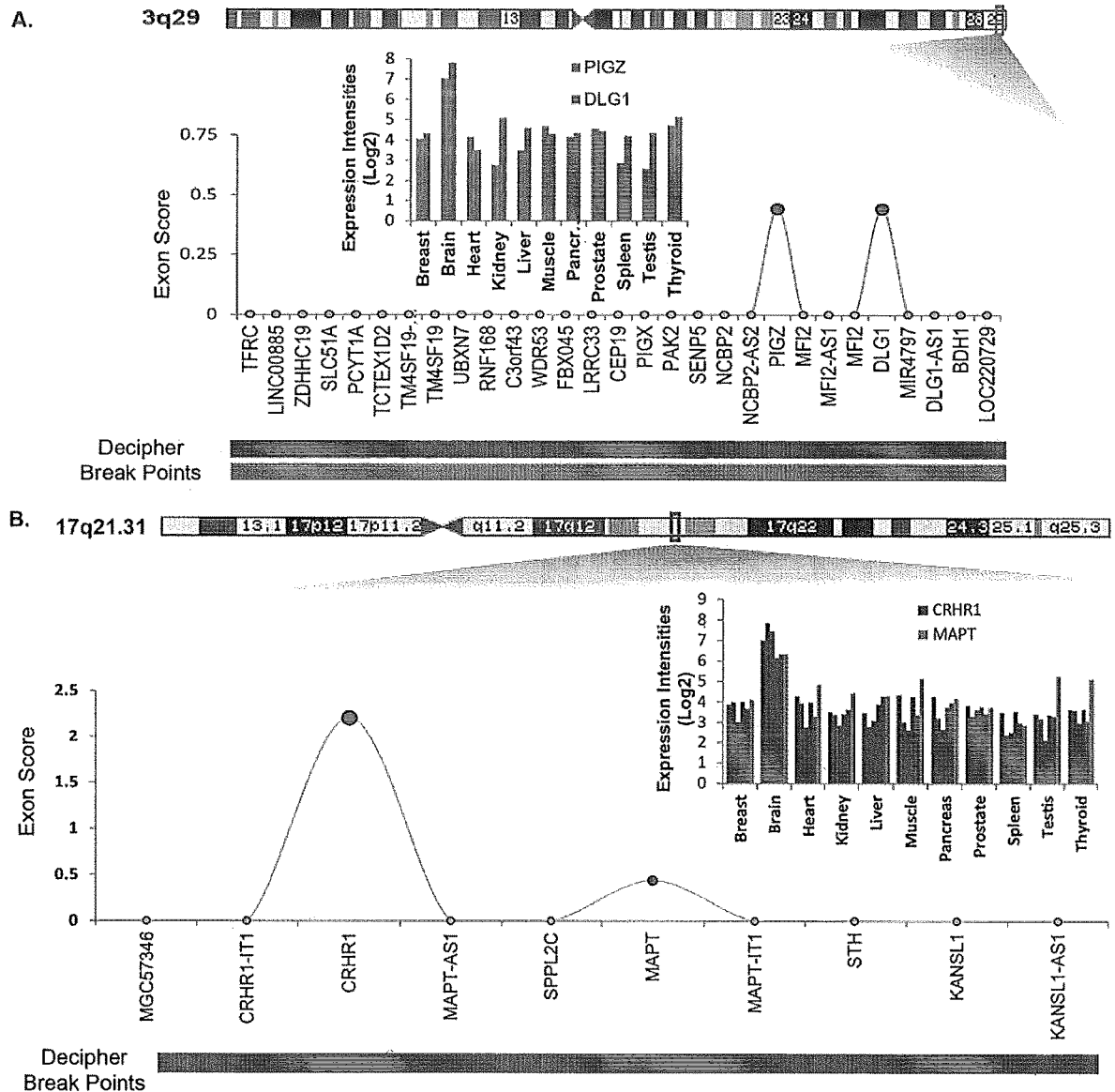

FIG. 20. Genes from 3q29 and 17q21.31 loci containing 'brain-critical exons', and their expression profile from multiple tissues. (A) Within 3q29, recurrent micro-duplication/deletions are associated with syndromes. Genes containing critical exons from this locus are: discs large homolog 1 (DLG1) and phosphatidylinositol glycan anchor biosynthesis, class Z (PIGZ). DLG1 is an ASD candidate gene within the locus and independent reports are emerging to establish DLG1 as a primary candidate gene for 3q29 micro duplication/deletion syndrome. There is also emerging evidence for the potential role of DLG1-4 in cognition and psychiatric disorder from mouse knockouts. A recent study on PIGZ knockout mouse experiment showed a significant increase of amyloid-β (Aβ) peptide (a molecule with pathological role for Alzheimer's disease). (B) Multiple brain specific critical exons (5 exons) within corticotropin-releasing hormone receptor 1 (CRHR1) gene and microtubule-associated protein tau (MAPT) gene were detected within 17q21.31 deletion locus. Multiple lines of evidence suggest the role of corticotropin-releasing hormone receptor 1 (CRHR1) on neuropsychiatric disorders. MAPT is also a well-studied candidate gene for neuropsychiatric disorders.

Figure 21:
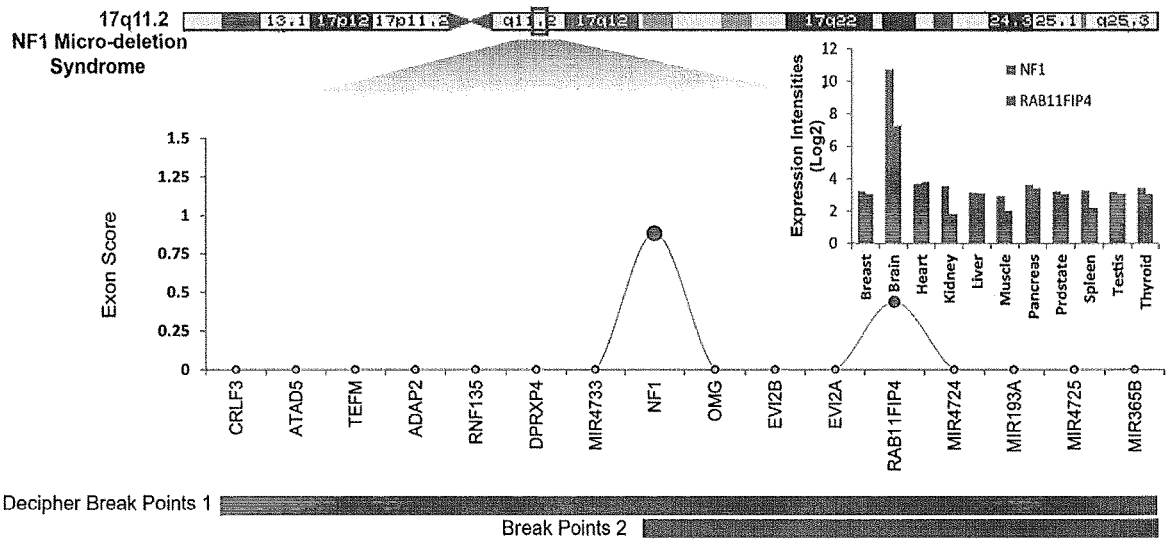
Figure 21:
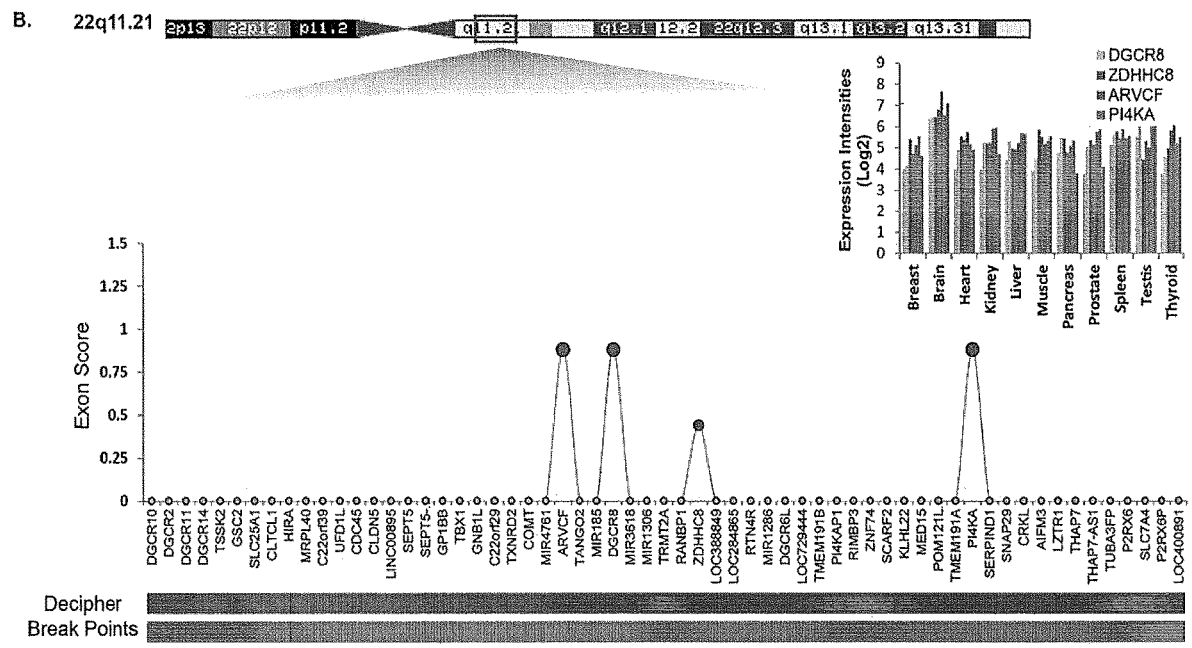

FIG. 21. Genes for neurofibromatosis 1 (NF1) microdeletion syndrome and 22q11.21 loci containing 'brain-critical exons' and their expression from multiple tissues. (A) The NF1 micro-deletion syndrome involves two primary breakpoints with variable phenotypes. Both breakpoints affect coding sequence of NF1 and RAB11 family interacting protein 4 (RAB11FIP4) genes and the cases also have intellectual disability as a common phenotypic manifestation. NF1 is reported to be the primary candidate gene in the locus by multiple studies and in addition RAB11FIP4 shown to be a candidate gene from gene expression analysis. (B) Within the 22q11.21 locus, four genes (armadillo repeat gene deleted in velocardiofacial syndrome (ARVCF), DGCR8 microprocessor complex subunit (DGCR8), zinc finger, DHHC-type containing 8 (ZDHHC8) and phosphatidylinositol 4-kinase, catalytic, alpha (PI4KA)) were found to have 'brain-critical exons'. All four genes within these loci implicated previously in multiple neuropsychiatric phenotype studies. ARVCF, DGCR8, ZDHHC8 are the three well documented candidate genes.

Figure 22:
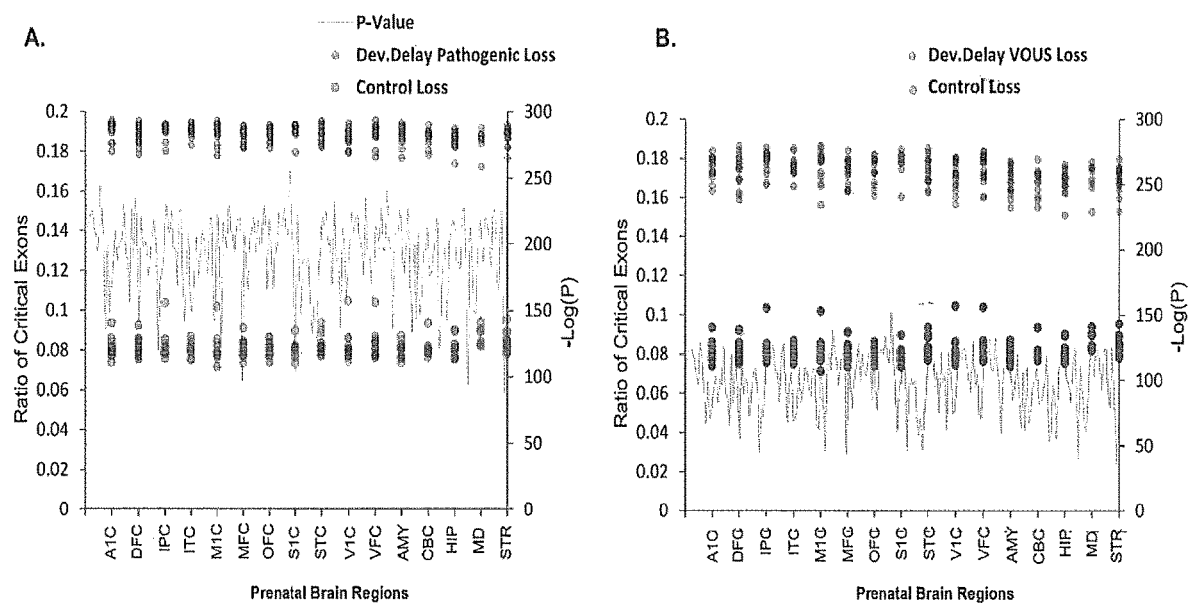

FIG. 22 illustrates critical-exon enrichment analysis of prenatal pathogenic (A), VOUS (B) and control samples from individuals with developmental delay.

Figure 23:
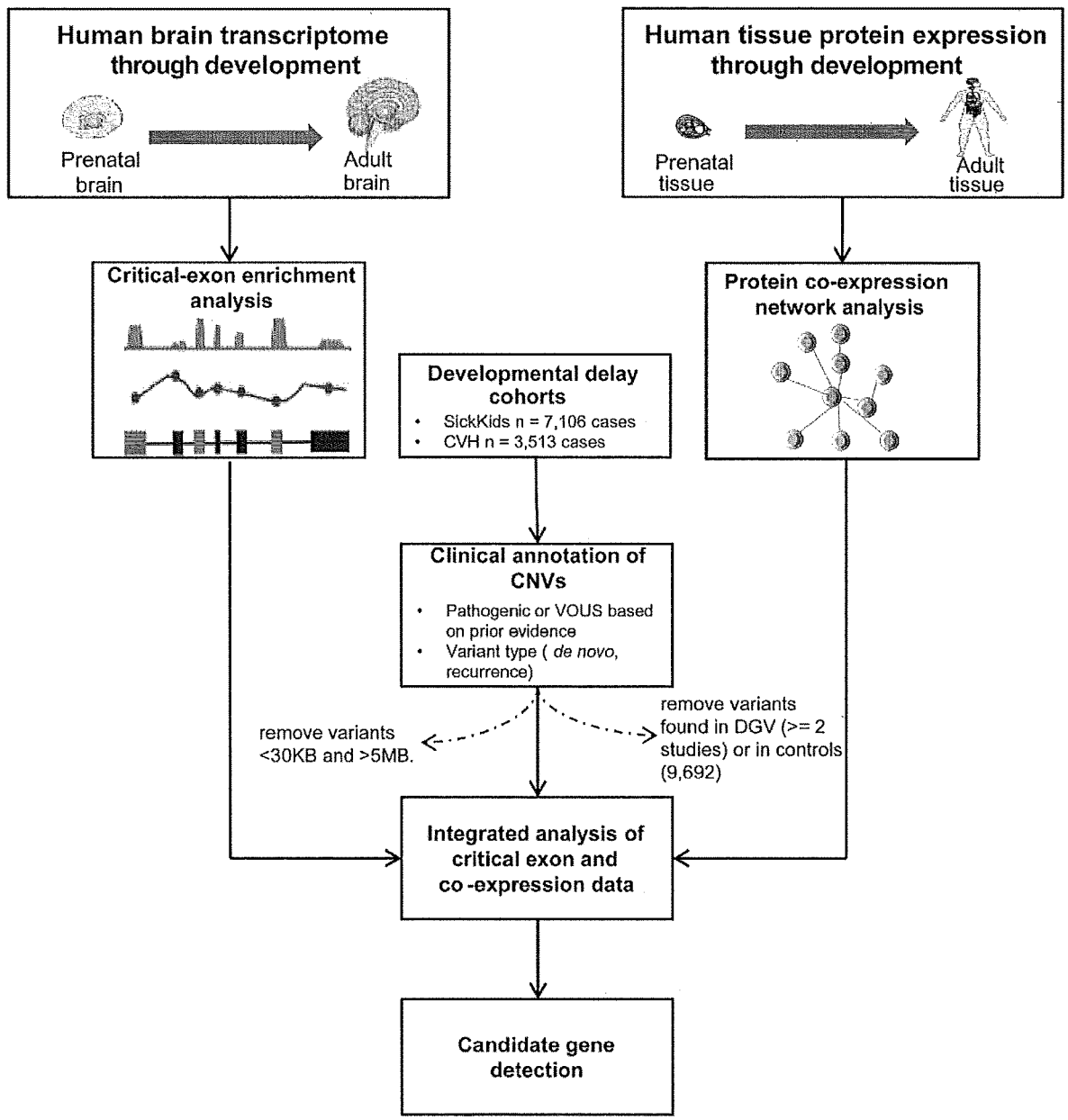

FIG. 23 illustrates a schematic of the analysis framework using genome-wide human (prenatal and adult) brain transcriptome (RNA sequencing) and proteome (Fourier-transform mass spectrometry) data to identify candidate genes from copy number variation in developmental delay.

Figure 24:
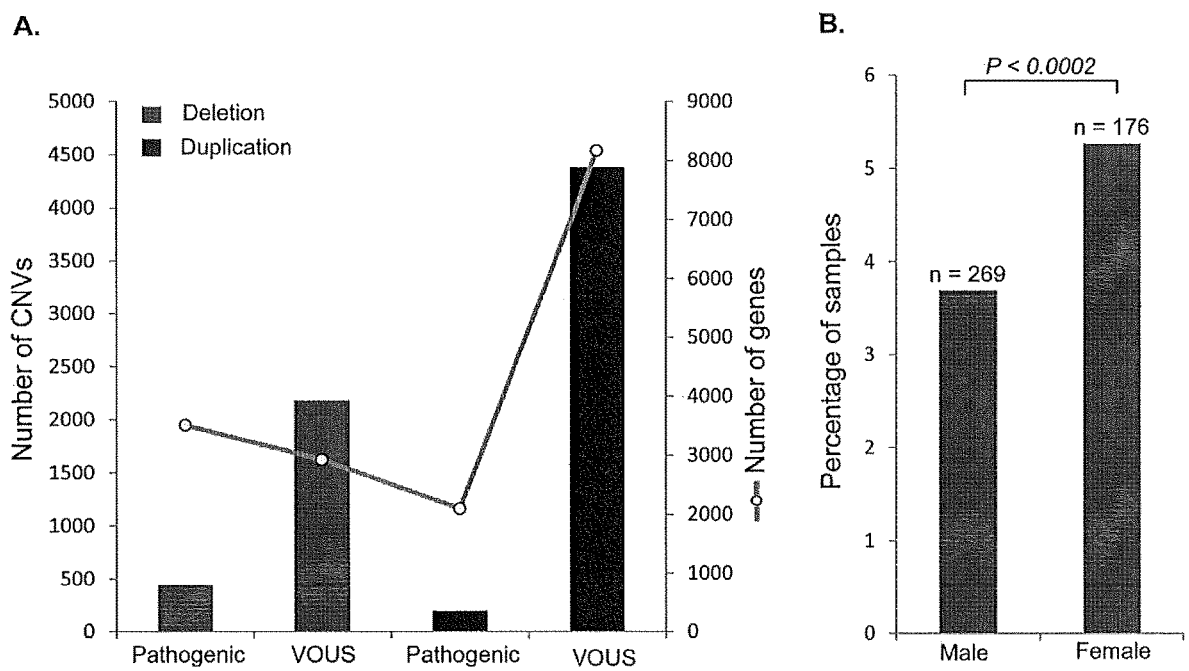

FIG. 24. Ascertainment of pathogenic variants or variants of uncertain significance (VOUS) in 10,619 developmental delay cases. The rare CNVs of 30 kb to 5 Mb were classified as pathogenic or variant of uncertain significance (VOUS). (A) Bars indicate the total number of CNVs in each classification (deletion in red and duplication in blue). Relative to all samples assayed, 4.19% and 1.81% of all samples tested carry a pathogenic deletion and duplication, respectively; whereas, 18.28% and 31.97% of samples carry a VOUS deletion and duplication, respectively. The green line represents the number of unique genes impacted by the corresponding variants. (B) The percentage of male and female cases in the cohort impacted by pathogenic deletion variants. P value shown is for the one-sided Fisher's exact test.

Figure 25:
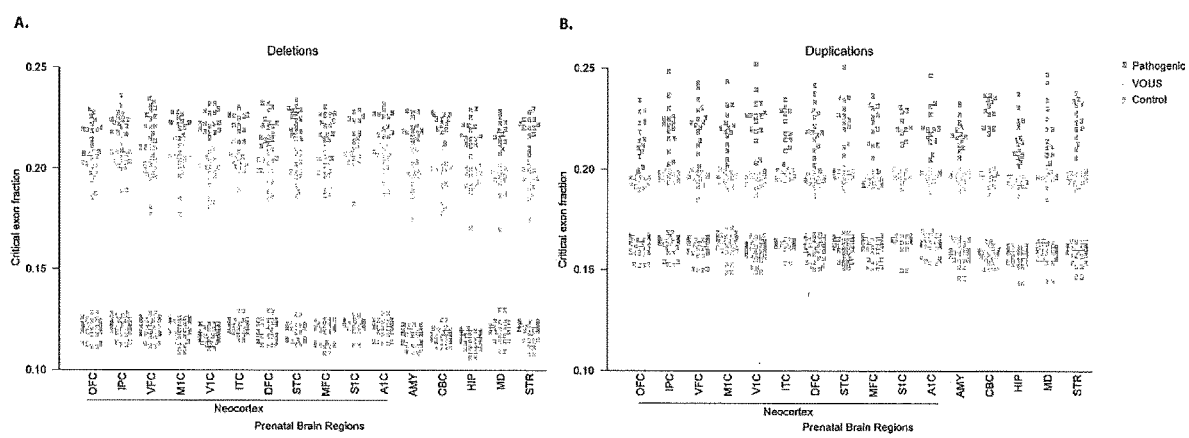

FIG. 25. The fraction of critical exons (over all exons) computed from human prenatal brain regions for the genes impacted by pathogenic, VOUS and rare control deletion and duplication variants. The critical exon fraction was computed using gene expression level quantified from RNA sequencing in 392 brain tissues (controls) from 31 postmortem donors in 2 developmental periods (prenatal and adult) for 16 brain regions (AMY, amygdaloid complex; CBC, cerebellar cortex; V1C, primary visual cortex; STC, posterior (caudal) superior temporal cortex; IPC, posterior inferior parietal cortex; A1C, primary auditory cortex; S1C, primary somatosensory cortex; M1C, primary motor cortex; STR, striatum; DFC, dorsolateral prefrontal cortex; MFC, medial prefrontal cortex; VFC, ventrolateral prefrontal cortex; OFC, orbital frontal cortex; MD, mediodorsal nucleus of thalamus; ITC, inferolateral temporal cortex; HIP, hippocampus). The critical exon fraction computed using prenatal brain transcriptome is shown for the genes impacted by pathogenic (red dots) and VOUS (orange dots) (A) deletions and (B) duplications in comparison to genes impacted by rare control deletions (gray dots).

Figure 26:
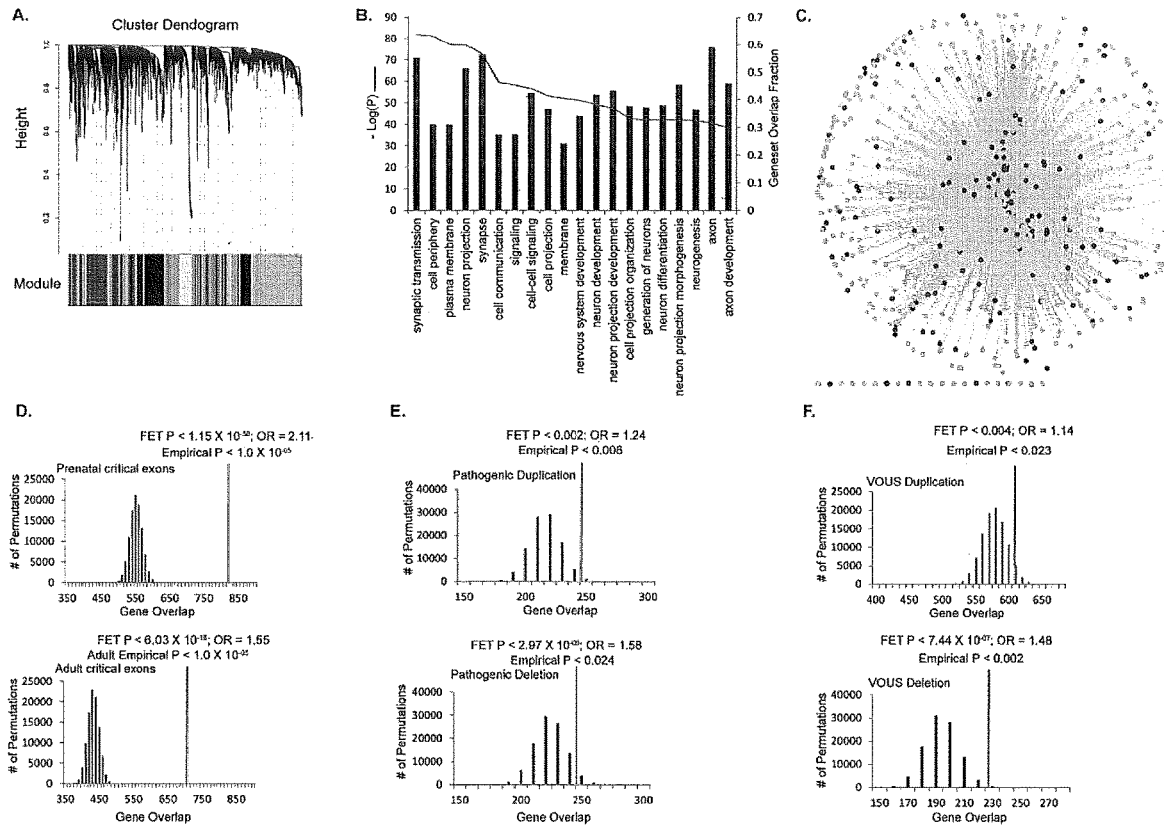

FIG. 26. Genome-wide protein co-expression and enrichment of genes ascertained from pathogenic and VOUS CNVs using human prenatal and adult tissues. (A) The protein modules generated by weighted gene coexpression network analysis (WGCNA) using high resolution genome-wide Fourier-transform mass spectrometry data from 30 histologically normal human samples (prenatal and adult). Each coloured bar (dispersed) represents a module. (B) For the blue module, the 20 most significant results from quantitative association with 18,826 gene sets. (C) Representation of the 'blue' module as a functional network, where each node is a gene; the edge between genes represents the weighted Pearson distance. Red nodes represent genes ascertained through CNVs in the developmental delay cohort. (D) The top (25th percentile) critical exon genes in the genome ascertained using prenatal (green) and adult brain (purple) transcriptomes, and their corresponding quantified enrichment in the protein module, through Fisher's exact test (FET) and 100,000 permutations. The orange bar represents the original observation of overlaps between blue module and a gene set. Similarly, (E) and (F) show the enrichment of genes impacted by pathogenic and VOUS duplications (blue) and deletions (red) within the protein module.

Figure 27:
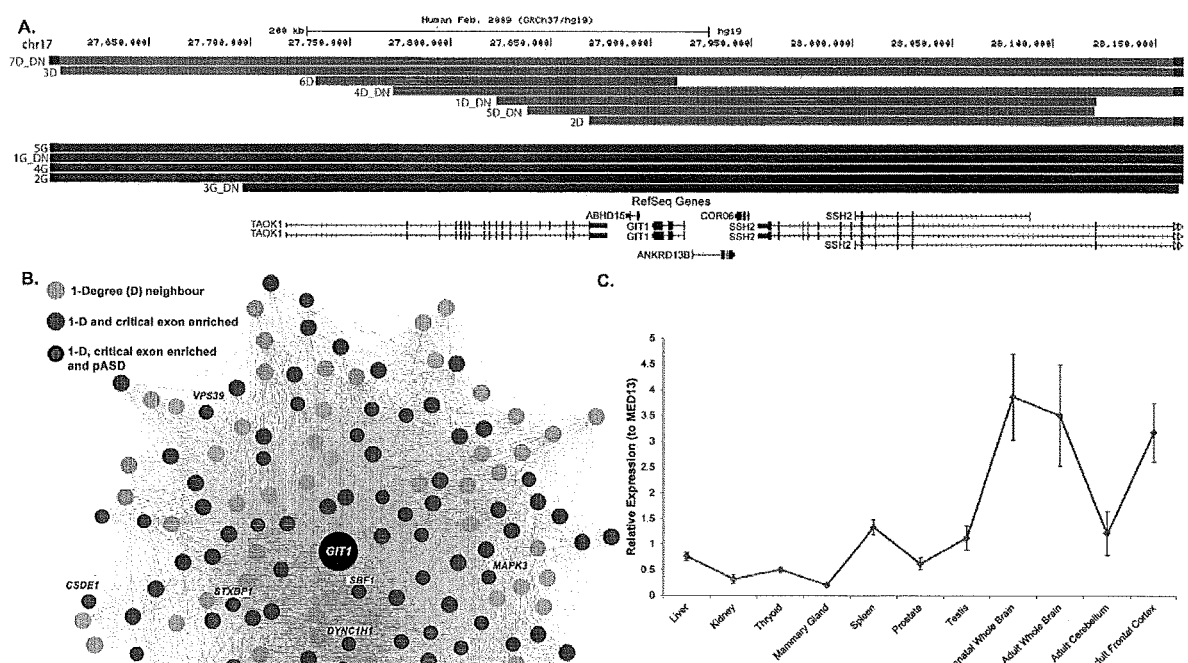

FIG. 27. Deletions within the GIT1 gene identified in developmental disorder cases or controls. (A) The breakpoints of 12 VOUS deletions (red) and duplications (blue) impacting GIT1 and nearby genes. The dataset includes 5 de novo deletions/duplications (denoted as DN) reported from developmental cases; no rare CNV was found in controls. (B) The analysis of the human protein co-expression network revealed that GIT1 is within the blue module and is highly connected (1-degree neighbors) with genes enriched for 'critical exons' (red nodes) and putative ASD genes reported to have de novo mutations (red node with black outline). (C) Expression of GIT1 (primer targeting critical exons) from quantitative real-time PCR (qRT-PCR) relative to housekeeping gene, MED13 (replicated with another housekeeping gene ACTB) in 11 different tissues.

Figure 28:
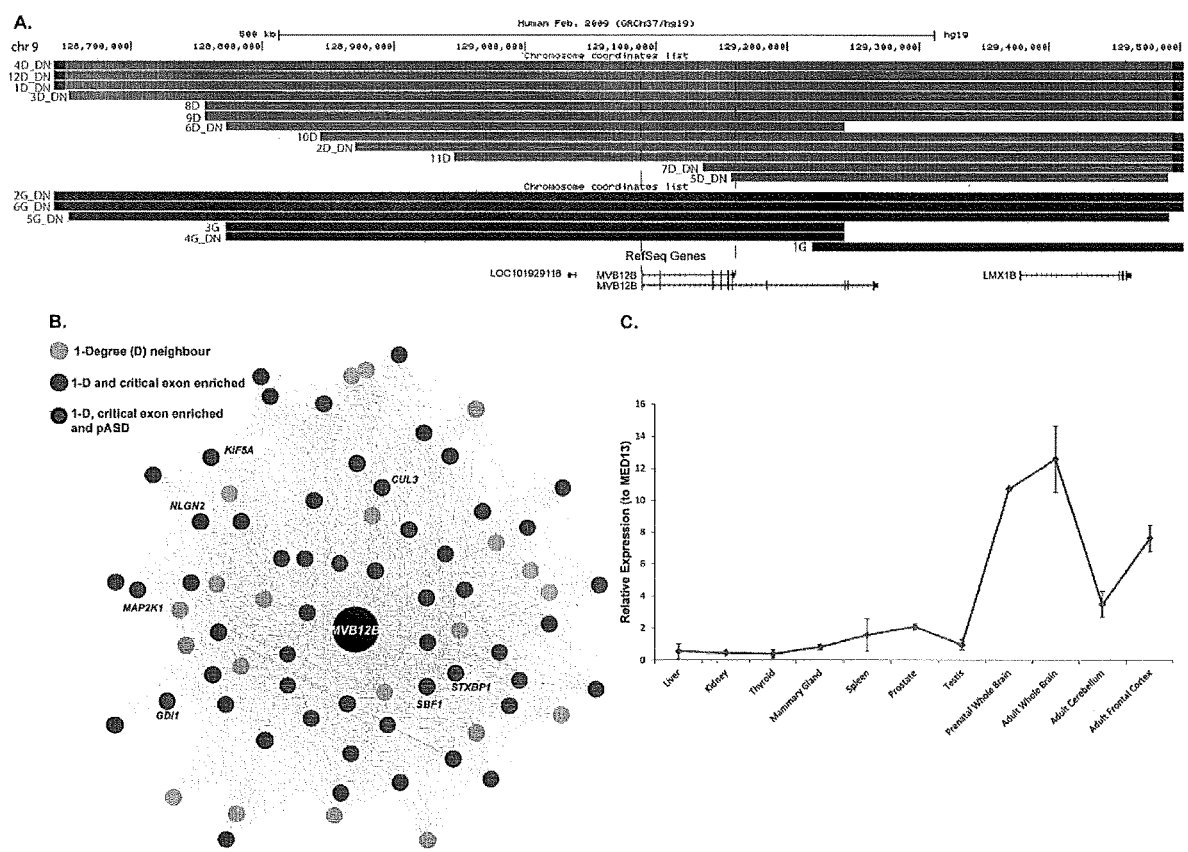

FIG. 28. Deletions within MVB12B gene identified in developmental disorder cases and controls. (A) The breakpoints of 18 VOUS deletions (red) and duplications (blue) impacting MVB12B and nearby genes. The breakpoints include 12 de novo VOUS reported from developmental delay cases, including 3 recurrent breakpoints (6D-DN, 4G-DN, 3G). All de novo VOUS impact the smaller isoform (highlighted by dash line) of the gene (NM_001011703.2) which is not impacted by CNV in controls. (B) The human protein co-expression network revealed that the MBV12B gene is the within the blue protein module and enriched for 'critical exons' (red nodes) and putative ASD genes reported to have de novo mutations (red node with black outline). (C) Expression of MVB12B (primer targeting critical exons) from quantitative real-time PCR (qRT-PCR) relative to housekeeping gene, MED13 (replicated with another housekeeping gene ACTB) in 11 different tissues.

Figure 29:
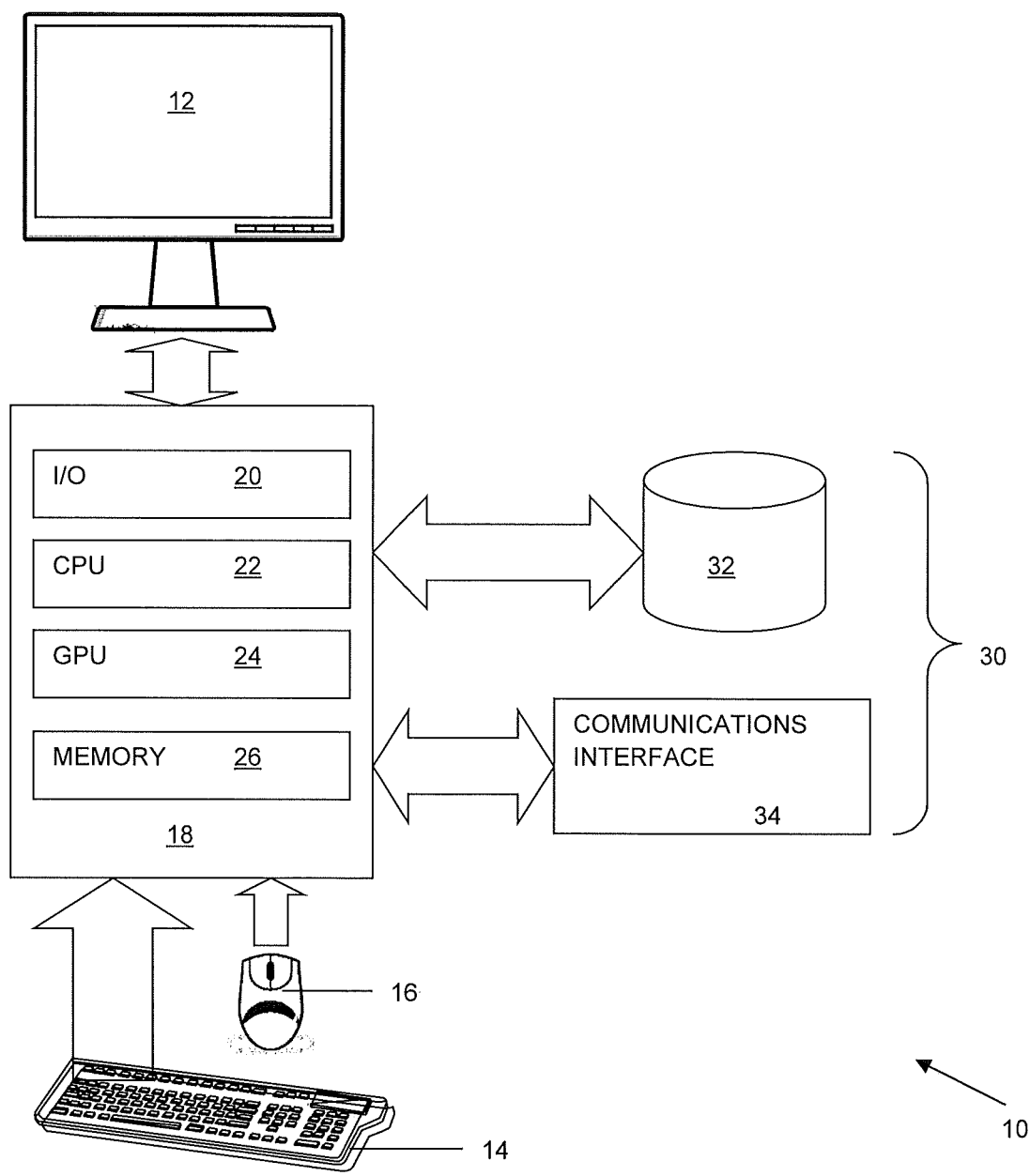

FIG. 29 is a block diagram illustrating a processing system suitable for use in aspects of the invention.

Figure 30A:
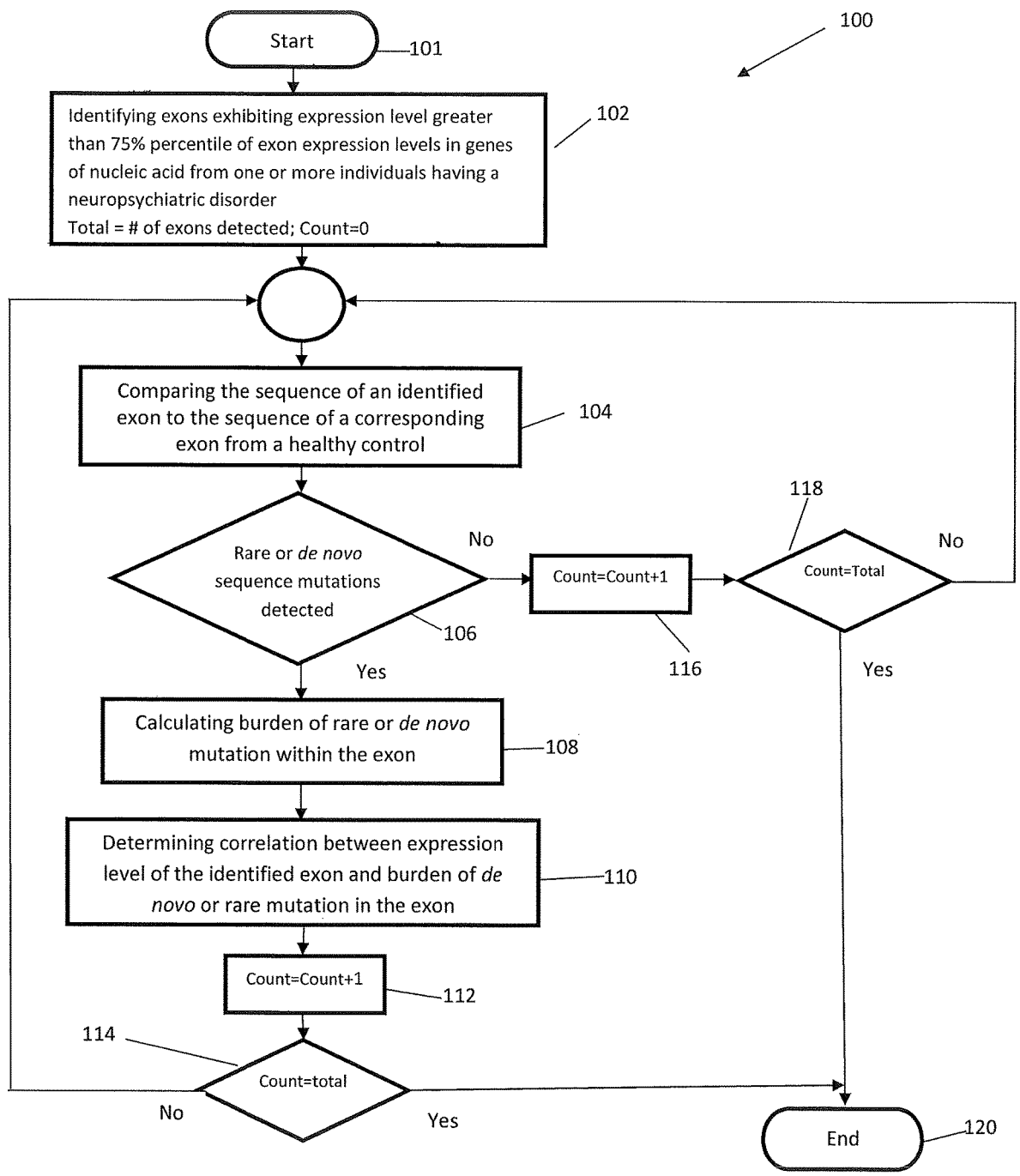

FIG. 30A is a block diagram illustrating a process for identifying one or more genes linked to causality of a disease, according to an embodiment of the invention.

Figure 30B:
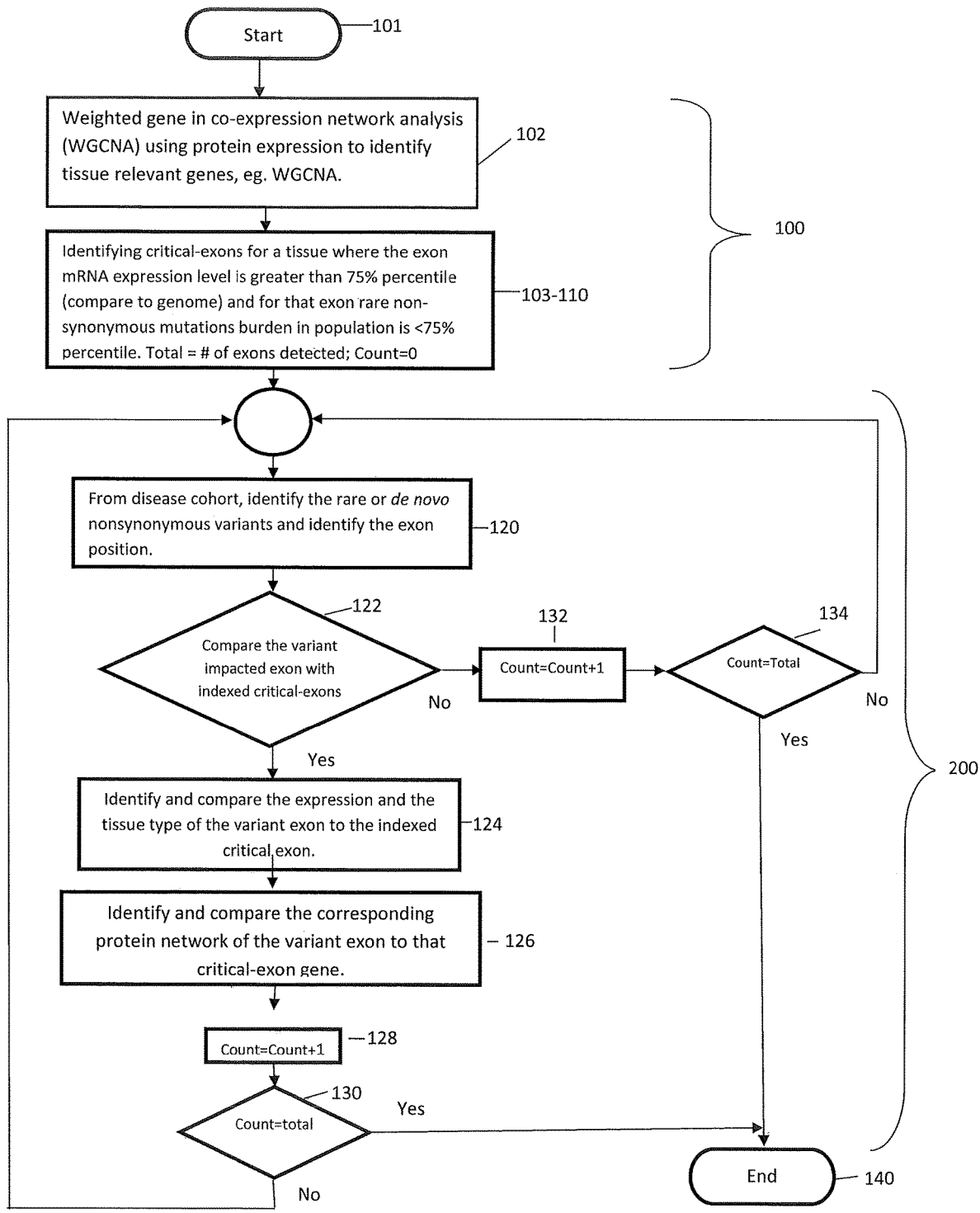

FIG. 30B is a block diagram illustrating a process for identifying disease in a disease cohort, according to an embodiment of the invention.

DETAILED DESCRIPTION OF THE INVENTION

A method of identifying a gene or genomic mutation that is linked to causality of a disease is provided. The method comprises identifying exons which exhibit an expression level that is greater than the $75^{th}$ percentile (third quartile) of exon expression levels in nucleic acid from one or more individuals having the disease; comparing the sequence of each identified exon to the sequence of a corresponding exon from a healthy control to identify rare or de novo sequence mutations within the identified exon; calculating the burden of rare or de novo mutations within the exon; and determining the correlation between expression level of the identified exon and burden of de novo or rare mutations in the exon, wherein an inverse correlation indicates that the exon gene is linked to causality of the disease.

The term "disease" is used herein to refer to a pathological condition in a mammal, including human and non-human mammals. The disease may, for example, be a pathological condition in a developmental process of the central nervous system and brain, heart, kidney, or other organs. Examples of disease conditions thus include, but are not limited to, neurological disease such as neuropathies and neuropsychiatric disorders, cardiomyopathy including congenital heart disease, cancers, diabetes, and developmental disorders.

The term "neuropsychiatric disorder" is used herein to encompass Autism Spectrum Disorder (ASD), i.e. a disorder that results in developmental delay of an individual such as autism, Asperger's Disorder, Childhood Disintegrative Disorder, Pervasive Developmental Disorder—Not Otherwise Specified (PDD-NOS) and Rett Syndrome (APA DSM-IV 2000); schizophrenia (SZ), intellectual disability (ID), Fragile X syndrome, epilepsy and related nervous system disorders such as OMIM (Online Mendelian Inheritance in Man) nervous system disorders.

In the present method, nucleic acid from one or more individuals, e.g. humans, having a disease of interest, a nucleic acid sample set, is studied and compared to corresponding nucleic acid control samples, i.e. nucleic acid samples from healthy individuals that do not have the disease. Nucleic acid from various biological samples may be studied, depending on the disease of interest, for example, samples from cerebellum, breast, heart, liver, muscle, kidney, thyroid, pancreas, prostate, spleen, and testis. For neurological disease, including neuropsychiatric disorders, preferred biological samples include brain samples, for example, neocortex, amygdala, cerebellar cortex, hippocampus, mediodorsal nucleus of the thalamus, and striatum. For cardiomyopathy, nucleic acid from the heart and related tissue is preferred. The samples may be obtained from any age group, including prenatal, child and adult samples.

The method comprises identifying exons within nucleic acid from one or more individuals (that have a selected disease, e.g. a neuropsychiatric disorder) that exhibit a high expression level relative to the expression of other exons within the sample, i.e. a high expression level is considered to be a level that is greater than the $75^{th}$ percentile of exon expression levels of all exons within the nucleic acid sample or data set. Such exon identification is conducted using methods well-established in the art, and will employ automated computerized methods.

Rare or de novo sequence mutations within exons exhibiting a high expression level are then identified by sequence comparison with corresponding control exon sequence, e.g. the nucleic acid sequence of a corresponding exon from a healthy control mammal that does not have the disease of interest. Such sequence comparison is conducted using methods well-established in the art, and will employ automated computer sequence comparison. Sequence mutations may include missense, frameshift, nonsense, splice-site variants and copy number variations (CNVs). "Rare" mutations are those which occur at a frequency of less than 0.05. A mutation not possessed by either parent of a sample being analyzed is considered to be a "de novo" mutation.

Once rare and de novo mutations within a given exon are identified, the burden of rare and de novo mutations within the exon is calculated. Mutation burden is defined as the mutation count, e.g. of rare and de novo mutations, divided by the length of the exon. Low mutation burden is considered to be a mutation burden that is less than the $75^{th}$ percentile of a given sample or dataset.

The correlation between expression level of an exon that exhibits a high expression level, i.e. an expression level greater than the $75^{th}$ percentile of exon expression levels in the sample, and burden of rare and de novo mutations within the exon is then calculated. An inverse correlation between exon expression level and mutation burden indicates that at least one of the rare or de novo mutations is linked to causality of the disease. It also provides an indication that the gene in which the subject exon exists is linked to causality of the disease. Further analysis may be conducted to determine the mutation that is linked to causality of the disease. Such calculations (mutation burden and correlation) and analyses will employ automated computerized methods.

In one embodiment, to determine a list of candidate genes for analysis, e.g. candidate genes related to a given disease or condition, a gene co-expression analysis may be conducted based on the proteome and enriched for genes encoding proteins relevant to the disease, for example, a gene co-expression analysis of genes related to developmental delay may be conducted in the determination of causality of a neuropsychiatric disorder. Genes which are identified to exhibit co-expression above a threshold expression, and which exhibit an inverse correlation between expression level and mutation burden are linked to causality of a given disease, such as a neuropsychiatric disorder. In this regard, a gene was deemed to be significant with respect to causality of a neuropsychiatric disorder if its critical exon fraction fell within the genome's top $25^{th}$ percentile for at least 50% of the biological samples.

Various methods have been developed for constructing gene co-expression networks. In principle, each are based on a two step approach: calculating co-expression measure, and selecting significance threshold. In the first step, a co-expression measure is selected and a similarity score is calculated for each pair of genes using this measure. Then, a threshold is determined and gene pairs which have a similarity score higher than the selected threshold are considered to have a significant co-expression relationship. Co-expression measures for constructing gene co-expression networks may include Pearson's correlation coefficient, Mutual Information, Spearman's rank correlation coefficient and Euclidean distance. A Weighted Gene Co-expression Network Analysis (WGCNA) may also be conducted which selects the threshold for constructing the network based on the scale-free topology of gene co-expression networks. This method constructs the network for several thresholds and selects the threshold which leads to a network with scale-free topology. Moreover, the WGCNA method constructs a weighted network which means all possible relationships appear in the network, but each is weighted to show the significance of the co-expression relationship. Such gene co-expression analyses are conducted using methods well-established in the art, and will employ automated computerized methods.

The present method may be used to identify genes linked to disease causality of disease conditions such as those involved in any developmental process with respect to the brain, blood, heart, kidney, and others, and that might lead to neurological disease, cardiomyopathy, stroke, cancer and diabetes. As will be appreciated by one of skill in the art, depending on the condition for which genes related to causality are to be determined, the biological sample may vary. In addition, where a gene co-expression analysis is conducted, enrichment for genes encoding proteins relevant to the selected disease condition may be employed and may be different from that described herein for developmental delay.

As one of skill in the art will appreciate, steps of the present application are generally carried out using an appropriate processing device, e.g. a computer. For example, the steps of identifying exons which exhibit an expression level that is greater than the $75^{th}$ percentile of exon expression levels within a sample and, optionally, conducting a gene co-expression analysis, comparing the sequence of each identified exon to the sequence of a corresponding exon from a healthy control to identify sequence mutations, calculating the burden of rare or de novo mutations within the exon, determining the correlation between expression level of the identified exon and burden of de novo or rare mutations in the exon, as shown in FIGS. 30A and 30B, may each be conducted using a processing device or computer to analyze datasets of exons, conduct comparisons against controls and then to do calculations. In order for the present methods to be practiced in a practical manner, the use of a processing device, e.g. a computer, is essential. For example, due to the volume of data to be analyzed and the methods by which the data is analyzed (e.g. complex computations), if the method were practiced without the use of a processing device it would require an excessive amount of time and effort and would not provide a result within a reasonable period of time. A benefit of the present invention is that that method can be performed such that its results may have a practical effect with respect to diagnosis and subsequent treatment.

An appropriate processing device for use to conduct each step of the present method may include any suitable computer or microprocessor-based system, such as a desktop or laptop computer or a mobile wireless telecommunication computing device, such as a smartphone or tablet computer, which may receive data or information to be processed. The computer or microprocessor-based system may be coupled to another device from which data/information to be processed in accordance with the claimed method, or such data/information may be obtained from a separate storage medium or network connection such as the Internet. An illustrative computer system in respect of which the methods herein described may be implemented is presented as a block diagram in FIG. 29. The illustrative computer system is denoted generally by reference numeral 10 and includes a display 12, input devices in the form of keyboard 14 and pointing device 16, computer 18 and external devices 30. While pointing device is depicted as a mouse, it will be appreciated that other types of pointing device may also be used.

The computer may contain one or more processors or microprocessors, such as a central processing unit (CPU) 22. The CPU performs arithmetic calculations and control functions to execute software stored in an internal memory 26, preferably random access memory (RAM) and/or read only memory (ROM), and possibly additional memory 32. The additional memory may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces, removable memory chips such as EPROM or PROM, emerging storage media, such as holographic storage, or similar storage media as known in the art. This additional memory may be physically internal to the computer, external, or both. Information utilized in the present methods may be stored on the internal memory 26 or the additional memory 32, for example, tissue expression data and nucleic acid sequence data, such as the Exome Sequence Project (ESP) data, human brain microarray data, and human brain RNA Sequencing (RNA-seq) data. The computer system may also include other similar means for allowing computer programs or other instructions to be loaded. Such means can include, for example, a communications interface 34 which allows software and data to be transferred between the computer system and external systems and networks. Examples of communications interface include a modem, a network interface such as an Ethernet card, a wireless communication interface, or a serial or parallel communications port. Software and data transferred via communications interface are in the form of signals which can be electronic, acoustic, electromagnetic, optical or other signals capable of being received by communications interface. Multiple interfaces, of course, may be provided on a single computer system.

Input and output to and from the computer is administered by the input/output (I/O) interface 20. This I/O interface administers control of the display, keyboard, external devices and other such components of the computer system. The computer will generally include a graphical processing unit (GPU) 24 useful for computational purposes as an adjunct to, or instead of, the CPU 22, for mathematical calculations.

The various components of the computer system are coupled to one another either directly or by coupling to suitable buses.

The methods described herein may be provided as computer program products comprising a tangible computer readable storage medium, such as non-volatile memory, having computer readable program code embodied therewith for executing the method. Thus, the non-volatile memory would contain instructions which, when executed by a processor, cause the computing device to execute the relevant method.

The above systems and methods may be implemented entirely in hardware, entirely in software, or by way of a combination of hardware and software. In a preferred embodiment, implementation is by way of software or a combination of hardware and software, which includes but is not limited to firmware, resident software, microcode, and the like. Furthermore, the above systems and methods may be implemented in the form of a computer program product accessible from a computer usable or non-transitory computer readable medium providing program code for use by or in connection with a computer or any instruction execution system. In such embodiments, the computer program product may reside on a computer usable or non-transitory computer readable medium in a computer such as the memory of the onboard computer system of the smartphone, or the memory of the computer, or on a computer usable or computer readable medium external to the onboard computer system of the smartphone or the computer, or on any combination thereof.

An illustrative method 100 of the present invention performed by a processing device is presented as a block diagram in FIG. 30A. The method begins (block 101) with the optional step of conducting a gene co-expression analysis to identify relevant genes (e.g. weighted gene co-expression analysis—WGCNA), and then identifying exons which exhibit an expression level greater than the 75% percentile of exon expression levels in relevant genes of nucleic acid from one or more individuals having a disease such as a neuropsychiatric disorder (block 102). Then, the sequence of an identified exon is compared to the sequence of a corresponding exon from a healthy control (block 104). For rare or de novo sequence mutations detected (block 106), the method calculates the burden of rare or de novo mutations within the exon (block 108), and then determines the correlation between expression level of the identified exon and burden of de novo or rare mutations in the exon to identify critical exons (block 110). The process then moves on to the next identified exon (blocks 112, 114) and repeats the steps from blocks 104 and 106. At block 106, if no rare or de novo sequence mutations are detected, then the process moves on the next identified exon (blocks 116, 118) and repeats the steps from blocks 104 and 106. Once the method has iterated through all of the identified exons (block 114; count=total or block 118; count=total), then the process ends (block 120).

The information obtained from method 100 of the present invention may then be utilized to diagnose disease in steps further performed by a processing device presented as a block diagram in FIG. 30B. Method 100 is shown and begins (block 101) with an optional preliminary step of a weighted gene in co-expression network analysis (WGCNA) using protein expression to identify relevant genes, e.g. WGCNA (block 102). Then critical-exons within relevant genes for a tissue are identified in which exon mRNA expression level is greater than the 75% percentile (compared to the genome), and rare non-synonymous mutation burden in the population is <75% percentile (blocks 103-110 of FIG. 30A). For example, critical exons are identified which exhibit an expression level greater than the 75% percentile of exon expression levels, and which express rare or de novo non-synonymous variants in which the rare or de novo mutation burden inversely correlates with the expression level. The method 100 is shown in FIG. 30B; however, once the information regarding genes/mutations associated with disease causality have been determined, this method need not be repeated again in conjunction with diagnostic method 200 of FIG. 30B. Thus, method 200 may be conducted following and separately from method 100.

From a disease cohort, a method 200 performed by a processing device is applied to diagnose disease in a patient, based on the critical exons identified using method 100. Method 200 includes identifying the rare or de novo non-synonymous variants in nucleic acid samples and identifying the exon comprising the variant (block 120). Next, the variant-impacted exon (e.g. mutant exon) is compared with indexed critical-exons (block 122), e.g. identified by the method 100. If the mutant exon is determined to be a critical exon, the method may also identify the expression and the tissue type of the mutant exon (determined to be critical) (block 124) to verify relevance of mutant exon. The method may also be used to identify the corresponding protein network for the mutant exon gene (block 126). Thus, disease causality and/or disease diagnosis, may be conducted based on the presence of one or more critical exons using the present methods. The process may then move on to the next identified mutation and/or the next patient (blocks 128, 130) and repeats the steps from blocks 120 and 122. At block 122, if a critical exon is not detected, then the process moves on the next rare or de novo sequence mutation and/or patient for comparison of mutations with exons indexed as critical (blocks 132, 134) and repeats the steps from blocks 120 and 122. Once the method has iterated through all of the mutations (block 130; count=total or block 134; count=total), then the process ends (block 140).

Thus, the present method advantageously provides a means of identifying disease causality in complex developmental disorders, such as neuropsychiatric disorders, that will aid in the diagnosis and treatment of such diseases. In particular, genes relevant to a neuropsychiatric disorder may be identified, including the related sequence mutation(s) within a pertinent exon of the particular disease-related gene. The identification of disease causality in this manner lends to the diagnosis of neuropsychiatric disorders, and provides a basis for developing treatments thereof by providing valid targets on which potential treatments may be based.

Embodiments of the present invention are described in the following specific examples which are not to be construed as limiting.

Example 1

Materials and Methods

Burden of Rare Missense Mutations

Data from the Exome Sequence Project (ESP) initiated by US National Health Heart, Lung and Blood Institute (NHLBI) was used to calculate the burden of rare missense mutations in human populations. The data was processed by computer to identify variants according to steps 104 and 106 of FIG. 30. Variants were obtained from 6,503 exomes (2,203 African Americans (AA) and 4,300 European Americans (EA)); each exome had a median sequence coverage of at least 100 X (Fu et al. Nature 493, 216-220 (2013); published online Epub Jan. 10 (10.1038/nature11690). The composite RefSeq gene annotation (which includes all exons from annotated isoforms) was used for the analysis and after excluding genes with no variant calls (3,267 genes), a total of 20,417 genes (including protein coding and pseudo genes) remained for analysis. The number of variants that passed quality control was 1,284,453 in EA exomes and 1,162,001 in AA exomes. Of these, the rare variants (<0.05 frequency) were 968,840 (75%) for EA and 600,174 (51%) for AA. The differences in rare variants between these two populations are highlighted in Fu et al. 2013. Using a computer, the burden of rare missense mutation at the exon level for European populations using the genome analysis toolkit (GATK) variant annotation was determined according to step 108 of FIG. 30. Rare missense variants with a frequency <0.05 are a strong proxy for recent (mostly within the last 5,000-10,000 years) accelerated deleterious mutation events in humans. For any exons within the composite gene model (hg19) (FIG. 1), variants annotated as missense for any gene isoform were considered. A normalized burden of mutation was calculated from the rare missense count for each exon e in the EA data:

$$e_n = \frac{\text{(rare missense count)}}{[e_l]}$$

where $e_n$ is the normalized exon burden and $[e_1]$ is the length of exon e.

Expression Data

A. Multiple Tissue Expression Data

Expression data was obtained from the Affymetrix GeneChip Human Exon 1.0 ST array for 11 normal human tissues, each in triplicate (Gardina et al. BMC genomics 7, 325 (2006)10.1186/1471-2164-7-325). Tissues included cerebellum, breast, heart, liver, muscle, kidney, thyroid, pancreas, prostate, spleen, and testis. Partek® Genomics Suite™ was used to compute core meta-probe set signal intensity from the raw .CEL. Exons were kept for analysis only if they were also covered in the exome sequencing project for variant calls. Probes prone to multiple hybridizations were excluded. The Robust Multi-array Average (RMA) algorithm (Irizarry et al. Nucleic acids research 31, e15 (2003)) was used for background signal subtraction; normalization and the log 2 expression value was computed for each exon. A total of 16,713 RefSeq genes (covering 141,224 exons) were surveyed in all 11 tissues. Using a threshold of $\log_2$-transformed intensity ≥6 to define expressivity (Sanders et al. Nature 485, 237-241 (2012)), 16,411 genes were detected with at least one exon expressed for a tissue sample.

Figure 5:
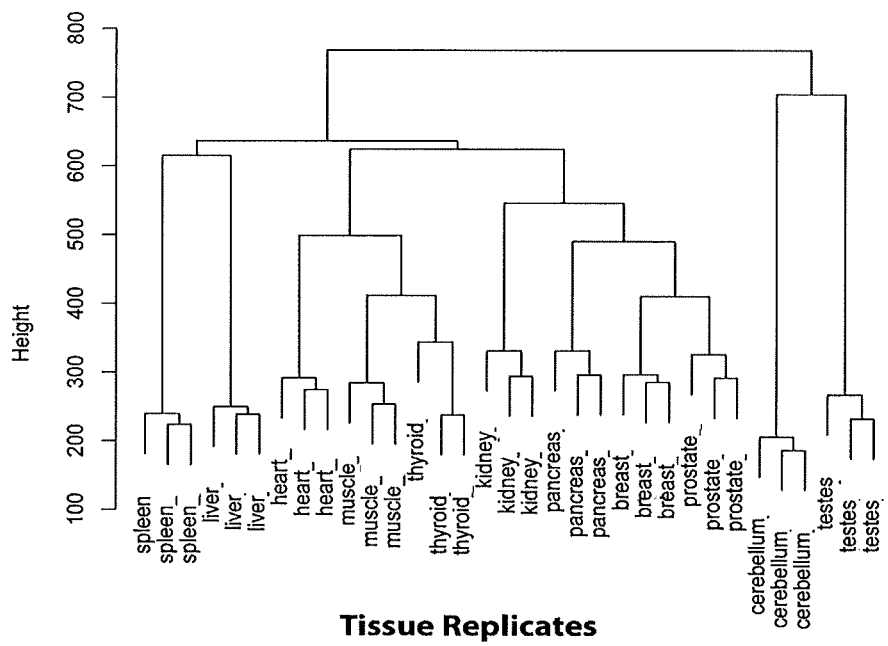
FIG. 5. Clustering of expression data. (A) The hierarchical clustering dendogram of replicates (A, B, C) for tissue types. The expression clustering for cerebellum and testis shows unique variance compared to the other tissues. (B) Principal component 1 (PC1) and 2 (PC2) plotted (for all replicates) for the tissue types capturing variance from their corresponding expression profile.
Figure 5:
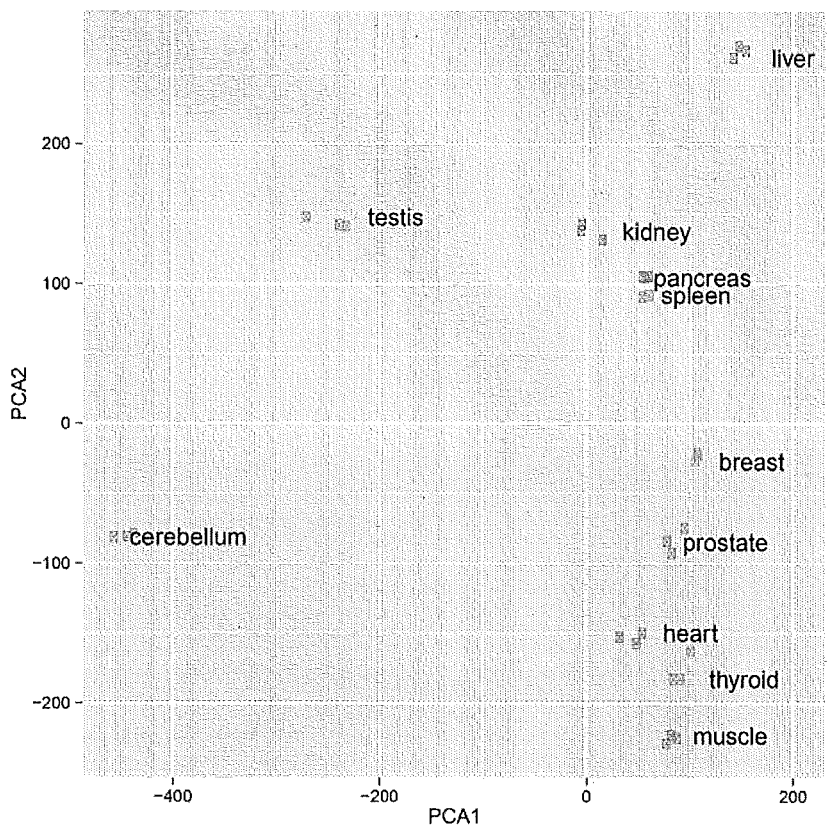

Hierarchical clustering with Euclidean distance is a method to detect overall variation among replicates. This method typically finds groups of genes with a similar expression pattern. Then, a dendogram can be constructed to illustrate the relationship between replicates. This approach demonstrated that the replicates were clustered strongly according to tissue type (FIG. 5A); testis and cerebellum showed similar expression patterns, different from the other tissues. A second method was applied—principal component analysis (PCA)—to capture overall variance among the tissues. PCA analysis also showed that tissues highly clustered by tissue type (FIG. 5B), with testis and cerebellum showing greater variance compared to other tissues.

B. Human Brain Microarray Data

The spatio-temporal expression profiles from developmental human brain used in this study were from the BrainSpan database (Sanders et al. 2012). The samples were chosen so that each developmental period comprised at least two age- and sex-matched donors (Table 1). The developmental periods were categorized into three groups: prenatal (8 post-conception weeks (pew) to 21 pew), early childhood (4 months to 3 years) and adulthood (≥13 years). For each donor, expression data was obtained from at least 13 brain regions (Table 1 and 2). These included neocortex (NCX) (11 NCX regions includes orbital frontal cortex (OFC), dorsolateral prefrontal cortex (DFC), ventrolateral frontal cortex (VFC), medial prefrontal cortex (MFC), primary motor cortex (MIC), primary somatosensory cortex (S1C), posterior inferior parietal cortex (IPC), primary auditory cortx (A1C), posterior superior temporal cortex (STC), inferolateral temporal cortex (ITC), primary visual cortex (V1C)), amygdala (AMY), cerebellar cortex (CBC), hippocampus (HIP), mediodorsal nucleus of the thalamus (MD), and striatum (STR).

TABLE 2

Brain region ontology and nomenclature used in this study.

| Brain Region Analysed | Region Name |
|---|---|
| AMY | amygdaloid complex |
| CGE | caudal ganglionic eminence |
| DFC | dorsolateral prefrontal cortex |
| DTH | dorsal thalamus |
| HIP | hippocampus |
| ITC | inferolateral temporal cortex |
| LGE | lateral ganglionic eminence |
| MFC | medial prefrontal cortex |
| MGE | medial ganglionic eminence |
| M1C-S1C | primary motor-sensory cortex |
| Ocx | occipital neocortex |
| OFC | orbital frontal cortex |
| PCx | parietal neocortex |
| STC | posterior (caudal) superior temporal cortex |
| URL | upper (rostral) rhombic lip |
| VFC | ventrolateral prefrontal cortex |
| A1C | primary auditory cortex |
| IPC | posterior inferior parietal cortex |
| M1C | primary motor cortex |
| S1C | primary somatosensory cortex |
| STR | striatum |
| CB | cerebellum |
| MD | mediodorsal nucleus of thalamus |
| V1C | primary visual cortex |
| CBC | cerebellar cortex |

RNA from 196 tissue samples from 13 post mortem donors were run on the Affymetrix GeneChip Human Exon 1.0 ST array platform. This data set surveyed 17,296 genes,

TABLE 1

Spatio-temporal Transcriptome (microarray and RNA-SEQ) data. Human development periods and sample brain tissues from 13 postmortem donors.

| Age/Period | Category | Male (M) | Female (F) | Analyzed Brain Region Nomenclature M | F |
|---|---|---|---|---|---|
| 8pcw/Embryonic | Embryonic | 13058 | — | AMY, CGE, DFC, DTH, HIP, ITC, LGE, MFC, MGE, M1C-S1C, Ocx, OFC, PCx, STC, URL, VFC | — |
| 13pcw/Early Fetal | Prenatal | 12820 | 12834 | A1C, AMY, DFC, HIP, IPC, ITC, M1C, MFC, OFC, S1C, STC, STR, VFC | A1C, CB, DFC, HIP, IPC, ITC, M1C, MD, MFC, OFC, S1C, STC, STR, V1C, VFC |
| 21pcw/Late Fetal | Prenatal | 12886 | 12365 | A1C, AMY, CBC, DFC, HIP, IPC, ITC, M1C, MD, MFC, OFC, S1C, STC, STR, V1C, VFC | A1C, AMY, CBC, DFC, HIP, IPC, ITC, M1C, MD, MFC, OFC, S1C, STC, STR, V1C, VFC |
| 4-6 Mo/Early Infancy | Early Childhood | 12296 | 12297 | A1C, AMY, CBC, DFC, HIP, IPC, ITC, M1C, MD, MFC, OFC, S1C, STC, STR, V1C, VFC | A1C, AMY, CBC, DFC, HIP, IPC, ITC, M1C, MD, MFC, OFC, S1C, STC, STR, V1C, VFC |
| 3 Y/Early Childhood | Early Childhood | 12980 | 12836 | A1C, AMY, CBC, DFC, HIP, IPC, ITC, M1C, MFC, OFC, S1C, STC, V1C, VFC | A1C, AMY, CBC, HIP, IPC, ITC, M1C, MD, S1C, STC, STR, V1C, VFC |
| 13-15 Y/Adolescence | Adult | 12299 | 12831 | A1C, AMY, CBC, DFC, IPC, ITC, M1C, MD, MFC, OFC, S1C, STC, STR, V1C, VFC | A1C, AMY, CBC, DFC, HIP, IPC, ITC, M1C, MD, MFC, OFC, S1C, STC, STR, V1C, VFC |
| 37-40 Y/Adulthood | Adult | 12303 | 12304 | A1C, AMY, DFC, HIP, IPC, ITC, M1C, MD, MFC, OFC, S1C, STC, STR, V1C, VFC, | A1C, AMY, DFC, HIP, IPC, ITC, M1C, MD, MFC, OFC, S1C, STC, STR, V1C, VFC | pcw = post-conceptional weeks;
Mo = months;
Y = years.

comprising 230,881 exons, from which at least one exon was expressed ($\log_2$-transformed signal intensity of ≥6) in at least one brain region. The quality control (QC) measures and the microarray data processing can be found at Kang et al. *Nature* 478, 483-489 (2011). Further quantile normalization was applied across all samples. Exons without probes in the microarray, or if not covered in the NHLBI exome sequencing project, were also excluded. The 'loadings' of principle component analysis (PCA) are correlation coefficients between the principle component scores and the original variable, and reflect the importance of each variable in accounting for the variability in the principle component. A PCA box plot was constructed (FIG. 2) for the gene sets and loading vectors extracted from genome-wide spatio-temporal PCA analysis on 196 brain samples (with gene as object). It showed the greatest variation (captured as the first principal component (PC1) loadings) between prenatal (embryonic, early and late prenatal) and postnatal (early childhood and adult) transcriptomes. The second component (PC2) loadings captured variation between embryonic and early childhood expression of genes. The analysis from both PC1 and 2 shows CBC with highest variance among all brain regions analyzed.

C. Human Brain RNA Sequencing (RNA-Seq) Data

RNA sequencing (RNA-seq) data was derived from the BrainSpan database. These data contained transcriptome profiles from the same 196 tissues from 13 postmortem donors as used in the microarray analysis. Method details for sequencing, alignment, quality control and expression quantification can be found in the BrainSpan Technical White Paper 2011. The expression measures were provided for exons as reads per kilobase (kb) per million (RPKM) from mapped reads. Quantile normalization was applied to the computed RPKM to reduce systematic bias across the samples. Exons were excluded if not covered in the exome sequencing project. RNA-seq data were used primarily to validate association significance (between exon expression level and burden of rare missense mutations) that was observed by microarray.

3. Candidacy Tier of Genes for Neuropsychiatric Phenotypes

A. De Novo Single Nucleotide Variants (SNV) and Indels

To validate the analysis, a set of de novo mutations that are highly likely to give rise to the neurological conditions under study (i.e., ASD or other) were used. Hence, 243 genes with 256 de novo mutations (nonsense, frameshift, splicing, missense) that are validated and predicted (using multiple algorithms) to be highly damaging, from nine whole genome/exome sequencing (WGS/WES) studies were curated. These include 214 genes from ASD studies; 14 from a schizophrenia study; and 15 from intellectual disability studies. 82 genes with 84 de novo possibly damaging exonic mutations from two large studies were compiled that used the Simon Simplex Collection (SSC). SSC is a phenotypically comprehensive resource of simplex pedigrees that consists of ASD probands and their unaffected siblings.

B. De Novo Copy Number Variation (CNV)

de novo CNVs were collected from three published data sets (Pinto et al. *Nature* 466, 368-372 (2010); Levy et al. *Neuron* 70, 886-897 (2011); Sanders et al. *Neuron* 70, 863-885 (2011)) and one unpublished case-control set (Autism Genome Project (AGP) stage 2). AGP Stage 1 reported its genome wide finding with validated rare/de novo CNVs using the Illumina 1M-single array (Pinto et al. 2010). The ongoing stage 2 uses Illumina 1M-Duo. The total number of ASD cases used (stage 1+2 combined) was 2,446 and 2,640 controls. In the present analysis, 101 validated de novo CNVs were used from the cases, which encompass 886 unique genes. From stage 1 and 2 AGP population controls, genes within the rare CNVs (<0.01 frequency) were used for the analysis. In addition, de novo/rare losses impacting coding sequences for a single gene exclusively in ASD Probands were documented. Similarly, rare single genic losses observed exclusively in controls were ascertained (Table 3).

TABLE 3

AGP dataset (from stage 1 and 2) consists of losses impacting coding sequences for a single gene (de novo/rare).

| AGP Stage 1 + 2 | Rare + de novo (Single Genic CNV Loss) genes. |
|---|---|
| ASD Cases | 153 |
| Controls | 148 |

Genome wide de novo CNVs from two large well-studied SSC cohorts were curated; SSC1 refers to 64 de novo CNVs (affecting 497 genes and SSC2 refers to 75 de novo CNVs (affecting 993 genes). A significantly increased de novo CNV burden is documented for ASD probands. For the SSC cohorts, there were not enough validated rare/de novo CNVs reported for unaffected siblings for meaningful statistical analysis.

C. OMIM Dominant and Recessive Phenotypic Genes for Nervous System

Online Mendelian Inheritance in Man (OMIM) is a continuously updated catalog of human genes and genetic disorders and traits. The database is a compendium of human genes and phenotypic information. The MIM number notation was used to infer the mode of inheritance for all the genes in the Human Phenotype Ontology (HPO) database. Genes with HPO phenotype annotation derived from OMIM were only considered, the mode of inheritance could reliably be inferred for these. OMIM identifiers corresponding to official gene symbols were obtained from the Bioconductor package (version 2.8), available for R statistical software (version 2.15.3). The analysis was primarily based on human phenotypes: "abnormality of the nervous system" (HP: 0000707) which includes 319 autosomal dominant genes, and 487 recessive genes.

D. FMRP and FOXP2 Target Genes

The loss of Fragile X mental retardation protein (FMRP) causes Fragile X Syndrome (FXS) which is the most common inherited form of intellectual disability. FXS is the leading monogenic cause of ASDs; approximately 50% of all FXS cases show autistic behavior. 842 gene products have been identified as FMRP targets. Multiple lines of evidence show a significant enrichment of mutations in FMRP target genes among ASD probands. The functional relevance of FMRP targets is also implicated within the context of ASD pathogenesis. The surplus of pathogenic mutations among FMRP targets for cases relative to controls implies that the targets are undergoing strong purifying selection.

In contrast to FMRP, a subset (Table 4) of genes targeted by Forkhead box P2 (FOXP2) protein show strong evidence of positive selection. FOXP2 is a highly conserved gene implicated in human speech and language disorders. Its target genes have been curated from three studies and Ayub et al. 2013 showed a subset of these (131 genes) to have strong positive selection properties only in the European population (as used in this analysis). These genes play important roles in the plasticity of the human developing brain.

TABLE 4

FMRP target genes; FOXP2 gene targets show evidence of positive selection; and the reported ASD genes (autosomal dominant and X-linked).

| Category (Positive/Purifying Selection) | Genes |
|---|---|
| FMR1 Targets Under Positive Selection | 842 |
| FOXP2 Targets Under Positive Selection | 131 |
| ASD (AD = autosomal dominant and XL = X-linked) | 81 |

E. Genes for Post-Synaptic Proteome (PSP)

Bayés et al. (*Nature neuroscience* 14, 19-21 (2011)), isolated post-synaptic density from human neocortex and identified a large number of proteins, termed the post-synaptic proteome (PSP). They identified mutations within the PSP genes as the cause of 133 neurological and psychiatric diseases. Evidence from animal models (primate and rodent) also shows the importance of the PSP for nervous system disease and behavior. All experimentally identified human post-synaptic density genes were used in the analysis (Table 4).

F. Single Genes Associated with ASD

A list was curated from studies of ASD families of mutations with Mendelian inheritance (autosomal dominant (AD) or x-linked (XL)). This list consists of the best-studied bona fide ASD genes from multiple independent studies.

4. Analysis

A. Pearson Correlation

The Pearson correlation significance test for linear relationships between exonic expression and rare missense mutation burden was used. P-value <0.05 (after Bonferroni multiple test correction) was the threshold for significance. Unless otherwise noted, the statistical analyses were performed using R statistical software, version 2.15. The Wilcoxon association test (Bonferroni corrected) was applied to quantify spatio-temporal expression differences for exons ascertained by virtue of mutation in probands and unaffected siblings.

B. Association

The association between exon expression level and burden of rare missense mutation using Fisher's exact test (FET) was tested. The association was determined using a computer. To test the association, expression level was classified as high or low (above or below the $75^{th}$ percentile, respectively). The percentile was computed from expression data for all samples, separately either from microarray (11 tissues or spatio-temporal data from BrainSpan) or RNA sequencing, according to steps 102, 103 of FIG. 30A. A similar procedure was used to classify the burden of rare missense mutations in EA data (FIG. 10), according to steps 104-108 of FIG. 30. The association was tested for each tissue sample independently and corrected for multiple tests whereby the observed p-value was multiplied by the number of samples.

C. Splicing Code

Figure 8:
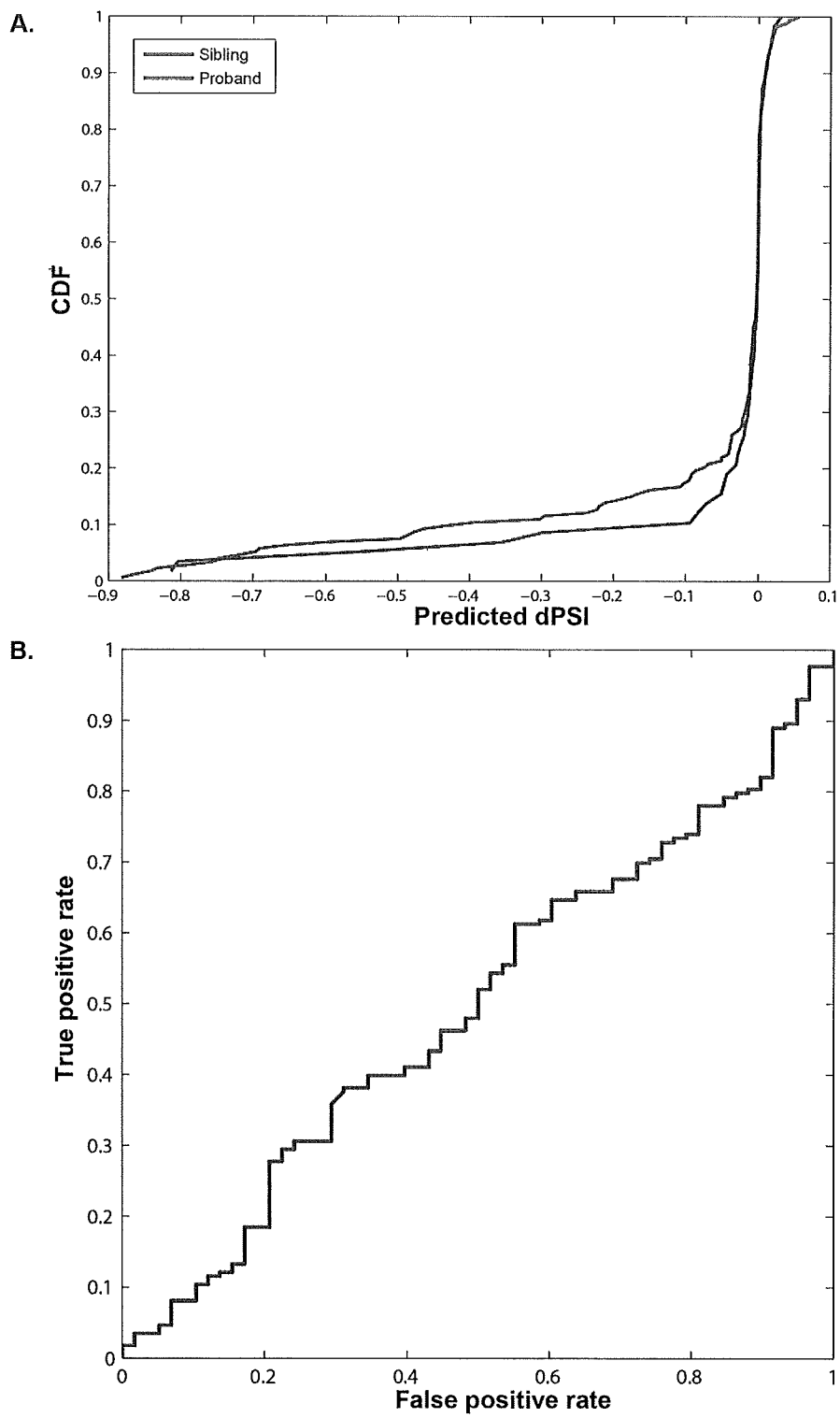
FIG. 8. Splicing code analysis of de novo SNVs. (A) The CDFs of code-predicted $\Delta\Psi$s for probands and unaffected siblings de novo mutations. Overall proband mutations do not have larger predicted $\Delta\Psi$s, and the K-S test does not reject the null hypothesis. (B) The ROC curve for discriminating probands from controls using code-predicted $\Delta\Psi$s; area under ROC curve (AUC) is nearly 0.5.

Previous analysis showed within neocortex regions 57.7% of genes (with at least one exon) showed the presence of differentially expressed exons in prenatal samples, whereas 9.1% and 0.7% of genes had differentially expressed exons in early childhood and adulthood samples, respectively. One mechanism to produce differential expression is through alternative splicing of exons. To analyze the implications of de novo SNVs (ascertained in proband and siblings) on alternative splicing patterns of affected genes, the 'splicing code' (Barash et al. *Nature* 465, 53-59 (2010)) was run on the variants. The de novo mutations were first mapped onto canonical transcripts, and determined the target exon and its flanking introns and immediate neighboring exons. Then, all splicing code cis features were extracted for the mutation and the wildtype counterpart, passed through the code, and the predicted change in inclusion of the target exon was computed. Exon inclusion, denoted, by 'percent spliced-in' (PSI $\Psi$), is defined as the fraction of times an exon is included in the final transcript. For each de novo mutation, the splicing code predicts a $\Delta\Psi$; if a mutation's $\Delta\Psi$ is larger than 95% of $\Delta\Psi$ for common polymorphisms (single nucleotide polymorphism database (dbSNP)), then it was deemed significant. The 'splicing code' analysis found only 73 de novo mutations (i.e. from probands and siblings) to pass the AT threshold of −0.01 (Table 10). The code-predicted $\Delta\Psi$s showed no significant difference between de novo mutations of probands and siblings (Kolmogorov-Smirnov (K-S) test and AUC; FIG. 8).

Next, applying two additional normalizations, it was analyzed whether expression of exons that can vary (according to developing time periods or across tissues) are exons that exclusively contributed to the association between spatio-temporal expression and burden of rare missense. For each gene (g), differential expression was computed by applying two transformations on each exon, $e_{d,i}$: 1) subtracting the exon expression $e_i$ from the gene mean expression $$e_{d,i} = e_i - \frac{1}{n}\sum_i^n g(e_i)$$

and 2) subtracting the total expression from the gene median expression $e_{d,i}=e_i-\text{median}(g(e))$. After applying both normalizations independently to the Brain-Span data, the association test for genes with de novo SNVs (as ascertained from proband or unaffected siblings) using spatio-temporal brain samples was not significant. This indicated that these are not the only exons contributing to the association signal that is consistent with the 'splicing code' analysis.

D. Detection of 'Brain-Critical Exons'

An algorithm was derived to detect 'brain-critical exons', utilizing the multiple tissue microarray expression indices of an exon. Exons classified separately for each dataset into class d (for each dataset $75^{th}$ percentile was used to construct contingency table in FIG. 1) were termed as 'critical exons' reflecting 'high' expression level and 'low' burden of rare missense mutation, according to steps 102 to 110 as shown in FIG. 30. To identify those exons specifically 'critical' in brain (or 'brain-critical exons'), the array matched (Affymetrix GeneChip Human Exon 1.0 ST) multiple tissue data set (ten non-brain tissue replicates) was used. First, all class d 'critical exons' from brain tissues (Brain-Span samples and cerebellum microarray replicates) were identified. From this exon set C, exons were excluded that were not in class d for at least 10% of the brain samples for a given donor (Brain-Span data), or in a cerebellum replicate. Next, exons from set C were excluded that were in class d (for at least one tissue replicate) for ten other non-brain tissues. Therefore, after exclusions, set C' comprised exons with consistently high expression (above $75^{th}$ percentile) and low burden of deleterious mutations, in brain tissue but not in other tissues. Similarly, tissue-specific 'critical exons' were identified from the other tissue types. 15,872 tissue-specific critical exons, of which 3,955 were specific to brain were detected (FIG. 18).

A de novo mutation within one of these 'brain-critical exons' (or in other exons that can indirectly affect (truncate) such exons) could have an adverse effect on brain function while being relatively inconsequential in other tissues. Brain showed at least 2 fold more 'critical exons' compared to other tissues (except testis). A high number of 'testis-critical exons' were also observed. The functional enrichment analysis revealed that the genes corresponding to these 'brain-critical exons' are primarily associated with neuronal development, signaling networks and functions that regulate synapse development and plasticity. Next, each gene (g), was assigned a $$\text{score } S(g) = \frac{\text{\# brain critical exon in } (g)}{\text{mean brain critical exon}}$$

where mean brain-critical exon was computed from all genes in the genome analyzed (FIG. 18).

E. 'Brain-Critical Exons' Enrichment Test

Enrichment of brain-critical exons on candidate gene sets that are highly related to key biological processes in brain and ASD or other co-morbid disease pathogenesis were assayed. FET was first used to identify the sets over-represented in two backgrounds: 1) all exons were compared (first background) to identify 'brain-critical exons' overlaps and 2) restricted the test only to highly (all exons expression above $75^{th}$ percentile for a brain sample in developmental human brains) brain-expressed exons (second background). Although the second background tested a narrow hypothesis, this approach assumes a uniform gene sampling probability, which may not reflect accurately differences in gene exon density and composition. Therefore, an empirical test comparing the percentage of genes with at least one critical exon that are also gene-set members versus the percentage obtained by random exon sampling (first background) was also used; this test was also performed sampling only from brain-expressed exons (second background).

Permutation analysis on FMRP targets, PSP, ASD (AD/XL) and de novo ASD genes was conducted by randomly drawn equal numbers of exons (i.e. 3,955 exons randomly drawn 10,000 times from two backgrounds: RefSeq background and second background with exons highly expressed and analysed the gene set enrichment under these premises. The empirical p-values were computed from 10,000 random draws and false discovery rate (FDR) was computed using the Benjamini-Hochberg method (46).

F. Reverse Transcription Polymerase Chain Reaction (RT-PCR) and Quantitative RT-PCR (qRT-PCR)

The mRNA expression and alternative splicing events in selected genes were analyzed by RT-PCR and qRT-PCR. For detecting splicing events, primer pairs were designed to prime from the flanking exons (exons 3 to 12 of SLC6A1 and exons 16 to 18 for EPB41L3 gene) and different primers were combined to capture most possible exclusion events (for SLC6A1) (Table 5). Exclusion events were confirmed by Sanger sequencing. RNA samples (BD Biosciences) were used from whole adult (A) or fetal (F) human brains as templates for cDNA synthesis using Superscript III First strand Synthesis Supermix (Invitrogen). RT-PCR was performed using standard PCR conditions.

TABLE 5

Primer sequences for alternative splicing and for relative expression analysis by RT-PCR.

| Target region | F | R | Inclusion[a] | Exclusion[b] | Detected[c] |
|---|---|---|---|---|---|
| SLC6A1 exon3-5 | TGACATCGCACGTCCATCTG (SEQ ID NO: 1) | ACAGGTAGTAAATGGCCCAGG (SEQ ID NO: 2) | 503 bp | - | 503 bp, 371 bp, 313 bp, 181 bp |
| SLC6A1 exon4-6 | GAGCCTTCCTGATCCCCTAT (SEQ ID NO: 3) | ACTGTTTCCACGGCAGTGT (SEQ ID NO: 4) | 252 bp | - | 252 bp |
| SLC6A1 exon3-6 | TGACATCGCACGTCCATCTG (SEQ ID NO: 1) | ACTGTTTCCACGGCAGTGT (SEQ ID NO: 4) | 539 bp | - | 539 bp, 407 bp, 349 bp, 217 bp |
| SLC6A1 exon5-7 | CGGCTGCTGTGCTATCATTC (SEQ ID NO: 5) | CAGCCAACACCCTTCCAGAT (SEQ ID NO: 6) | 322 bp | - | 322 bp |
| SLC6A1 exon4-7 | GAGCCTTCCTGATCCCCTAT (SEQ ID NO: 3) | CAGCCAACACCCTTCCAGAT (SEQ ID NO: 6) | 466 bp | - | 466 bp |
| SLC6A1 exon7-9 | GGCTGGATAAGCCAGGTCAG (SEQ ID NO: 7) | GGAAAGAGTTGTAGCTCCCGA (SEQ ID NO: 8) | 330 bp | - | 330 bp |
| SLC6A1 exon8-10 | CCTGTTCTTCCGTGGAGTGA\ (SEQ ID NO: 9) | CATGAAGCCCACGATGGAGA (SEQ ID NO: 10) | 284 bp | - | 284 bp |
| SLC6A1 exon7-10 | GGCTGGATAAGCCAGGTCAG (SEQ ID NO: 11) | TACTCATCCACCAGGGCTGT (SEQ ID NO: 12) | 628 bp | - | 628 bp |
| EPB41L3 exon16-18 | CCTCAACAGACACTGCCGTA (SEQ ID NO: 13) | GTCTCCCGCCGAGTAAGAAG (SEQ ID NO: 14) | 395 bp, | 284 bp, 272 bp | 395 bp, 272 bp |

Figure 3:
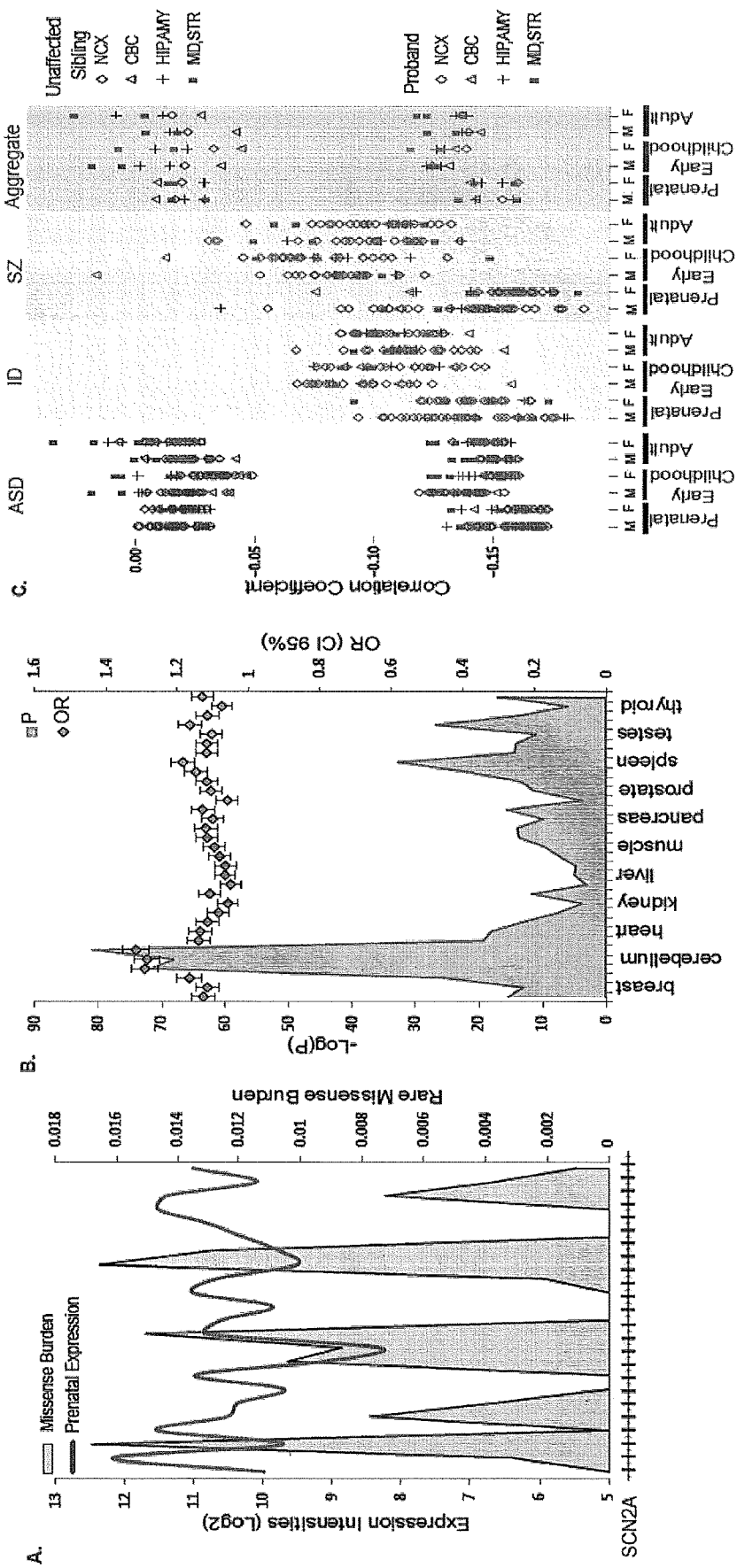
FIG. 3. Inverse correlation between burden of rare missense mutations and exon expression level. (A) Integration of exon expression level and rare missense mutation burden for SCN2A. (B) Genome-wide association between rare missense mutation burden and exon expression level in 11 human tissues (each in triplicate). (C) Exon expression level in 196 postmortem brain samples (controls) (from 13 male and female donors) in three developmental periods (prenatal, early childhood and adult) for 16 brain regions (11 neocortex regions (NCX), cerebellar cortex (CBC), hippocampus (HIP), Amygdala (AMY), mediodorsal nucleus of thalamus (MD), striatum (STR)). The spatio-temporal correlation coefficient shown in three panels was computed for genes reported to have de novo mutations (SNVs-indels) in ASD cases or unaffected siblings, ID and SZ. The last panel shows aggregate spatio-temporal correlation coefficient (average expression from samples for a developmental period) for genes ascertained in unaffected ASD siblings or in any of three disease subject groups.
Figure 12:
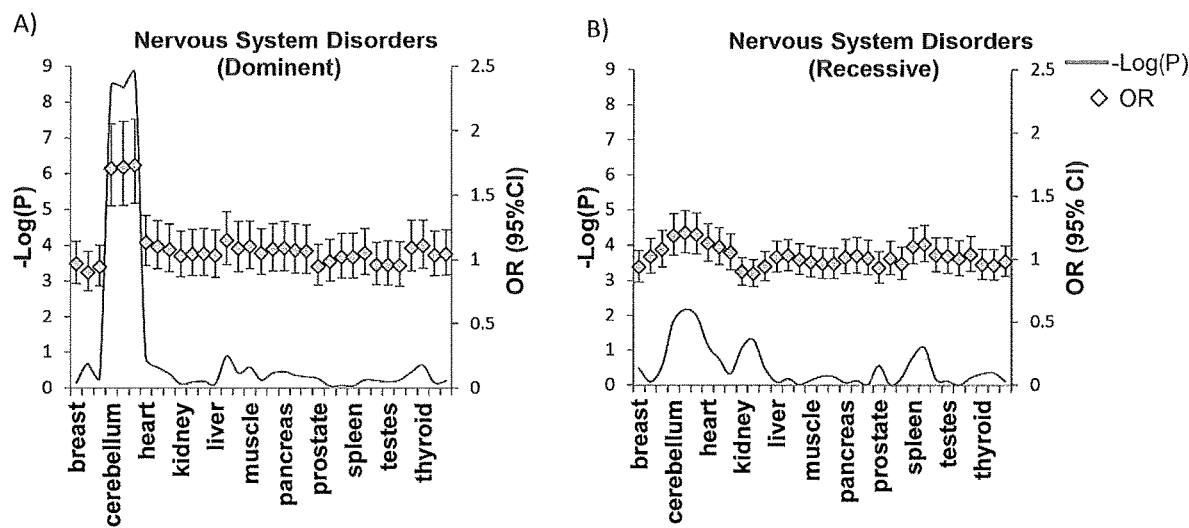
FIG. 12. Association between burden of rare missense mutations and expression (using 11 distinct human tissues, each with 3 replicates) for genes for nervous system disorders (per Online Mendelian Inheritance in Man (OMIM)). The phenotypes are classified (in OMIM) according to mode of inheritance (autosomal dominant (A)/recessive (B)). FET significance for each tissue replicate plotted where the –log(P) on left y-axis and odds ratio (OR) on right y-axis. Cerebellum replicates show the strongest association signals only for dominant nervous system disorder genes.

[a] -expected length in the longest isoform variant.
[b] -expected size of any known exclusion events (Refseq) in the region.
[c] -FIG. 3C or FIG. 12 RT-PCR detection bands length.

TABLE 6

Primer sequences for relative expression quantification using quantitative real-time PCR (qRT-PCR) of brain specific critical exons located within 16p11.2 CNVs.

| Gene | qRT-PCR primers (F/R) |
|---|---|
| KCTD13_F | CCTCATCCCCATGGTGACATC (SEQ ID NO: 15) |
| KCTD13_R | TTACTGCGGTTGTGCAGGAG (SEQ ID NO: 16) |
| ASPHD1_F | GACTTTGTCTTCGCCCCAGA (SEQ ID NO: 17) |
| ASPHD1_R | CTACCATCAAGCCGTCCCTG (SEQ ID NO: 18) |
| SEZ6L2_F | TCCGACATTCTCACTTGCCA (SEQ ID NO: 19) |
| SEZ6L2_R | CCAGGGTCAGCACAAGTCAT (SEQ ID NO: 20) |
| PRRT2_F | GGACTGTTCTCTGCTGGGAC (SEQ ID NO: 21) |
| PRRT2_R | GTTCGGAACCAGTACTCGCC (SEQ ID NO: 22) |
| MED13_F | CCGCATCCTGATGTGTCTGA (SEQ ID NO: 23) |
| MED13_R | TTGCAGGTGGATACGTGACT (SEQ ID NO: 24) |

For the quantification of 'brain-critical exons' by qRT-PCR, primers were designed to prime either from within the specific exon, or within the specific exon and the flanking exon (Table 6). All primers were first tested using RT-PCR with whole brain cDNA, -RT whole brain cDNA and non-target samples as templates. For validation of brain specific critical exon (FIG. 18) expression from selected genes, RNA from 11 human tissues (mammary gland, cerebellum, heart, kidney, liver, skeletal muscle, pancreas, prostate, spleen, thyroid and testis (BD Biosciences) was used. DNase I-treated RNA was reverse-transcribed using Superscript III First strand Synthesis Supermix (Invitrogen). RT-PCR was performed under standard PCR conditions using 10 ng of cDNA as template. The qRT-PCR assay was performed using Brilliant III SYBR® Green PCR Master Mix (Agilent) in a total reaction volume of 15 µl, containing 10 ng of cDNA templates. The reactions were amplified using Mx3005P (Agilent). The expression of each gene of interest was normalized using ACTB or MED13 (dCt) and presented as relative expression ($2^{\wedge}(-dCt)$). The primers were tested for their PCR efficiency by dilution standard curve and for specificity with melting curve analysis.

5. Pathway Enrichment Analysis

A. Construction of Gene Sets

Gene sets were derived from the manually curated gene ontology (GO) (R package, version 2.8.0), pathways from National Cancer Institute at the National Institutes of Health (NCI-NIH) (May 30th 2013), Kyoto Encyclopedia of Genes and Genomes (KEGG) (May 30th 2013) and Reactome (Jun. 3, 2013); websites as previously described. For the analysis, term annotated with more than 1000 genes and fewer than 50 genes were excluded from GO, NCI, KEGG and Reactome, resulting in a total of 4,138 gene sets.

B. Gene Set Overrepresentation Analysis

To identify biologically meaningful pathways, an overrepresentation analysis was performed using the gene sets described above. FET determined the significance of the enrichment for a given pathway. The test evaluates the enrichment of genes in a pathway against a common background consisting of all the genes in the data set. FET was used to assess gene-set enrichment. After obtaining the null distribution of P-values, FDR was computed using the Benjamini-Hochberg procedure. A gene-set was considered to be significantly enriched when FET $p<1.0\times10^{-3}$ and FDR<0.01. This cut-off was used to construct and visually represent a functional enrichment map (FIG. 15C).

C. Permutation Test

A permutation test was undertaken by randomly drawing equal number of exons (3,955) and re-analysis of the data under the null-hypothesis to reveal the strength of enrichment association with the gene list. If this procedure is performed a sufficient number of times, the resulting sets of p-values are presumed to be a reasonable approximation of the null distribution of the p-values, given a test statistic t(observed) and number of permutations n and the test statistics in permuted data t(i,permutation); i=1, . . . n; (n=10,000 permutation).

$$P = \frac{\#(\text{abs}(t(i, \text{permutation})) \geq \text{abs}(t(\text{observed})))}{n}$$

Permutation was conducted for molecular pathway analysis randomly drawing an equal number of exons (equal to 'brain-critical exons' 3,955) from RefSeq genes and enrichment analysis was done on GO, NCI, KEGG and Reactome gene sets. The empirical P-value was not significant after the permutation test.

D. Visualization of Functional Enrichment Map

Gene sets that were significantly enriched with 'brain-critical exons' (described above) were represented by constructing a network where each gene-set is a node, and the edges represent gene overlap between sets. The Cytoscape network software v.2.8.3 and the plugin "Enrichment Map" were used to construct and visualize the network. The node size is proportional to the total number of genes in the respective gene set. After constructing the enrichment map, the nodes were colored according to the p-value obtained from FET. The functional gene-set clusters were manually identified and annotated, and highlighted by shaded ovals/circles, representing groups of gene sets that are highly overlapping. Ovals/circles highlighted blue represents functional pathways implicated in previous ASD or other neuropsychiatric disorders literature; GTPase signaling, ERBB-NGF signaling pathways, neuronal synapse, higher cognitive functions, voltage-gated channel, neuron projection and axonogenesis, synaptic vesicle, brain development, neuron differentiation and mitogen-activated protein kinase (MAPK) cascade.

Results

Figure 1:
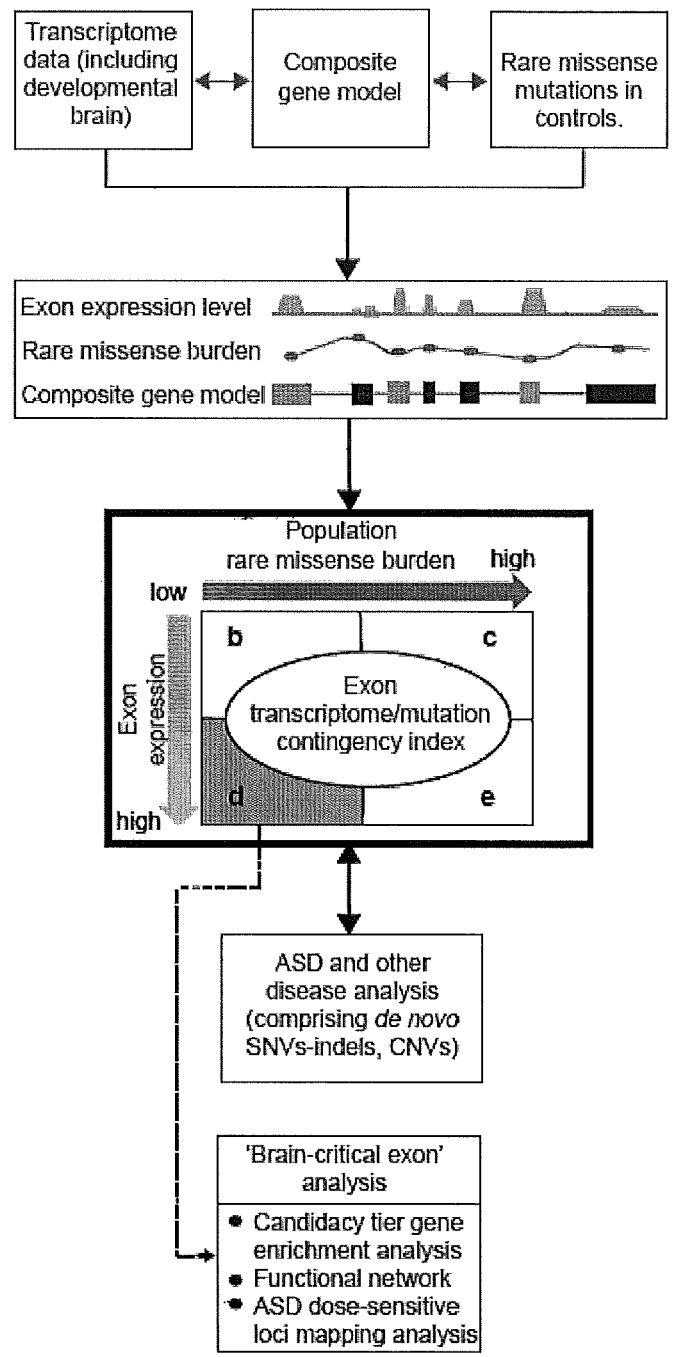
FIG. 1. Assembling an exon transcriptome/mutation contingency index. A composite gene model was generated and used to integrate exon expression and rare missense mutation levels in controls. As a result an 'exon transcriptome/ mutation contingency index' was generated. A 'critical exon' (d) was defined within the contingency index as one being highly-expressed relative to others (a, b, d), and at the same time being suppressed for the accumulation missense mutations in population controls (based on 75th percentile thresholds from the data). Using this transcriptome/mutation contingency index, enrichment analyses were performed for genes implicated in ASD and other disorders. The entire set of 'critical exons' (3,955 in 1,744 genes) were further analyzed for functional enrichment and disease association testing.
Figure 2:
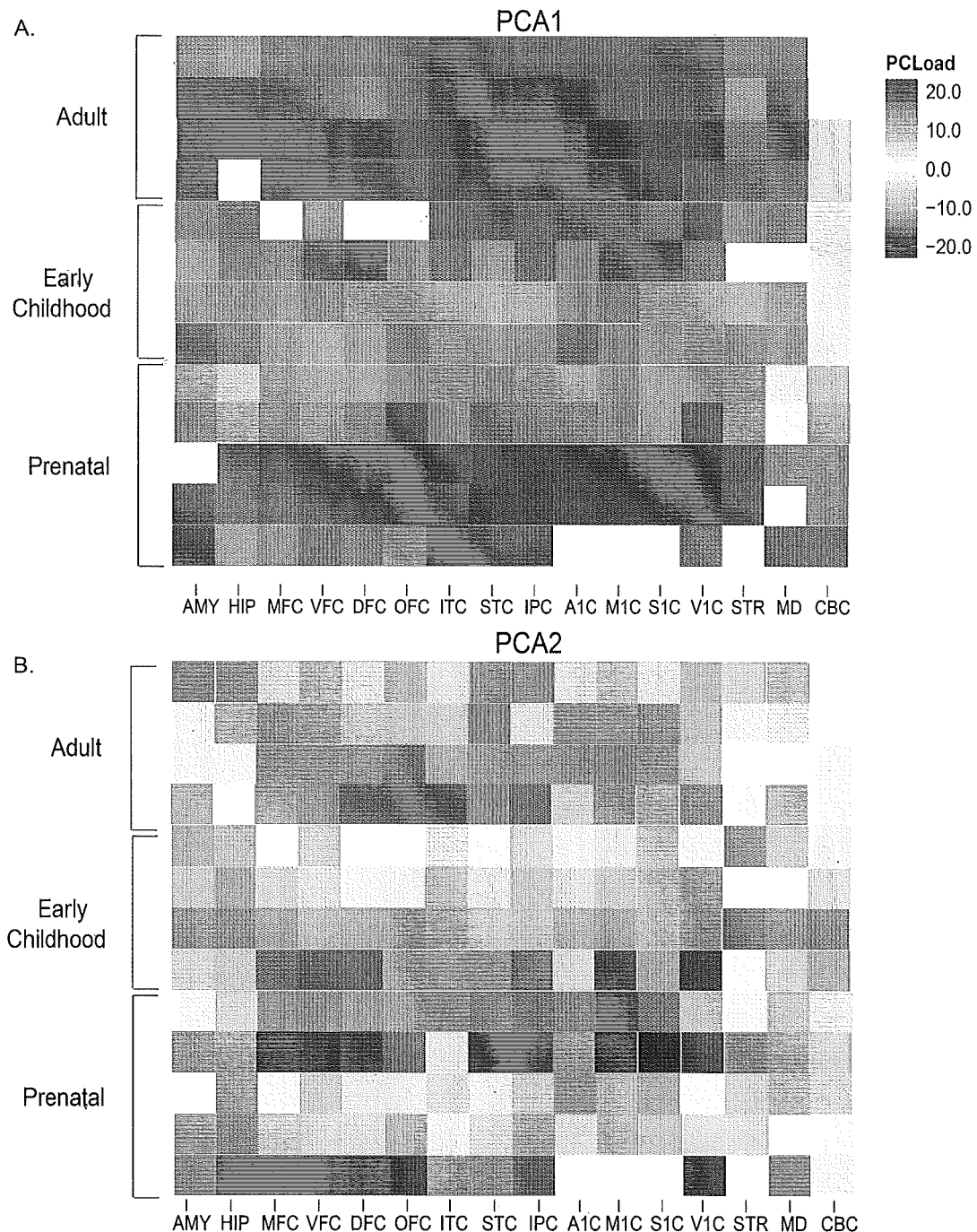
FIG. 2. Principal component analysis (PCA) to capture expression variability between brain samples. (A) Heatmap from principal component analysis showing temporal sample clustering captured by component 1 (PC1) loadings. The color gradient from red to blue represent the expression profile variation captured by the loadings. (B) Component 2 (PC2) loadings captures the variation within the prenatal (late prenatal) to early childhood samples.
Figure 4:
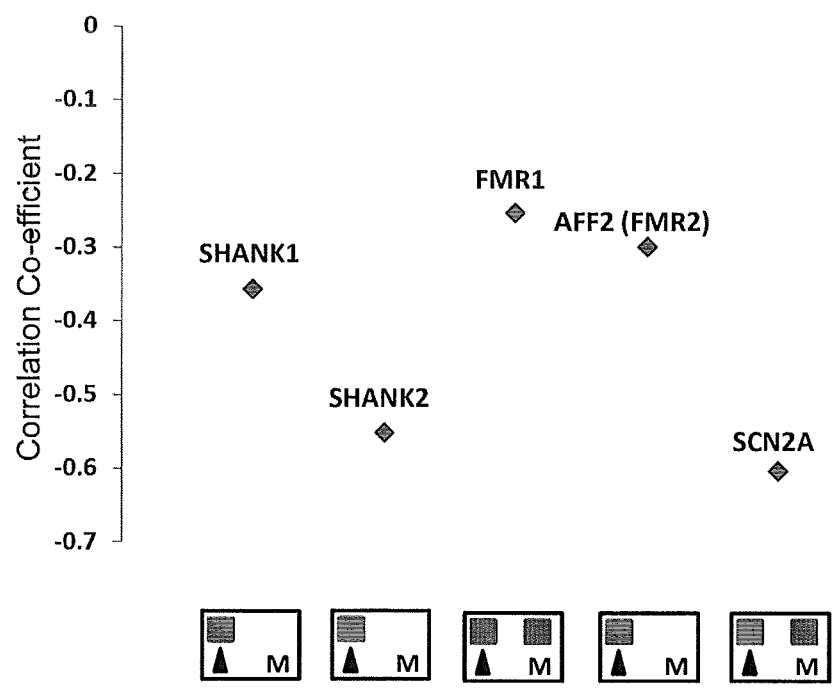
FIG. 4. Pearson correlation co-efficient between burden of rare missense and prenatal brain expression for known ASD genes SHANK1, SHANK2, FMR1, AFF2 (FMR2), and SCN2A. For these genes multiple independent ASD studies reported deletions (red square), duplications (blue square), point mutations (black triangle) or functional evidence from mouse (M) knockout studies.

It was sought to exploit transcriptome maps of human developing brain coupled with data from population genetics studies about mutational burden to examine the impact of genetic variants in ASD and other neuropsychiatric disorders (FIG. 1 and FIG. 2). Exome sequencing has revealed an excess of damaging variants arising over the past 5,000 years among individuals of European ancestry, but how this relates to gene expression in developing human brain or to disease is little understood. The initial examination of a few bona fide ASD risk genes (SHANK1, SHANK2, FMR1, AFF2, SCN2A) in control sample data revealed an inverse correlation between the burden of rare missense mutations (defined as the number of rare missense variants divided by the exon length) and the expression levels for individual exons in prenatal brain (FIG. 3A and FIG. 4).

It was then hypothesized that due to adverse functional consequences, the accumulation of potentially deleterious mutations is suppressed for 'critical exons' demonstrating higher expression in brain. It was undertaken to test whether dysregulation of the expression of such critical exons caused by rare mutations was more likely to cause disease than other exons where recent mutational burden was relaxed regardless of gene expression. Exons were classified in two ways to construct an exon transcriptome/mutation contingency index: (i) exon expression levels were discretized into high and low classes (above or below $75^{th}$ percentile of the entire data, respectively) and (ii) rare missense mutation burden was defined as the number of rare missense variants divided by the exon length and defined as high or low in the same manner (FIG. 1). With expression data from 11 human tissues (each in triplicate (FIG. 5)) including 16,713 RefSeq genes, genome-wide association between the burden of rare missense mutations and exonic expression was determined; brain cerebellum showed a striking association (Fisher's exact test (FET), Bonferroni corrected, $p<2.53\times10^{-67}$) (FIG. 3B).

To examine the relevance of the observations in relation to disease, it was tested whether genes found (by sequencing or microarrays) in selected datasets to carry de novo mutations (SNV/indel or CNV, respectively) predicted to be deleterious, exhibit a similar inverse correlation with spatio-temporal exonic expression. From whole exome or genome sequence datasets of index cases of ASD, SZ or ID, 243 genes containing 256 de novo mutations predicted to be deleterious were collected. For the ASD cases from the Simon's Simplex Collection (SSC), equivalent sequence data exists for unaffected sibling controls, identifying 82 genes with de novo exonic mutations. Exon expression data was obtained from both microarrays and RNA-sequencing of 196 normal human brain tissue samples.

Figure 6:
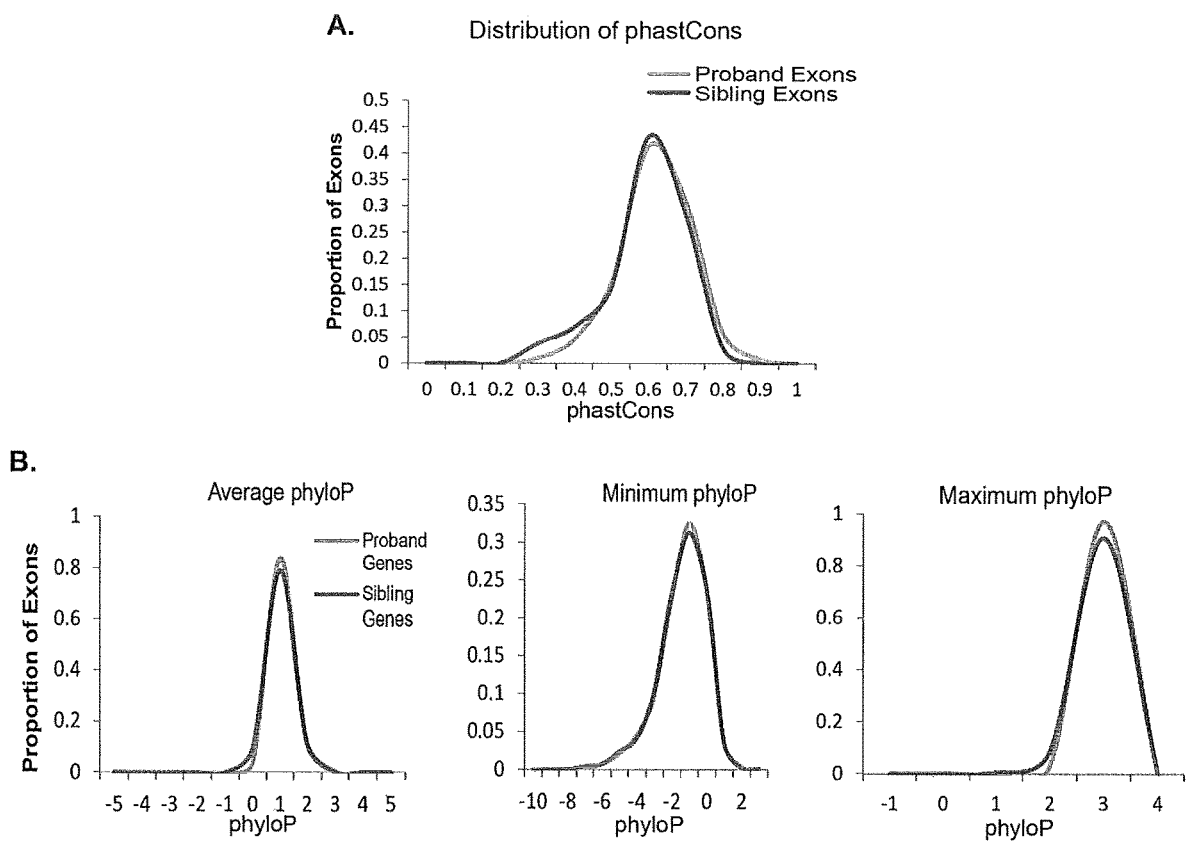
FIG. 6. Distribution of conservation scores for gene exons reported to have de novo SNV/indel mutations in probands or siblings. phastCons and phyloP shows similar conservation patterns for both probands and siblings (mean PhastCons=0.566 and 0.563; phyloP=0.62 and 0.56, respectively). (A) PhastCons score histograms showing computed scores for exons of the gene reported to have de novo mutations in probands or siblings. (B) The distribution of phyloP showing minimum, maximum and average phyloP scores computed for each exon.
Figure 7:
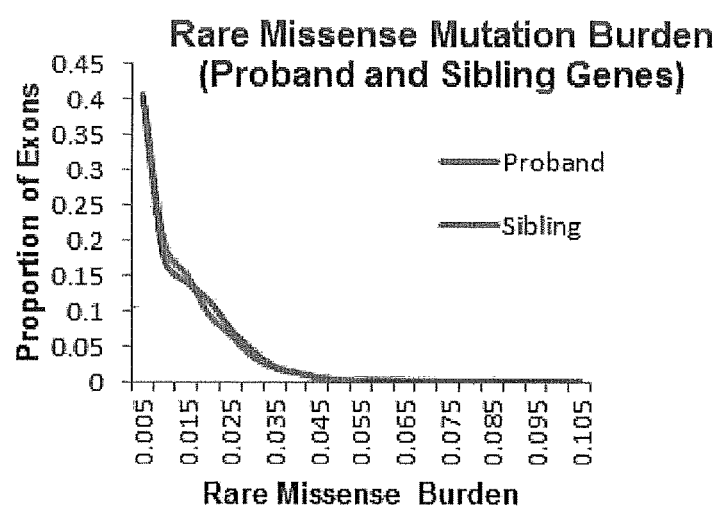
FIG. 7. Distribution of rare missense mutations and age of the mutations for genes ascertained through probands or siblings. (A) Distribution of rare missense mutation burden for genes that harbor de novo mutations in probands and siblings (mean 0.0096 and 0.01, respectively). (B) All detected mutations (common and rare) reported in the exome sequencing database for the genes ascertained in probands or siblings, and mutation age (computed applying coalescent model (9)). (C) Only the rare missense mutations (<0.05 frequency) for genes ascertained through probands or siblings; these potentially deleterious mutations arose within the last 5,000 years.
Figure 7:
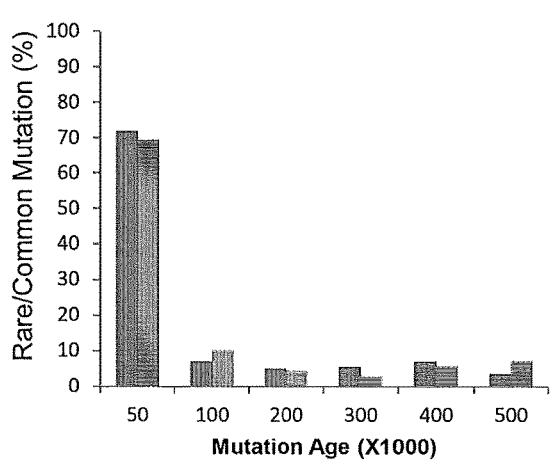
Figure 7:
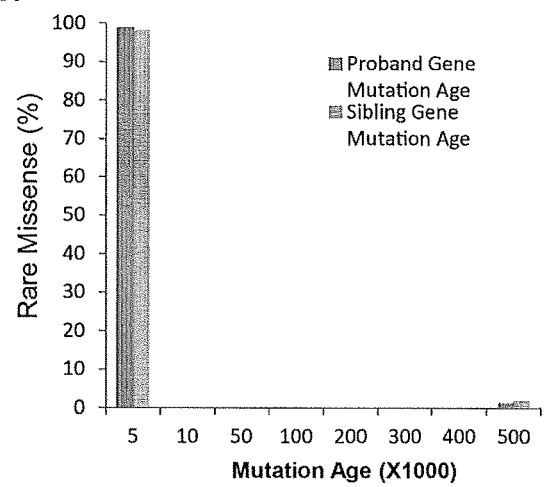
Figure 9:
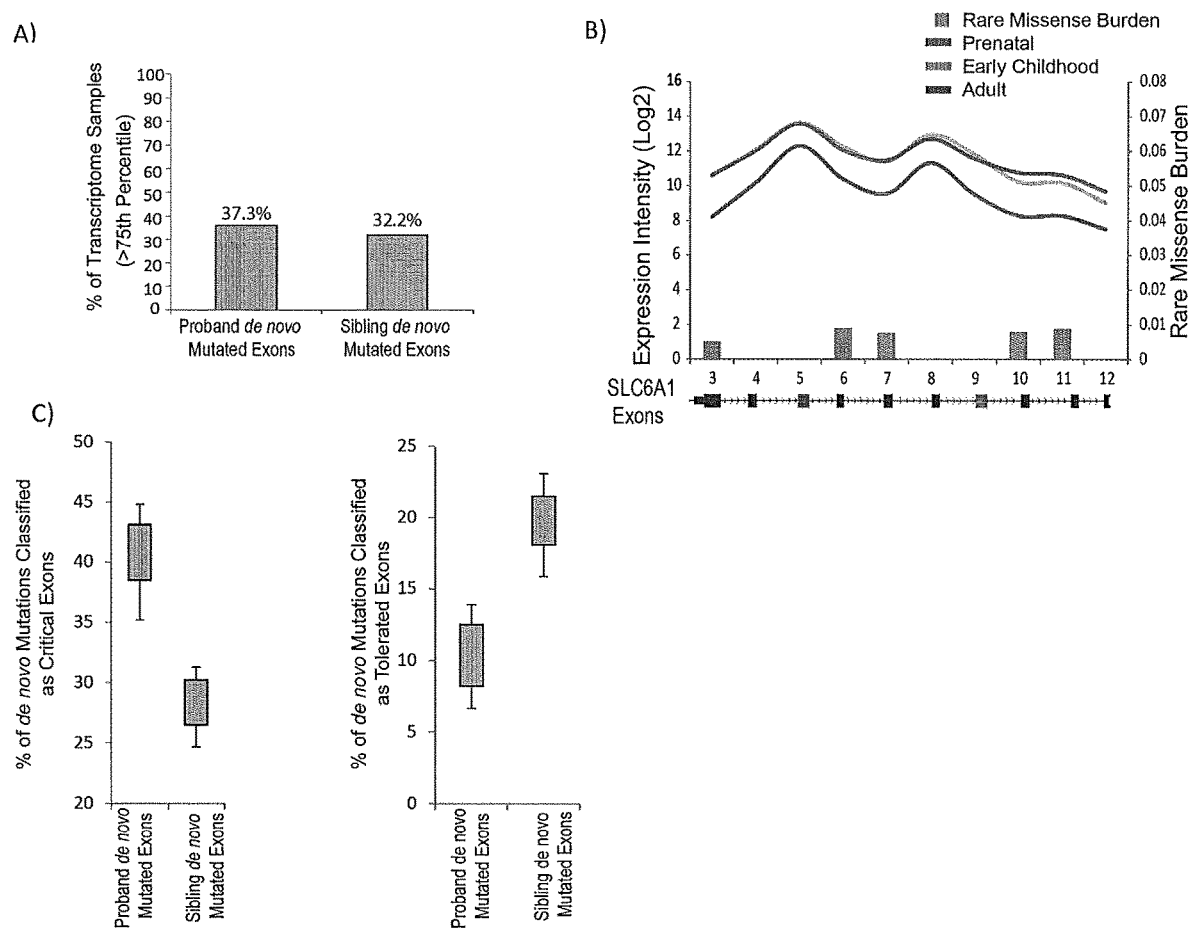
FIG. 9. Highly expressed exons with de novo mutations. A) percentages of brain tissues that have high expression (>75th percentile) of the exons comprising de novo mutations that were ascertained in cases and unaffected siblings. B) box plots show the percentages of de novo mutations (for cases and unaffected siblings) that can be classified as critical exons (left) or tolerated exons (right) using all transcriptome samples. Each confidence interval represents the fraction of variability in the number of critical or tolerated exons obtained from different transcriptome samples (interquartile range (IQR) is between the first and third quartiles). C) the burden of rare missense mutations and expression in human developing brain of the SLC6A1 gene, for which mutated exons have been reported in ASD cases. To capture the exon inclusion/exclusion event for the mutated exons in prenatal brain and adult brain, RT-PCR assays were designed considering various combinations of the flanking exons. Exclusion events (defined by a line for an exon) were confirmed by Sanger sequencing (Table 5). Partial exclusion of exon 3 of the SLC6A1 gene was also captured owing to the variable length of this exon in different isoforms.
Figure 10:
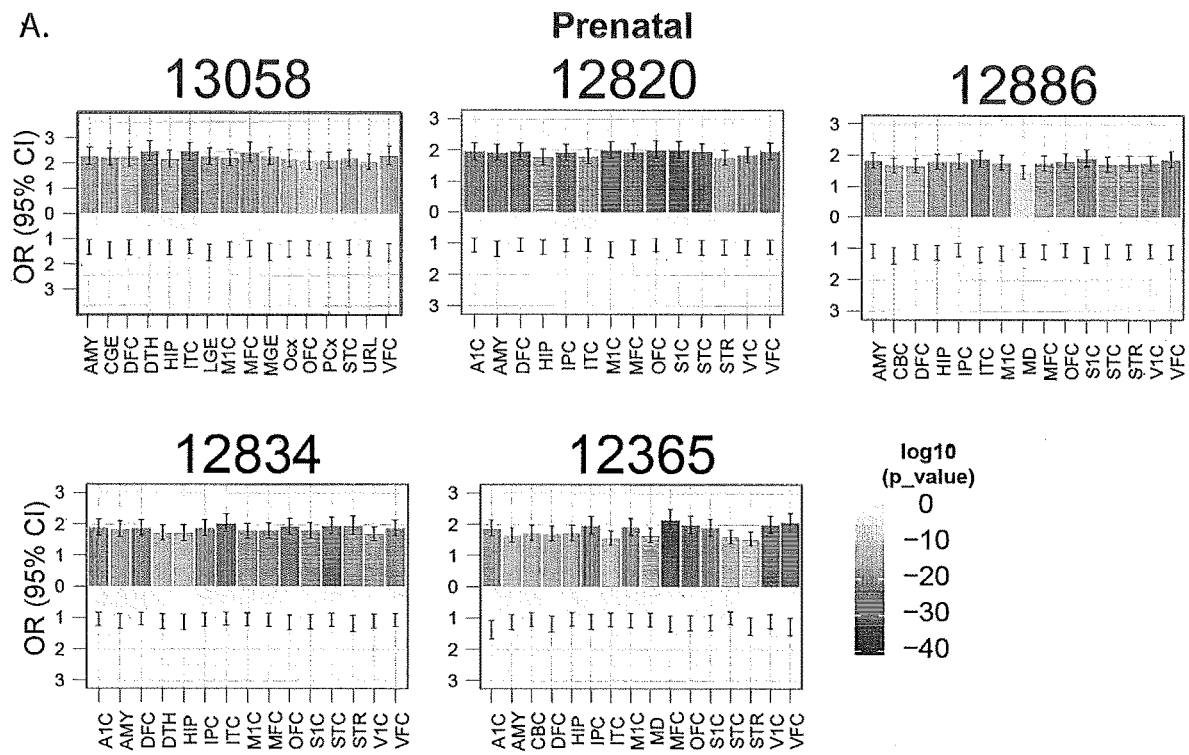
FIG. 10. Validation of RNA-seq for de novo proband and sibling gene. Spatio-temporal association analysis where –log(P) value is represented by color intensities and the odds ratio (OR, 95% CI) on y-axis for genes reported to have de novo mutations in ASD probands (upward bar graph) and unaffected siblings (inverted bar graph) within three developmental time periods: (A) Prenatal, (B) early childhood and (C) adult samples. Similar to microarray data (FIG. 2A), we have observed strongest association within neocortex prenatal samples (Bonferroni corrected, $p<7.8\times10^{-28}$; OR=2.142).
Figure 10:
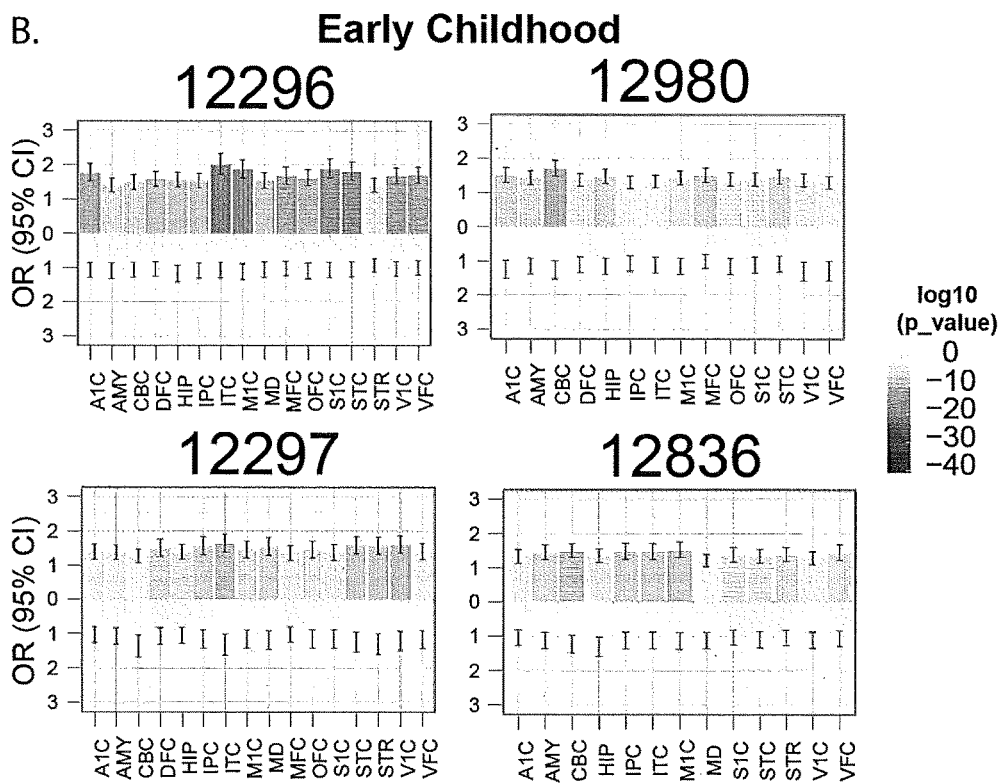
Figure 10:
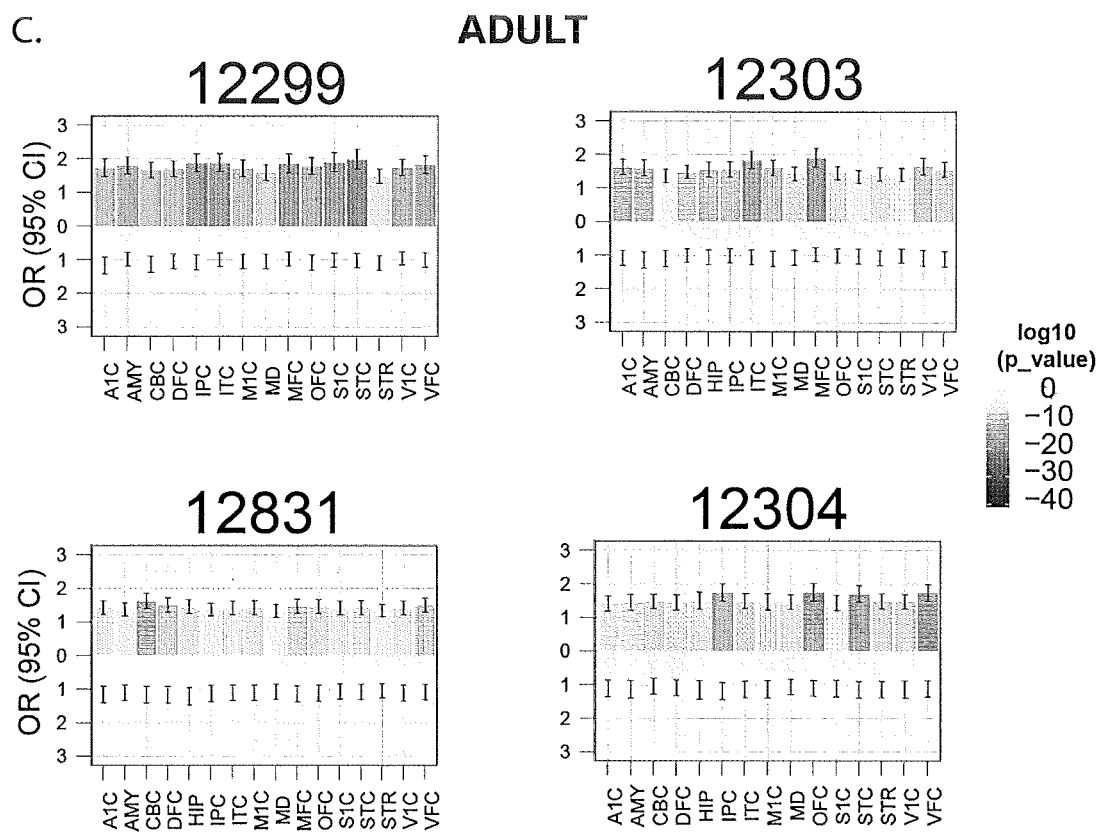
Figure 10:
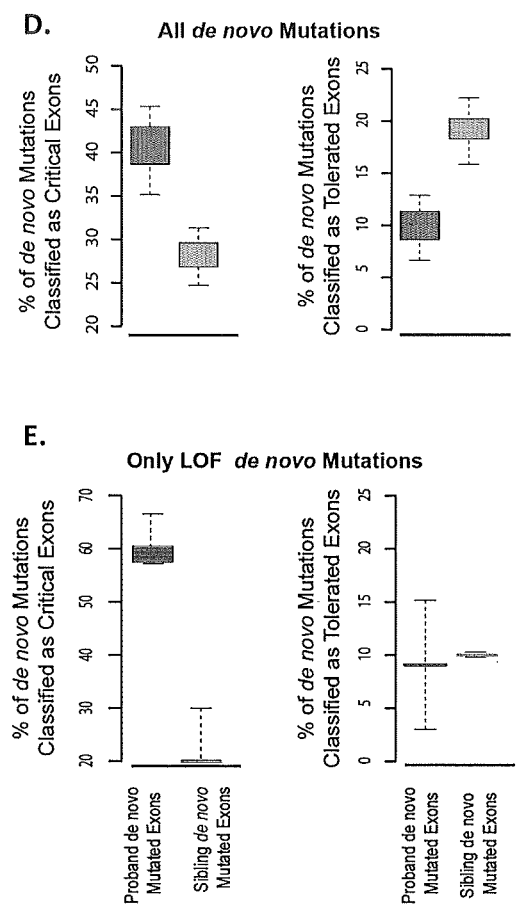

The initial analysis between the ASD case and sibling genes showed identical conservation scores and no significant difference in the distribution of the burden of rare missense mutations (FIG. 6-7). In addition, when it wasted if the de novo mutations in these gene induce aberrant-splicing pattern using the 'splicing code', again no significant difference was found (FIG. 8). However, the inverse correlation was found to be strikingly significant within spatio-temporal brain microarray-based transcriptome datasets (i.e. from control samples) for genes with de novo mutations ascertained in ASD probands (Spearman's Correlation Test, Bonferroni corrected; $p<2.0\times10^{-16}$). No association was detected for genes ascertained through unaffected siblings (FIG. 3C). A similar pattern of inverse correlation for ID and SZ de novo mutated genes was also observed (FIG. 3C). Applying a $75^{th}$ percentile contingency index, the strongest association of genes in ASD cases (FET, Bonferroni corrected; $p<1.13\times10^{-38}$; OR=2.40) was observed for the expression levels in prenatal neocortex samples (FIG. 9A); no association was observed in any brain expression data within ASD siblings genes. The association for the ASD case genes was validated using RNA-sequencing transcriptome data (FIG. 10).

Figure 11:
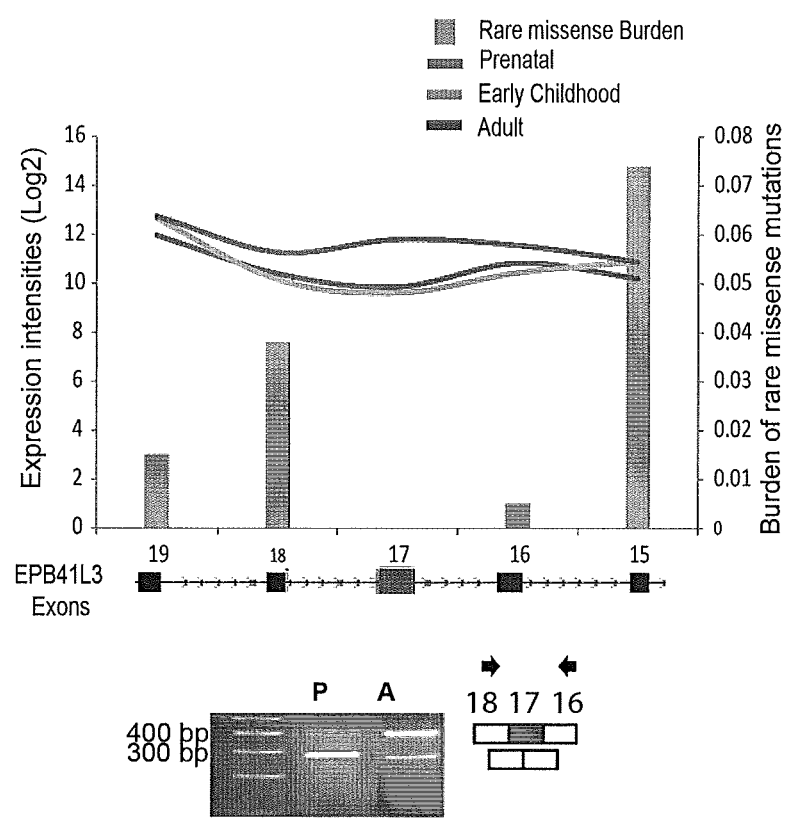
FIG. 11. Exon skipping event for a loss of function (LOF) mutation reported in an unaffected sibling. Exon 17 (highlighted red) reported in sibling gene (EPB41L3) show frequent exclusion mostly in prenatal and adult brains. The exclusion event was confirmed by Sanger sequencing.

When restricting the analysis only to exons with de novo mutations ascertained from ASD cases and siblings, significant differences were observed in expression pattern with respect to high and low rare missense mutation burden (FIG. 9B), predominantly for prenatal samples (Wilcoxon test, Bonferroni corrected; $p<6.06\times10^{-40}$). In one example, reverse transcription-polymerase chain reaction (RT-PCR) confirmed the inverse correlation of missense burden and expression level of exons 5 and 9 in SLC6A1 (for which de novo mutations are reported in ASD probands) including evidence that these are not subject to splicing in normal prenatal or adult brain (FIG. 9C). However, the exons with de novo mutations found in unaffected siblings have a different non-specific pattern (FIGS. 9B and 11). It was confirmed that exons prone to differential usage do not represent a significant determinant driving our association signal.

When restricting the analysis to exons with de novo mutations ascertained in ASD cases and in siblings without ASD, 37.3% and 32.2% of the 196 brain samples, respectively, showed high expression (above the 75th percentile) (FIG. 9A). The presence of a roughly equal rate of de novo mutations in cases and siblings within these exons that are highly expressed in the brain makes it difficult to distinguish actual mutational effects. However, when the transcriptome-mutation contingency index was applied, a difference was found (predominantly for prenatal transcriptome samples), whereby 116 of 256 (45%) exons affected by de novo mutation in cases and 24 of 84 (28%) exons affected by de novo mutation in unaffected siblings were classified as critical exons. In contrast, a two-fold excess of de novo mutations classified as 'tolerated' was found in siblings (FIG. 10D). Considering loss-of-function mutations only, the enrichment was three-fold for critical exons in cases (FIG. 10E).

Figure 13:
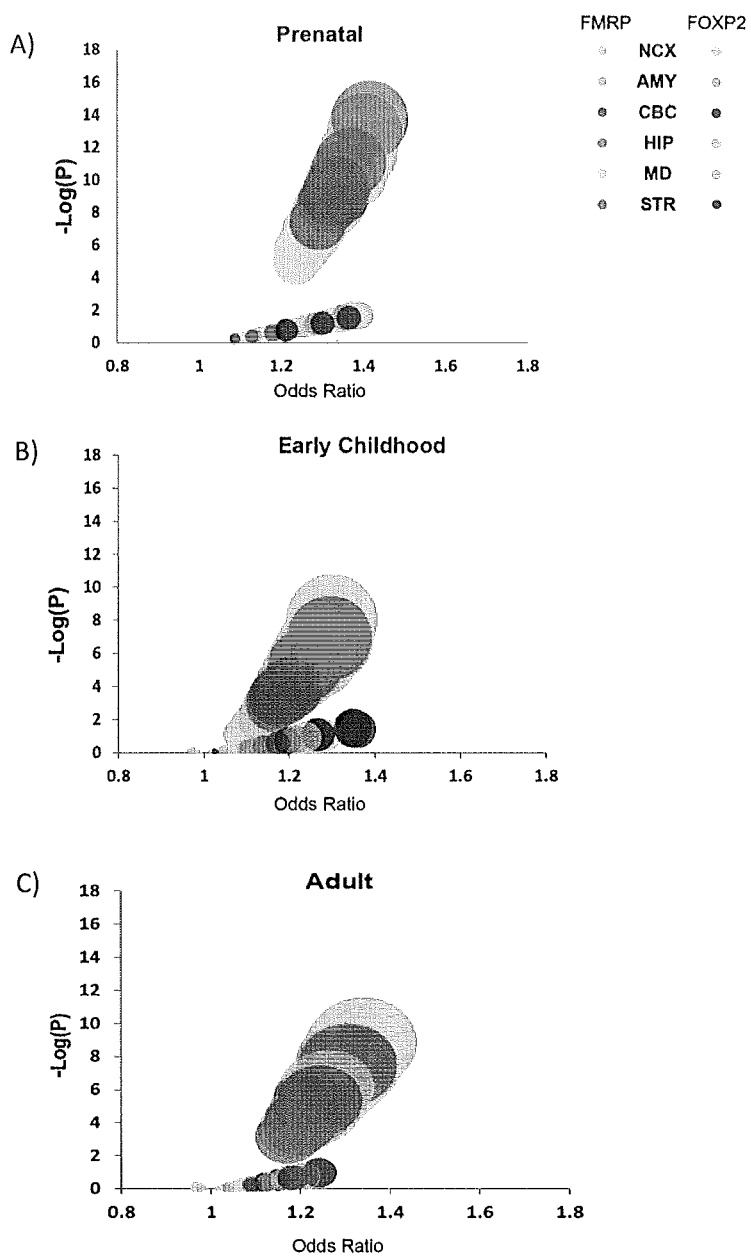
FIG. 13. The association between burden of rare missense mutations and expression in various prenatal (A), early childhood (B) and adult (C) brain tissues for fragile X mental retardation protein targets (FMRP) and forkhead box P2 (FOXP2) targets. The plot shows significant association (–log(P)—Fisher exact test in y axis; odds ratio (OR)—in x-axis) for FMRP targets (color circles) but not for FOXP2 targets that show evidence of positive selection (grey circles). Size of each circle represents the computed odds ratio.

Building from the ASD, ID and SZ findings, a more general grouping of genes involved in brain disorders was tested (termed nervous system abnormalities in the Online Mendelian Inheritance for Man) for a similar inverse correlation with exon expression. A positive association was observed ($p<1.2\times10^{-9}$; OR=1.73) in cerebellum (amongst 11 tissues examined) for autosomal dominant disease genes (FIG. 12). Further analysis revealed an association in genes under purifying selection (FIG. 13).

For CNV analysis, de novo calls from the Autism Genome Project (AGP) Consortium (Stage 1 and 2 and two independent SSC cohorts (SSC1 and SSC2) were used. The combined AGP stage 1 and 2 data (2,446 ASD cases and 2,640 controls), included 101 de novo validated CNVs (losses and gains) (affecting 886 genes in cases and 544 genes in controls). The SSC cohort data included 64 de novo calls (affecting 497 genes) in SSC1 and 75 de novo CNVs (affecting 993 genes) from SSC2. As with findings for de novo SNV/indel mutations, striking associations were observed between microarray-based expression and rare missense burden in control spatio-temporal brain tissues for genes ascertained through de novo CNVs in ASD cases (FIGS. 14 and 15A). The strongest association was found for prenatal neocortex samples (FET, Bonferroni corrected, $p<8.06\times10^{-16}$; OR=1.47). The lack of significant association for CNVs ascertained in controls implies that only de novo CNVs from cases harbor genes enriched with exons that follow the correlation principal between expression and rare missense burden. The association using RNA-sequencing transcriptomes for all three CNV data sets was also validated (FIG. 16).

Since these de novo CNVs typically encompass more than one gene (average: AGP=9 genes; SSC1=8 genes; SSC2=13 genes) a core of dose-sensitive genes were producing the signals. Thus, the analysis was further restricted to CNVs involving single gene losses, and overall higher odds ratios was observed for those ascertained in cases than in controls (FIG. 17), reminiscent of what was observed using the de novo SNV and indel data.

To develop a resource for potential discovery of neuronal disease genes, the inverse correlation framework was applied to multiple transcriptome datasets and 3,955 'critical exons' (from 1,744 unique genes) with high expression specific to brain and low rare mutation burden (2-fold greater expression in brain over that of most other tissues— testis being the exception and similar to brain) were identified (FIG. 18 and Table 7). Such exons are present in most transcripts of their respective genes and functional or splicing mutations in these regions may be manifest as various disorders of the brain. For example, RBFOX1 and its downstream regulatory targets ATP2B1 and GRIN1 were identified in this brain-specific critical exon dataset and this pathway has recently been found to be dysregulated in ASD. Moreover, SHANK1, SHANK2, NRXN2, NRXN3, SCN2A, FMR1, AFF2 and AUTS2 genes, known to confer risk of ASD were also found to be enriched with brain-specific critical exons (transcriptome data were not available for NRXN1 and SHANK3).

Biological pathways were analyzed using the FET to look for potential enrichment (considering two backgrounds, first, entire RefSeq exons and second, only brain expressed exons) of the 3,955 critical exons in candidacy tier datasets comprised of Fragile X mental retardation protein (FMRP) targets, the post-synaptic proteome (PSP), bona fide ASD risk genes (autosomal dominant (AD) and X-linked (XL)), and genes affected by predicted deleterious de novo mutations from ASD trio studies. Indeed, highly significant enrichment of critical exons was detected for the FMRP targets: 41.8% (Bonferroni corrected FET; $p<2.91\times10^{-157}$, OR=9.52), PSP: 28.11% ($p<7.190\times10^{-54}$; OR=4.43), ASD (AD/XL): 34.56% ($p<3.40\times10^{-11}$; OR=6.08) and de novo mutation genes in ASD probands: 25.5% ($p<7.73\times10^{-13}$; OR=3.31)(FIG. 15B). Empirical p-values from 10,000 permutations (from both background) also showed significance after correction for Benjamin-Hochberg false discovery rate (FDR). As a negative control, an equal number of exons (3,955) that are enriched for rare missense mutations (tolerated in control brain tissues) and highly expressed in brain were analyzed. Enrichment re-analysis showed no significance after conducting permutation tests on two backgrounds (Table 8).

TABLE 8

Enrichment Analysis for Exons Highly Enriched with Burden of Rare Missense
Equal number of exons were analysed (3955 exons) where burden of rare missense mutation is high. Following is the Fisher's Exact Test and empirical significance (using two background) of enrichment after 10,000 permutation for FMRP, Post-synaptic Proteome, ASD (AD, XL) and de

| Gene Categories | Background | FET P | Empirical P (10,000 Permutation) | Empirical P (Corrected) |
|---|---|---|---|---|
| FMRP | Refseq | 6.70E−05 | 1 | 1 |
| FMRP | Brain Expressed | 0.000677025 | 1 | 1 |
| Post-Synaptic Proteome | Refseq | 0.03616252 | 0.97 | 1 |
| Post-Synaptic Proteome | Brain Expressed | 0.454409035 | 0.99 | 1 |

TABLE 8-continued

Enrichment Analysis for Exons Highly Enriched with Burden of Rare Missense
Equal number of exons were analysed (3955 exons) where burden of rare missense mutation is high. Following is the Fisher's Exact Test and empirical significance (using two background) of enrichment after 10,000 permutation for FMRP, Post-synaptic Proteome, ASD (AD, XL) and de

| Gene Categories | Background | FET P | Empirical P (10,000 Permutation) | Empirical P (Corrected) |
|---|---|---|---|---|
| ASD (AD, XL) | Refseq | 0.801966304 | 0.73 | 1 |
| ASD (AD, XL) | Brain Expressed | 0.887460535 | 1 | 1 |
| SNV | Refseq | 2.33E−06 | 0.5 | 1 |
| SNV | Brain Expressed | 0.000677025 | 0.99 | 1 |

1,744 genes encompassing these 3,955 critical exons for enrichment in specific functional or biological pathways (stringent cutoffs of $p<1.0\times10^{-3}$; FDR of <0.01) were examined. Gene sets were downloaded from multiple databases: gene ontology (GO), pathways from the National Cancer Institute at the National Institutes of Health (NCI-NIH), Kyoto Encyclopedia of Genes and Genomes (KEGG) and Reactome. FET was used to determine the significance of the enrichment for a given pathway. The test evaluated the enrichment of genes in a pathway against a common background consisting of all the genes in the data set. From the null distribution of p-values, FDR was computed using the Benjamini-Hochberg procedure. A gene-set was considered to be significantly enriched when FET $p<1.0\times10$-3 and FDR<0.01. The results revealed a modular network involving neuronal synapse regulation, neuron differentiation, signaling complexes and synaptic vesicles (FIG. 15C, Table 9). These findings, which were generated without prior knowledge of ASD disease genes, overlap with results obtained using other datasets derived from known ASD genes.

These 1,744 genes represent high priority candidates to be susceptibility loci for ASD and/or related disorders. Of these, 518 (29.7%) genes have already been implicated as candidate genes for neuropsychiatric diseases (Table 7). It was therefore examined whether the brain-specific critical exon index might help to differentiate the specific etiological gene(s) from mere bystanders co-located within genomic CNV loci that are well documented to be involved in ASD. At the 16p11.2 CNV (~600 kb encompassing 29 genes) four genes (PRRT2, SEZ6L2, ASPHD1, KCTD13) were identified harboring critical exons (FIG. 19); three of these have been implicated within the smallest region of overlap identified by atypical cases with smaller deletions (FIG. 19). All four genes are implicated through functional and large phenotypic analyses to be relevant to ASD or other neuropsychiatric phenotypes. The present analysis identified other candidate genes for neuronal phenotypes from disease loci: 3q29 micro-duplication/deletion (PIGZ, DLG1), 17q21.31 micro-deletion syndrome (CRHR1, MAPT), 17q11.2-NF1 micro-deletion syndrome (NF1, RAB11FIP4) and 22q11.2 micro-duplication/deletion syndrome (ARVCF, DGCR8, ZDHHC8, PI4KA) (FIGS. 20 and 21).

The development of exon transcriptome/mutation contingency index provides a new approach to prioritize putative mutations for subsequent clinical- and functional-genetic analyses. Applying this strategy permits unprecedented specificity and clarity to re-analysis of mutation data, helping to redefine the genes, sites within genes, and molecular pathways involved in the disease processes. These studies of ASD have yielded the most significant data so far, most likely because of the greater maturity of datasets available for this disorder. From an evolutionary perspective, there seems to be selective pressure for specific neuronal genes (the data suggests at least 1,744 of them) to maintain the integrity of particular exons (3,955). The data indicates that as mutations are identified and proven, through functional studies, to be etiologic for brain disorders—e.g. for ASD, they will be found to have arisen in genes having the properties identified here. Moreover, the impact of upstream mutations that lead to some form of alteration of the 'critical exon', as well as more subtle mutations, with direct and indirect effects of modifier genes can also now be modeled within this framework. Ultimately, exploiting this new understanding of the role of the brain transcriptome in modulating mutational impact will facilitate more accurate genotype and phenotype studies in ASD and related disorders.

Example 2

Copy number variants (CNVs) are associated with numerous neurocognitive disorders. In a diagnostic setting, clinical microarray commonly uses ISCA 4×180K arrays to detect such chromosomal abnormalities. The variants are classified primarily into three distinct groups: "pathogenic", "variant of unknown significance (VOUS)", or "benign/control". However, "pathogenic" events are typically large, and the underlying causative genes are unclear. The genotype-phenotype correlation is also complicated for VOUS variants due to lack of additional support to interpret the variant.

Using 7,106 samples from individuals with developmental delay (obtained from the Hospital for Sick Children, Toronto, molecular diagnostic laboratory), the samples were genotyped using the International Standards for Cytogenomic Arrays (ISCA). CNVs were primarily classified into the three groups mentioned above. 7,646 control CNVs detected from other high-resolution microarray experiments were also utilized.

The data were analyzed as described in Example 1 using the mutation-transcriptome contingency index method for 'critical exon' enrichment. Using this method, 226,845 exons of the genome were processed. For each exon, the rare missense/LOF mutation burden was computed, and transcriptome was quantified for each exon based on prenatal brain expression data from Brain Span database. In this cohort, the "pathogenic", "VOUS" and "control" loss variants impacted 61,000, 12,147, and 11,046 exons of the genome, respectively. The "critical-exon" enrichment analysis revealed strikingly significant (FET test p-value) differences between pathogenic, VOUS and controls (FIG. 22). The proportion of exons classified as 'critical-exon' within pathogenic and VOUS groups was within ~17-19%, whereas the controls were classified only for ~7-9%. These findings are consistent with previous results.

Example 3

Clinical Microarray Datasets

Clinical microarray (CMA) data was obtained from two independent sites, The Hospital for Sick Children (SK) and Credit Valley Hospital (CVH). A total of 7,106 and 3,513 cases CMA data were obtained, respectively, that went through confirmed diagnosis for developmental delay. ISCA 180K comparative genomic hybridization array was used to detect large CNVs by applying a circular binary segmentation algorithm. For reference, a pool of 10 samples was used to compare individual probe intensities. The clinical annotation for each sample variant was conducted by the clinical geneticist in each site.

DNA extracted from peripheral blood was used to perform comparative genomic hybridization array (aCGH) analysis on a custom designed 4×180K oligonucleotide microarray platform (Oxford Gene Technology (OGT), Oxford, UK). Microarray experiments were performed according to the manufacturer's instructions. Briefly, DNA from the proband and pooled same-sex reference DNA (Promega, Madison, Wis.) were labeled with Cy3-dCTP and Cy5-dCTP, respectively, and were hybridized to the array slide according to the manufacturer's protocol (OGT). The arrays were scanned using the Agilent G2505B microarray scanner. Data analysis was performed using the Agilent Feature Extraction software (10.7.11) and CytoSure Interpret Software version 3.4.3 (OGT). Clinical interpretation of copy number variants was consistent with the ACMG guidelines. Parental follow-up studies were performed by FISH analysis on cultured lymphocytes using standard protocols. Metaphase chromosomes were counter-stained with DAPI, and inverted grey scale imaging was used to visualize chromosome banding patterns for chromosome identification, using the ISIS Metasystems imaging software version 5.5.4 (Newton, Mass., USA). Parental follow-up of deletions less than 200 kb and duplications less than 700 kb were performed by aCGH.

9,692 unrelated control samples were used from multiple major population scale studies that used high-resolution microarray platform. These samples did not have any obvious psychiatric history. The studies include 4,347 control samples assayed in Illumina 1M from the Study of Addiction Genetics and Environment (SAGE) and the Health, Aging, and Body Composition (HABC); 2,988 control samples assayed in Illumina Omni 2.5M from COGEND and KORA projects; 2,357 control samples assayed in Affymetrix 6.0 from Ottawa Heart Institute (OHI) and PopGen project. An additional 11,255 control datasets assayed in Illumina platforms from ARIC and WTCC2 project were also incorporated.

Critical Exon Classification—

For critical exon classification as described in Example 1, the 1000 genome project for rare missense loss of function (LOF) mutation burden computation and transcriptome data from the human developmental brain atlas was used.

Burden of Rare Missense Mutations—

Data from the 1000 genome project initiated by the US National Health Heart, Lung and Blood Institute (NHLBI) was used to calculate the burden of rare missense mutations in human populations, including 1,039 whole genome sequencing samples (495 males, and 544 females). Within these whole genome sequenced (WGS) samples, exonic regions had mean coverage of at least 20×. The RefSeq gene annotation model (which includes all exons from annotated isoforms) was used for the analysis. Genes with no variant calls were excluded. As described previously, variants were annotated using Annovar and considered rare missense and loss of function (LOF) variants as strong proxy for recent (mostly within the last 5,000-10,000 years) rare deleterious mutation events in humans.

Spatio-temporal Human Brain Expression—The normalized RNA-seq expression profiles of spatio-temporal developmental human brains were downloaded from the Brain-Span database). 394 tissue samples from 31 post mortem donors (prenatal and adult) were analyzed. The expression measures were provided for exons as reads per kilobase (kb)

per million (RPKM) from mapped reads. Method details for sequencing, alignment, QC and expression quantification can be found in the BrainSpan Technical White Paper. The spatial-temporal (prenatal and adult) analysis was conducted on 16 brain regions, including 11 neocortex regions (V1C, primary visual cortex; STC, posterior (caudal) superior temporal cortex; 1PC, posterior inferior parietal cortex; A1C, primary auditory cortex; S1C, primary somatosensory cortex; M1C, primary motor cortex; DFC, dorsolateral prefrontal cortex; MFC, medial prefrontal cortex; VFC, ventrolateral prefrontal cortex; OFC, orbital frontal cortex; ITC, inferolateral temporal cortex) and AMY, amygdaloid complex; CBC, cerebellar cortex; HIP, hippocampus; MD, mediodorsal nucleus of thalamus; and STR, striatum. To classify critical exons, the 75th percentile value was computed from the entire dataset and used as a threshold to define exons with high and low expression, according to steps 102, 103 in FIG. 30A. Critical exon fraction was computed for a gene or a group of genes (impacted by CNVs) by applying the 75th percentile index on all exons. The fraction was computed by dividing the number of exons classified as critical exon over total number of exons.

Human Developmental Protein Expression Data—

The protein expression levels for the genes were analyzed using high-resolution genome-wide Fourier-transform mass spectrometry data (as described in Kim et al. *Nature* 509, 575-81 (2014) and downloaded from Human Proteome Map). An in-depth proteomic profiling of 30 histologically normal human samples was conducted, including 17 adult tissues (lung, heart, liver, gall bladder, adrenal gland, kidney, urinary bladder, prostate, testis, ovary, rectum, colon, pancreas, oesophagus, retina, frontal cortex, and spinal cord) and 7 fetal tissues (liver, heart, brain, placenta, gut, ovary, testis). High-resolution Fourier transform mass spectrometers was used for fragmentation (high-high mode) to process the data. The data resulted in the identification of proteins encoded by 17,294 genes accounting for approximately 84% of the total annotated protein-coding genes in humans. Average spectral counts per gene per sample were used as the measure for protein expression.

WGCNA Network Details—

Weighted gene co-expression network analysis (WGCNA) analysis was conducted by computer using human protein expression data in development, in accordance with step 102 of FIG. 30A. The R WGCNA package was used to conduct the analysis (as described in Langfelder et al. *BMC Bioinformatics* 9, 559 (2008); and Langfelder et al. *J Stat Softw* 46 (2012)). The use of weighted networks represents an improvement over unweighted networks because it preserves the continuous nature of the co-expression information and it is biologically robust with respect to parameter β (as described in Zhang et al. *Stat Appl Genet Mol Biol* 4, Article 17 (2005)). Proteins that are not expressed (expression=0) in at least 90% of the samples were excluded because such low-expressed features tend to reflect noise and correlations based on counts that are generally zero and thus not meaningful. The absolute value of the Pearson correlation coefficient is calculated for all pair-wise comparisons of protein expression values across all developmental tissue samples into a similarity matrix. Blockwise network construction and module detection method were used where the clustering of a block consisted of a maximum of 20,000 proteins. A signed adjacency matrix was constructed using a "soft" power adjacency function $a_{ij}|=0.5+0.5*cor(x_i, x_j)|^\beta$ where the absolute value of the Pearson correlation measures the protein co-expression similarity, and $a_{ij}$ represents the resulting adjacency that measures the connection strengths. The soft thresholding beta=18 was chosen based on the scale-free topology criterion β for the analysis. Next, to compute modules, where the proteins have high "topological overlap", connection strength between proteins in the network was compared. The parameters for module detection used—were: minimum 30 proteins per module and a medium sensitivity deepsplit=2 was applied to cluster splitting. The clustering of genes for modules used average linkage hierarchical clustering and modules were identified in the resulting dendrogram by the dynamic hybrid tree cut. Found modules were trimmed of genes whose correlation with module eigengene (KME) is less than a threshold defined by the function minKMEtoStay and for merging similar modules, 0.35 was used as a threshold. The connectivity of each node i is the sum of connections to other nodes.

For visualizing the protein co-expression network, Cytoscape network software v.2.8.3 was used. The nodes were represented by a circle and the edge between the nodes implies the co-expression weighted Pearson distance. The color of the node is representative of their membership to a phenotype.

Significant Test Analysis and Permutation Test—

Fisher's exact test (FET) was used for all count data and gene enrichment test with p-value <0.05 (after Bonferroni multiple test correction) was used as the threshold for significance. To reveal the strength of enrichment association with the gene lists, a permutation test was conducted by randomly drawing equal numbers of genes and re-analyzing the data under the null-hypothesis. The random draw was conducted from a background that is appropriate for the test. With sufficient iterations (100,000 times), the resulting sets of p-values were presumed to be a reasonable approximation of the null distribution of the p-values.

Reverse Transcription Polymerase Chain Reaction (RT-PCR) and Quantitative RT-PCR (qRT-PCR)—

For the quantification of 'critical exons' by qRT-PCR, primers were designed to prime from within the specific exon (Table 9). The primers were tested for their PCR efficiency by dilution standard curve and for specificity with melting curve analysis using adult whole brain cDNA. To quantify the 'critical exon' expression from selected genes, RNA was used from a panel of 11 human tissues: liver (BD Biosciences), kidney (Stratagene), mammary gland (BD Biosciences), cerebellum (Clonetech), skeletal muscle (Stratagene), prostate (Clonetech), spleen (Stratagene), thyroid (Stratagene) and testis (Clonetech). Reverse transcription was performed using the Superscript III First strand Synthesis Supermix (Invitrogen). Using 10 ng of cDNA as template, RT-PCR was performed under standard PCR conditions using Brilliant III SYBR® Green PCR Master Mix (Agilent) and the MX300 software (Agilent). Gene expression was normalized using MED13 or ACTB (dCt) and quantified as relative expression ($2^{\wedge}(-dCt)$).

TABLE 9

Primer sequences for quantification of critical exons within MVB12B, PPP1R9A, and GIT1 genes

| Primer Name | Sequence (5'-3') |
|---|---|
| MVB12B-F | TTC ATC CCA ATT CAG GAG AC (SEQ ID NO: 25) |
| MVB12B-R | CAT GAT CCG AAT GTC ACA AA (SEQ ID NO: 26) |

TABLE 9-continued

Primer sequences for quantification of critical exons within MVB12B, PPP1R9A, and GIT1 genes

| Primer Name | Sequence (5'-3') |
|---|---|
| PPP1R9A-F | AGC AGG TTT CTC ACT GGT TA (SEQ ID NO: 27) |
| PPP1R9A-R | GAT GCT GTC ATT CCA AGA GC (SEQ ID NO: 28) |
| GIT1-F | GCC TTG ACT TAT CCG AAT TG (SEQ ID NO: 29) |
| GIT1-R | ACC TCG TCA TAC ACG TCC A (SEQ ID NO: 30) |
| ACTB-F | ATT GCC GAC AGG ATG CAG A (SEQ ID NO: 31) |
| ACTB-R | GAG TAC TTG CGC TCA GGA GGA (SEQ ID NO: 32) |
| MED13-F | CCG CAT CCT GAT GTG TCT GA (SEQ ID NO: 23) |
| MED13-R | TTG CAG GTG GAT ACG TGA CT (SEQ ID NO: 24) |

Results 10,619 cases were analyzed from two hospitals (The Hospital for Sick Children (SickKids) and Credit Valley Hospital (CVH), Ontario) referred for clinical laboratory testing due to developmental delay. Also, 9,692 controls where no known psychiatric condition has been reported for the samples were assayed (FIG. 23). From this developmental delay cohort, 10.15% of the samples carried a pathogenic CNV, and 50.25% had at least one rare VOUS (variant of unknown significance) (FIG. 24A). In the SickKids subset (7,106 cases), which included inheritance information, there were 169 de novo variants from developmental delay cases (108 deletions and 61 duplications), of which 64% (108/169) were interpreted as pathogenic and 36% (61/169) as VOUS. The analysis was restricted to variants of 30 Kb to 5 Mb in length. The developmental delay cohort was 68.53% male and 31.46% female. There were pathogenic deletion variants in 5.26% of females and 3.69% of males, and this difference was highly significant (p<0.0002) (FIG. 24B). This gender difference was not found for duplication CNVs. The average number of genes with exonic variants differed significantly between pathogenic CNVs and VOUS. Genes per variant averaged 38 for pathogenic duplications, 27 for pathogenic deletions, 4.6 for VOUS duplications, and 3.2 for VOUS deletions. The average number of genes in pathogenic deletions from females was higher than in those from males. CNVs at loci for known genomic disorders were more frequent in the developmental delay cohort relative to controls, for example 16p11.2 (0.86%), 15q13.3 (0.43%), Prader-Willi syndrome (0.52%) and 22q11 deletion/duplication syndrome (1.06%).

Genes within pathogenic or VOUS CNVs in this developmental delay cohort, had a significantly higher fraction of critical exons (computed over all exons impacted by CNVs), compared with genes in rare duplications or deletions in controls. Gene sets from pathogenic CNVs and VOUS were very large, and overlapped those from control CNVs and so the analysis was limited to genes impacted by pathogenic CNVs or VOUS from the case cohort, and not found in unaffected controls (FIG. 25). A striking enrichment of critical exons (computed using prenatal brain transcriptome) within pathogenic deletions (corrected Fisher's Exact Test (FET within 16 brain regions ranged from $P<1.64\times10^{-15}$ to $1.31\times10^{-299}$) and VOUS deletions ($P<1.31\times10^{-20}$ to $6.22\times10^{-158}$) was observed (FIG. 25A). This result strongly suggests that pathogenic and VOUS variants harbor more critical exons than the rare CNVs in controls. Although deletions showed the consistently highest sensitivity, a similar increased critical exon fraction for pathogenic and VOUS duplications computed using prenatal and adult transcriptome was observed (FIG. 25A). Exclusively pathogenic and VOUS gene sets were then used to identify candidates for effects on developmental disorders. Of interest, the fraction of critical exons was highest in prenatal neocortical regions (specifically medial prefrontal cortex (MFC) tissues) for genes impacted by either pathogenic or VOUS deletions. This observation strongly supports previous independent reports of multiple neuropsychiatric patients with altered MFC functional activity.

To examine the biological relevance of pathogenic and VOUS 'critical exons' at the protein level, a co-expression analysis was applied using Fourier transformed protein expression data. A draft map of the human proteome reported by Kim et al. (Nature 509, 575-581) obtained from mass spectrometry of 24 different human tissues (each pooled from 3 post-mortem samples) including 17 adult and 7 prenatal, was used. This is the first such human developmental protein co-expression analysis. Unlike the biased seeding approach used to construct modules and networks, an unbiased construction of networks was implemented, based on spatio-temporal protein expression, by applying a weighted gene coexpression network analysis (WGCNA). WGCNA was applied to the 17,294 genes represented by the proteome (Jiang et al. American journal of human genetics, (2013); published online EpubJul 10 (10.1016/j.ajhg.2013.06.012) to construct protein co-expression networks. Genes not expressed in at least 90% of the tissues were excluded. The analysis revealed networks for 23 independent protein expression modules (FIG. 26A). To identify modules that are relevant to developmental delay, gene enrichment analysis was conducted using 18,826 gene ontology (GO) terms, and retained the 20 most significant GO terms. From this analysis, the 'blue' module was identified (FIG. 26A), which comprised 2,484 genes, and was highly significant ($P<1.0\times10^{-39}$ to $1.0\times10^{-81}$) for pathways involved in synaptic transmission, neuron projection, cell signaling, nervous system development and axon guidance (FIG. 26B).

To develop a list of candidate genes related to developmental delay, the two approaches, critical exon and WGCNA core protein, were combined, analyzing genes from the protein-derived 'blue' module for critical exon enrichment. For each gene in the genome, the critical exons for prenatal and for adult tissues were computed. To control for the genes with a large number of exons, for each gene in the genome, the fraction of critical exons (over all exons) for a gene in each brain region were computed. For each developmental period (prenatal or adult), a gene was deemed to be significant if its critical exon fraction fell within the genome's top $25^{th}$ percentile for at least 50% of the brain samples (Table 10).

TABLE 10

Clinically relevant genes within known syndromic regions.

| Syndrome | Coordinate | Total Gene | Genes | Blue Protein Network and Critical Exon Enriched Genes |
|---|---|---|---|---|
| 16p11.2 microduplication syndrome | chr16: 29606852-30199855 | 30 | DOC2A, ASPHD1, LOC440356, CORO1A, TBX6, LOC100271831, PRRT2, CDIPT, QPRT, YPEL3, SLC7A5P1, PPP4C, MAPK3, SPN, MVP, FAM57B, ZG16, ALDOA, INO80E, SEZ6L2, TAOK2, KCTD13, MAZ, KIF22, GDPD3, C16orf92, C16orf53, TMEM219, C16orf54, HIRIP3 | DOC2A, TAOK2, PRRT2, SEZ6L1, MAPK3, ALDOA |
| Angelman syndrome (Type 1/2) | chr15: 23619912-28438266 | 116 | NIPA2, NIPA1, SNORD116-9, SNORD116-8, SNORD116-5, SNORD116-4, SNORD116-7, SNORD116-6, SNORD116-1, SNORD116-3, SNORD1162, SNORD109A, SNORD109B, GOLGA8IP, PARSN, PWRN1, PWRN2, OCA2, LOC100128714, MIR4508, SNORD115-34, PAR5, PAR4, IPW, PAR1, GOLGA8E, SNORD116--19, SNORD11618, GABRG3, SNORD115-3, SNORD115-31, SNORD64, SNORD115-18, SNORD115-19, SNORD115-14, SNORD115-15, SNORD115-16, SNORD115-17, SNORD115-10, SNORD115-11, SNORD115-12, SNORD115-13, UBE3A, MAGEL2, ATP10A, C15orf2, SNORD115-21, LOC283683, SNORD115-23, SNORD115-22, SNORD115-25, SNORD115-8, SNORD107, SNORD115-26, SNORD115-29, SNORD108, SNORD116-16, SNORD115-20, HERC2, SNORD115-24, SNORD115-27, SNORD115-36, SNORD115-37, MKRN3, SNORD115-35, SNORD115-32, SNORD115-33, SNORD115-30, SNORD115-28, GABRA5, MIR4715, SNORD115-38, SNORD115-39, HERC2P2, HERC2P7, NDN, LOC503519, GABRB3, SNORD115-43, SNORD115-42, SNORD115-41, SNORD115-40, SNORD115-47, SNORD115-45, SNORD115-44, SNORD115-48, TUBGCP5, CYFIP1, SNORD116-24, SNORD116-25, SNORD116-26, SNORD116-27, SNORD116-20, SNORD116-21, SNORD116-22, SNORD116-23, SNORD116-28, SNORD116-29, SNORD115-6, SNORD115-7, SNORD115-4, SNORD115-5, SNORD115-2, SNURF, SNORD115-1, SNORD116-11, SNORD116-10, SNORD116-13, SNORD116-12, SNORD116-15, SNORD116-14, SNORD116-17, SNORD115-9, SNRPN, WHAMMP3, LOC653061 | UBE3A, GABRB3, CYFIP1 |
| Williams-Beuren Syndrome (WBS) and 7q11.23 duplication syndrome | chr7: 72744455-74142672 | 26 | STX1A, WBSCR27, WBSCR22, LAT2, LIMK1, WBSCR28, MIR4284, RFC2, FKBP6, MIR590, FZD9, VPS37D, ABHD11, CLIP2, CLDN3, CLDN4, BCL7B, ELN, MLXIPL, DNAJC30, GTF2IRD1, BAZ1B, TBL2, EIF4H, GTF2I, ABHD11-AS1 | CLIP2, LIMK1 |
| 22q11 Velocardiofacial/DiGeorge syndrome | chr22: 19009792-21452445 | 62 | P2RX6P, RIMBP3, TMEM191A, PI4KA, KLHL22, SLC7A4, LOC388849, MIR185, GNB1L, TBX1, MIR3618, MIR1306, SEPT5, ZNF74, P2RX6, DGCR8, PI4KAP1, DGCR10, TMEM191B, DGCR6, GP1BB, LOC400891, C22orf39, C22orf25, DGCR6L, MED15, CRKL, TXNRD2, CLDN5, LOC150197, RTN4R, TSSK2, GSC2, ARVCF, SLC25A1, MIR4761, COMT, LOC284865, LOC729444, AIFM3, CLTCL1, SERPIND1, THAP7-AS1, SCARF2, HIRA, THAP7, MIR1286, RANBP1, POM121L4P, SNAP29, UFD1L, DGCR11, C22orf29, MRPL40, DGCR14, ZDHHC8, CDC45, TRMT2A, LZTR1, LOC150185, MGC16703, SEPT5-GP1BB | CLDN5, CLTCL1, SEPT5$^{\Psi}$, PI4K2 |
| 3q29 micro-deletion/duplication syndrome | chr3: 195726835-197344663 | 28 | RNF168, NCBP2, LOC100507086, ZDHHC19, DLG1, TM4SF19-TCTEX1D2, TFRC, LOC152217, UBXN7, FBXO45, MIR4797, MFI2, SENP5, OSTalpha, TCTEX1D2, PIGX, PIGZ, LOC220729, BDH1, PCYT1A, WDR53, LRRC33, MFI2-AS1, C3orf43, LOC401109, TM4SF19, CEP19, PAK2 | PAK2$^{\Psi}$ |

$^{\Psi}$deleterious point mutations or focal deletions have been independently reported in cases with developmental delay or related conditions.

48.5% (1,206/2,484) of 'blue' module proteins to be within the top 25$^{th}$ percentile of genes enriched for critical exons, both for prenatal (FET, P<1.15×10$^{-50}$, OR=2.11) and adult brain (FET, P<6.03×10$^{-18}$, OR=1.55). This included genes (SCN2A (MIM: 182390), NRXN1 (MIM: 600565), NRXN2 (MIM: 600566), NRXN3 (MIM: 600567), SHANK2 (MIM: 603290), NLGN3 (MIM: 300336), STXBP1 (MIM: 602926), NLGN4 (MIM: 300427)) known to be associated with neuropsychiatric conditions. Inference of these 1,206 candidate genes, as described, was independent of the knowledge of gene-disease association. The overrepresentation of critical exon genes within the 'blue' module was tested by random permutation 100,000 times to obtain an empirical significance (for both periods, P<1.0×10$^{-05}$) (FIG. 26C-D). The blue module was then tested from within for overrepresentation in tiers of genes that are associated with certain neurodevelopmental disorders. There was significant enrichment of 'blue' module genes with 840 fragile X mental retardation protein (FMRP) target genes (P<1.36×10$^{-128}$, OR=6.25; empirical P<1.0×10$^{-05}$), 246 genes impacted with de novo LOF mutations in ASD cases (P<5.9×10$^{-04}$, OR=1.79; empirical P<2.1×10$^{-04}$) and 141 genes that had de novo exonic deleterious mutations in intellectual disability samples (P<8.0×10$^{-03}$; OR=1.80; empirical P<2.3×10$^{-03}$) from exome and whole genome sequencing. This result suggested that proteins in this 'blue' module are under purifying selection in brain, and that perturbing its components may lead to neurodevelopmental phenotypic manifestations.

Next, 'blue' module genes were searched for among those ascertained from CNVs in the developmental delay cohort. "Blue" module genes were significantly overrepresented among genes within pathogenic deletions (P<2.97×10$^{-09}$; OR=1.58; empirical P<0.024) or duplications (P<0.002; OR=1.24; empirical P<0.006) (1 sided FET and permutation test). They were similarly overrepresented among genes within VOUS deletions (P<7.44×10$^{-07}$; OR=1.48; empirical P<0.002) and duplications (P<0.004; OR=1.14; empirical P<0.023) (FIG. 26E, F). In contrast, the genes within deletions and duplications in controls were not overrepresented within the "blue" module. 438 candidate genes (of 1,206 genes) were found that were included in the 'blue' module and also highly enriched for critical exons (top 25$^{th}$ percentile), that had been ascertained by at least one pathogenic variant or VOUS in the developmental delay cohort. Of these, 65 (14.84%) were seen in at least 2 VOUS deletions in cases but not controls. Another 37 of these 438 genes were impacted by at least one de novo VOUS in the dataset. Genes from large recurrent CNVs known to be associated with neuropsychiatric syndromes (e.g., 16p11.2, 22q11, and 3q29) were represented in the 'blue' protein module and were highly enriched for 'critical exons' in prenatal or adult brain (Table 10).

Through unbiased critical exon analysis coupled with WGCNA network analysis, 1,206 candidate genes were identified whose disruption is likely to contribute to neurodevelopmental delay. For example, VOUS deletions and duplications in the cohort within chromosome region17q11.2 affect the gene for G protein-coupled receptor kinase interacting ArfGAP1 (GM) (MIM: 608434). Within the VOUS in this region, GIT1 was the only gene enriched with critical exons in prenatal brain, and was highly clustered with genes (highly connected first degree neighbors) from within the 'blue' protein module network that were reported to have de novo mutations in ASD. The GIT1 protein is involved in cell migration, localizes in pre- and post-synaptic terminals, and regulates synapse formation. Recent studies of knock-out Git1–/– mice showed a decreased brain size, with impaired motor coordination and deficits in learning and memory. Follow-up analysis on additional human cohorts (Mayo clinic, DatabasE of genomiC varIation and Phenotype in Humans using Ensembl Resources (DECIPHER) and Centre Hospitalier Universitaire Sainte-Justine clinic) found enrichment of CNVs affecting GIT1 among cases (12 deletions and duplications, including 5 de novo; none in controls). The smallest focal deletion of 180 kb was found in an 11-year-old child (FIG. 27A, Table 11, case 6D) referred for developmental delay with epilepsy and attention deficit hyperactivity disorder as comorbid conditions. Another focal deletion was found as a de novo event of 299 kb in a 10-year-old child referred for developmental delay (case 1D-DN). The DECIPHER database showed a similar de novo focal 282 kb deletion affecting a child referred for learning disabilities, dysphasia and poor motor coordination (see phenotype Table 11 case 5D-DN). This source also identified two de novo duplications affecting GIT1: a 1.4 Mb de novo duplication in a patient referred for intellectual disability, and a focal 466 kb duplication in a patient with broader developmental delay. A de novo damaging missense mutation was also reported in a schizophrenia case. Quantitative real-time PCR (rt-PCR) analysis was conducted to quantify relative mRNA expression analysis of GIT1 on 11 human tissues (including prenatal and adult brain) by targeting a critical exon of the gene. GIT1 expression relative to that of the MED13 (MIM: 603808) gene (or to the ACTB (MIM: 102630) gene) showed brain specific expression in prenatal and adult tissue (FIG. 27C).

TABLE 11

Phenotypic table for cases with developmental delay and CNVs impacting GIT1, PPP1R9A, and MVB12B gene. The cases are listed only if the phenotypic information was available.

| Case ID | Critical Exon Gene | Size | Copy Number | CNV (Inheritance) | Age of Ascertainment | Developmental Delay/ID | Dysmorphic Features | Other Clinical Features |
|---|---|---|---|---|---|---|---|---|
| 1D_DN | GIT1 | 299 Kb | Loss | 17q11.2 27.822 to 28.121 Mb (de novo) | 10 yrs | Developmental delay | N/A | |
| 6D | GIT1 | 180 Kb | Loss | 17q11.2 27.733 to 27.913 Mb | 11 yrs | Developmental delay | | Epilepsy, ADHD |
| 5D_DN | GIT1 | 282 Kb | Loss | 17q11.2 27.837 to 28.120 Mb (de novo) | N/A | Learning disability | | Dysphasia |
| 4D_DN | GIT1 | 5.3 Mb | Loss | 17q11.2q12 27.771 to 33.094 Mb (de novo) | 1 yr | N/A | N/A | |

TABLE 11-continued

Phenotypic table for cases with developmental delay and CNVs impacting GIT1, PPP1R9A, and MVB12B gene. The cases are listed only if the phenotypic information was available.

| Case ID | Critical Exon Gene | Size | Copy Number | CNV (Inheritance) | Age of Ascertainment | Developmental Delay/ID | Dysmorphic Features | Other Clinical Features |
|---|---|---|---|---|---|---|---|---|
| 7D_DN | GIT1 | 3.5 Mb | Loss | 17q11.2 27.274 to 30.817 Mb (de novo) | 3 months | — | — | Prematurity, tetralogy of Fallot, bilateral choroid plexus cyst, imperforate anus, ambiguous genitalia |
| 2D | GIT1 | 3.1 Mb | Loss | 27.869 to 31.043 Mb | N/A | Developmental delay and/or ID | N/A | N/A |
| 3D | GIT1 | 2.1 Mb | Loss | 27.606 to 29.722 Mb | N/A | Developmental delay and/or ID | N/A | N/A |
| 3G_DN | GIT1 | 466 kb | Gain | 17q11.2 27.696 to 28.162 Mb (de novo) | <1 yr | N/A | N/A | |
| 5G | GIT1 | 9.2 Mb | Gain | 17p11.2q12 20.649 to 29.832 | 14 yr | ID | | Autism, obesity |
| 11D_DN | PPP1R9A | 703 Kb | Loss | 7q21.3 94.823 to 95.024 Mb (de novo) | 3 yrs | Speech delay | — | Repetitive behaviors and sensory sensitivities consistent with autism spectrum disorder |
| 7D | PPP1R9A | 2 Mb | Loss | 7q21.3 92.943 to 94.931 Mb | 12 yrs | — | Triangular facies, broad forehead, thin lips. | Myoclonus dystonia, short stature, failure to thrive, anxiety, obsessive-compulsive behavior. |
| 13D_DN | PPP1R9A | 4.8 Mb | Loss | 7q21.2q21.3 92.388 to 97.197 Mb (de novo) | 4 yrs | Fine and gross motor delay, speech delay, ID | Microcephaly | Short stature, ADHD, hypotonia, autism |
| 12D | PPP1R9A | 2.1 Mb | Loss | 7q21.3 92.992 Mb to 95.058 Mb (Paternal) | 21 months | — | Ear pit, helix | Hyperplasia of right leg; Father has tremors due to SGCE deletion. |
| 9D | PPP1R9A | 1.3 Mb | Loss | 7q21.3 94.909 to 96.189 Mb | 2 yrs | — | | Short stature, sensorineural hearing loss, congenital hip dislocation |
| 4D | PPP1R9A | 5.9 Mb | Loss | 7q21.2q21.3 91.997 to 97.905 Mb | N/A | ID | Micrognathia | Short stature, congenital hip dislocation, short stature, sensorineural hearing loss |
| 3D_DN | PPP1R9A | 6.8 Mb | Loss | 7q21.3q22.1 94.174 to 10.101 Mb (de novo) | <1 yr | ID, speech delay | Epicanthus, posteriorly rotated ears | Ectrodactyly |
| 1D | PPP1R9A | 8.8 Mb | Loss | 93.184 to 102.043 Mb | N/A | Developmental delay and/or ID | N/A | N/A |
| 5D | PPP1R9A | 5.8 Mb | Loss | 93.891 to 99.735 Mb | N/A | Developmental delay and/or ID | N/A | N/A |
| 6D | PPP1R9A | 5.8 Mb | Loss | 89.836 to 95.635 Mb | N/A | Developmental delay and/or ID | N/A | N/A |

TABLE 11-continued

Phenotypic table for cases with developmental delay and CNVs impacting GIT1, PPP1R9A, and MVB12B gene. The cases are listed only if the phenotypic information was available.

| Case ID | Critical Exon Gene | Size | Copy Number | CNV (Inheritance) | Age of Ascertainment | Developmental Delay/ID | Dysmorphic Features | Other Clinical Features |
|---|---|---|---|---|---|---|---|---|
| 10D | PPP1R9A | 1.1 Mb | Loss | 93.926 to 95.027 Mb | N/A | Developmental delay and/or ID | N/A | N/A |
| 5G_DN | MVB12B | 839 Kb | Gain | 9q33.3 128.653 to 129.491 Mb (de novo) | 15 yrs | Learning disability | | Tourette syndrome, ADHD |
| 4G_DN | MVB12B | 471 Kb, 703 Kb | Gains | 9q33.3 128.772 to 129.243 Mb 9q34.11 130.898 to 131.601 Mb (both de novo) | N/A | ID | | Unaffected niece has 9q33.3 gain. |
| 6G_DN | MVB12B | 1.9 Mb, 7.5 Mb | Gains | 9q33q34.11, 128.432 to 130.352 Mb 9q34.11q34.3 130.825 to 138.309 Mb (both de novo) | 2 yrs | N/A | N/A | |
| 1G | MVB12B | 683 Kb | Gain | 129.218 to 129.902 Mb | N/A | Developmental delay and/or ID | N/A | N/A |
| 5D_DN | MVB12B | 330 Kb | Loss | 9q33.3 129.156 to 129.490 Mb (de novo) | N/A | Global Developmental Delay | — | |
| 7D_DN | MVB12B | 980 Kb | Loss | 9q33.3 129.136 to 130.120 Mb (de novo) | 5 yrs | Developmental delay | — | Patellar aplasia |
| 6D_DN | MVB12B | 470 Kb, 700 Kb | Loss | 9q33.3 128.772 to 129.243 Mb 9q34.11 130.898 to 131.601 Mb (Both de novo) | N/A | Developmental Delay, ID | — | Autism |
| 3D_DN | MVB12B | 1.2 Mb | Loss | 9q33.3 128.652 to 129.871 Mb (de novo) | <1 yr | N/A | N/A | |
| 1D_DN | MVB12B | 2.8 Mb | Loss | 9q33.3q34.11 128.460-131.260 (de novo) | 1 yr | ID | Brachycephaly, microcephaly | Feeding difficulties at infancy |
| 12D_DN | MVB12B | 3.6 Mb | Loss | 9q33.3q34.11 127.818-131.400 Mb (de novo) | 18 yrs | Developmental delay | — | Seizures; deletion includes STXBP1 |
| 2D_DN | MVB12B | 4.1 Mb | Loss | 9q33.3q34.11 128.870 to 132.995 Mb (de novo) | 1 yr | N/A | N/A | |
| 4D_DN | MVB12B | 4.1 Mb | Loss | 9q33.3q34.11 127.213 to 131.263 Mb (de novo) | 9 yrs | N/A | N/A | |

Another candidate gene was ascertained, multivesicular body subunit 12B (MVB12B), with enrichment of critical exons and also clustered with genes in the 'blue' network that were reported to be impacted by de novo exonic mutations in individuals with neuropsychiatric conditions. Initially a single de novo duplication was observed in the cohort, but subsequently 18 VOUS involving this gene were found, including 12 that were de novo in origin (8 deletions and 4 duplications) (FIG. 28). This included 3 recurrent de novo CNVs ascertained from developmental delay cases impacting only the MVB12B gene (FIG. 28 and Table 11 cases 6D-DN, 4G-DN and 3G). The protein encoded by this gene is an endosomal sorting complex required for transport (ESCRT-I) which is involved in sorting of ubiquitinated cargo protein from the plasma membrane. Mutations in the ESCRT complex family have been implicated in frontotemporal dementia, a neurodegenerative disease. The data included a de novo 839 kb duplication in a child (case 5G-DN) with Tourette syndrome, attention deficit hyperactivity disorder and learning disability. Another case had an adjacent de novo 700 kb duplication, and was described as having severe intellectual disability, whereas an individual (FIG. 28, case 3G) with a recurrent duplication was reported to be normal, thereby demonstrating variable expression (or reduced penetrance) of the duplication. Deletions were found in cases referred for developmental delay and reported to have other comorbid conditions (Table 11). The 73 kb smaller transcript of this gene (NM_001011703.2) containing the 'critical exons' in the analysis was impacted by 12 of the reported de novo VOUS and no CNVs in controls.

Quantitative PCR analysis of 11 tissues for both MVB12B and PPP1R9A showed prenatal and adult brain-specific mRNA expression relative to that of the MED13 gene (or the ACTB gene).

The present data set showed enrichment of deletion variants (4 VOUS, 1 de novo) containing another gene from the candidate list: the protein phosphatase 1 regulatory subunit 9A (PPP1R9A) (MIM: 602468) gene. Deletions within PPP1R9A gene were identified in developmental disorder cases and controls. The breakpoints of 13 VOUS deletions were found to impact PPP1R9A and nearby genes. The breakpoints include 4 de novo VOUS reported from developmental delay cases. There was no deletion found in the control dataset. The shortest de novo deletion was 201 Kb ascertained from a case (11D_DN) with developmental delay in the present cohort. This particular de novo also impacted the PON gene family where exonic deletions were also present in controls. The human protein co-expression network revealed PPP1R9A gene is the within the blue protein module and enriched for 'critical exons' and putative ASD genes reported to have de novo mutations.

Additional data sets revealed 18 CNVs (13 deletions and 5 duplications), including 3 additional de novo deletions impacting exons of the gene. PPP1R9A is the only gene from within the de novo variants that is enriched with critical exons and clustered within the blue protein module. The nearby genes are impacted by polymorphic deletions in controls, whereas no deletions encompassing PPP1R9A were identified from the control data set. A de novo missense mutation of this gene was recently reported in an ASD proband. This gene shows tissue-specific imprinting; it is maternally expressed in skeletal muscle, but both alleles are expressed in other embryonic tissues, including the brain. The protein encoded by this gene, Neurabin I, is a key candidate molecule in synaptic formation and function. PPP1R9A also has a role in synaptic structure and function, spine motility and neurite formation. Enrichment of critical exons of this gene within adult brain regions were found, and it is part of the 'blue' module. An individual with autism was reported to have a de novo missense variant of PPP1R9A and a rare LOF mutation was reported in a schizophrenia case. This gene also shows increased expression in brain from individuals with bipolar disorder compared with controls. Upon further investigation of the 'blue' protein co-expression network, highly connected neighboring (first degree) genes of PPP1R9A were reported to have de novo mutations in individuals with neuropsychiatric conditions. In the present cohort, a focal de novo 201 kb deletion affecting this gene was found in a child (Table 11, case 11D-DN) referred for language delay, repetitive behaviors and sensory sensitivities, consistent with her diagnosis of ASD. A 2 Mb deletion impacting 15 genes—including PPP1R9A and the sarcoglycan epsilon (SGCE) (MIM: 604149) gene—was found in a 12 year old girl (case 7D) referred for myoclonus dystonia, short stature, failure to thrive, severe anxiety and obsessive-compulsive behaviour. She also had mild dysmorphic features (triangular facies, broad forehead, thin lips) but no cognitive concerns were reported.

The brain transcriptome and proteomic method implemented here can infer candidate genes from within the boundaries of a pathogenic or VOUS CNV that are likely to impact brain-related conditions. Thus, the present methods represent a quantifiable approach to screen for genes that are candidates to be involved in developmental disorders such as neurodevelopmental disorders, through the coordinated application of multiple genome-scale data sets. The critical exon approach reveals a negative selective pressure, whereas the protein expression analysis brings out networks that are in pathways biologically relevant to neurodevelopmental disorders. Through the approach described in this study, it is demonstrated that the combined use of different types of molecular data from the human brain may be used to interpret and identify candidate genes for developmental disorders, from pathogenic variants and VOUS. This approach may also be developed using comparable tissue-specific molecular tools to reveal candidates for other classes of disorders.

Relevant portions of references referred to herein are incorporated by reference.

The invention claimed is:

1. A method of detecting a critical exon associated with Autism Spectral disorder (ASD) in a nucleic acid sample from a mammal, comprising the steps of:
   i) detecting exons within a target gene[s] in the nucleic acid sample which exhibit an expression level greater than the 75th percentile of exon expression levels in genes from a control using nucleic acid primers that target exons within the target gene[s] selected from the group consisting of:
   TGACATCGCACGTCCATCTG (SEQ ID NO: 1) and ACAGGTAGTAAATGGCCCAGG (SEQ ID NO: 2);
   GAGCCTTCCTGATCCCCTAT (SEQ ID NO: 3) and ACTGTTTCCACGGCAGTGT (SEQ ID NO: 4);
   TGACATCGCACGTCCATCTG (SEQ ID NO: 1) and ACTGTTTCCACGGCAGTGT (SEQ ID NO: 4);
   CGGCTGCTGTGCTATCATTC (SEQ ID NO: 5) and CAGCCAACACCCTTCCAGAT (SEQ ID NO: 6);
   GAGCCTTCCTGATCCCCTAT (SEQ ID NO: 3) and CAGCCAACACCCTTCCAGAT (SEQ ID NO: 6);
   GGCTGGATAAGCCAGGTCAG (SEQ ID NO: 7) and GGAAAGAGTTGTAGCTCCCGA (SEQ ID NO: 8);
   CCTGTTCTTCCGTGGAGTGA\(SEQ ID NO: 9) and CATGAAGCCCACGATGGAGA (SEQ ID NO: 10); and
   GGCTGGATAAGCCAGGTCAG (SEQ ID NO: 11) and TACTCATCCACCAGGGCTGT (SEQ ID NO: 12);
   ii) detecting rare mutations which occur at a frequency of less than 0.05 as compared to a control or de novo sequence mutations not possessed by either parent of the nucleic acid sample within each exon detected in step i) and determining the burden of mutation of each exon by dividing the number of rare mutations in each exon by the length of the exon; and
   iii) detecting a critical exon having a burden of mutation that is less than the $75^{th}$ percentile of mutations in the exon and inversely correlates with the exon expression level,
   wherein the target gene is SLC6A1.

2. The method of claim 1, wherein the nucleic acid-containing sample is selected from neocortex, amygdala, cerebellar cortex, hippocampus, mediodorsal nucleus of the thalamus, and striatum.

3. The method of claim 2, wherein the sample is a cerebellar cortex sample.

4. The method of claim 1, wherein the sample is a prenatal, child or adult sample.

5. The method of claim 1, wherein the rare or de novo mutations are selected from the group of missense, frameshift, nonsense, splice-site variants and copy number variations.

6. The method of claim 5, wherein the mutations are missense mutations.

7. The method of claim 1, additionally comprising conducting a gene co-expression analysis before step i) to detect in the sample genes that encode proteins relevant to the disease for analysis in step i).

8. The method of claim 7, wherein the co-expression analysis is a Weighted Gene Co-expression Network Analysis.

* * * * *